United States Patent [19]

Van Daele

[11] Patent Number: 5,137,896
[45] Date of Patent: Aug. 11, 1992

[54] N-(3-HYDROXY-4-PIPERIDINYL)BENZA-MIDE DERIVATIVES

[75] Inventor: Georges Van Daele, Turnhout, Belgium

[73] Assignee: Janssen Pharmaceutica N.V., Beerse, Belgium

[21] Appl. No.: 748,227

[22] Filed: Aug. 20, 1991

Related U.S. Application Data

[60] Division of Ser. No. 535,939, Jun. 11, 1990, Pat. No. 5,057,525, which is a division of Ser. No. 443,060, Nov. 28, 1989, Pat. No. 4,962,115, which is a continuation of Ser. No. 258,310, Oct. 17, 1988, abandoned, which is a continuation of Ser. No. 631,526, Jul. 18, 1984, abandoned, which is a continuation of Ser. No. 403,603, Jul. 30, 1982, abandoned, which is a continuation-in-part of Ser. No. 307,409, Oct. 1, 1981, abandoned.

[51] Int. Cl.$^5$ .................. A61K 31/445; C07D 211/22
[52] U.S. Cl. ..................................... 514/327; 514/326; 546/209; 546/221
[58] Field of Search ............... 546/209, 225, 226, 221; 514/326, 327

[56] References Cited

U.S. PATENT DOCUMENTS

| 4,105,666 | 8/1978 | Ward | 546/224 |
| 4,367,232 | 1/1983 | Boix-Igleasias et al. | 424/267 |
| 4,962,115 | 10/1990 | Van Daele | 546/224 |
| 5,057,525 | 10/1991 | Van Daele | 514/318 |

FOREIGN PATENT DOCUMENTS 1575310  9/1980  United Kingdom .

OTHER PUBLICATIONS

J. Prieto et al., "Synthesis and Pharmacological Properties of a Series of Antidopaminergic Piperidyl Benzamides", J. Pharm. Pharmac., 1977, 29, pp. 147-152.

Primary Examiner—C. Warren Ivy
Assistant Examiner—Celia Chang
Attorney, Agent, or Firm—Charles J. Metz

[57] ABSTRACT

Novel N-(3-hydroxy-4-piperidinyl)benzamides and derivatives thereof, said compounds being useful as stimulators of the motility of the gastro-intestinal system.

15 Claims, No Drawings

N-(3-HYDROXY-4-PIPERIDINYL)BENZAMIDE DERIVATIVES

CROSS-REFERENCE TO RELATED APPLICATION

This application is a division of copending application Ser. No. 535,939, filed Jun. 11, 1990, now U.S. Pat. No. 5,057,525, which was a division of application Ser. No. 443,060, filed Nov. 28, 1989, now U.S. Pat. No. 4,962,115, which was a continuation of application Ser. No. 258,310, filed Oct. 17, 1988, now abandoned, which was a continuation of application Ser. No. 631,526, filed Jul. 18, 1984, now abandoned, which was a continuation of application Ser. No. 403,603, filed Jul. 30, 1982, now abandoned, which was a continuation-in-part of application Ser. No. 307,409, filed Oct. 1, 1981, now abandoned.

BACKGROUND OF THE INVENTION

A number of N-piperidinyl benzamides, bearing a substituent in the 1-position of the piperidine ring, are described, for example, in U.S. Pat. Nos.
3,647,805,
4,069,331, and
4,138,492,
said benzamides being taught to be useful in the treatment of gastric ulcers, psychic disorders and migraine and as anti-emetics.

The compounds of the present invention differ from the prior art compounds by their substitution in the 3-position of the piperidine ring and by their pharmacological properties as stimulators of the motility of the gastro-intestinal system.

DESCRIPTION OF THE PREFERRED EMBODIMENTS

The present invention is concerned with novel N-(4-piperidinyl)benzamides having the formula

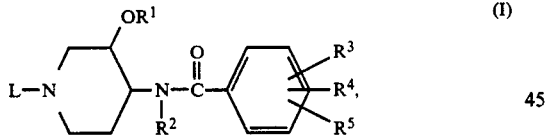

the pharmaceutically acceptable acid addition salts, the stereochemically isomeric forms and the pharmaceutically acceptable quaternary ammonium salts thereof, wherein:

$R^1$ is a member selected from the group consisting of hydrogen, lower alkyl, $(Ar^1)$ lower alkyl, lower alkylcarbonyl, aminolower alkyl and mono- and di (lower alkyl)aminolower alkyl;

$R^2$ is a member selected from the group consisting of hydrogen and lower alkyl;

$R^3$, $R^4$ and $R^5$ are each independently selected from the group consisting of hydrogen, lower alkyl, lower alkyloxy, halo, hydroxy, cyano, nitro, amino, mono-and di (lower alkyl)amino, aminocarbonyl, $(Ar^1)$ carbonylamino, lower alkylcarbonylamino, lower alkylcarbonyl, lower alkylcarbonyloxy, aminosulfonyl, lower alkylsulfinyl, lower alkylsulfonyl, lower alkylthio and mercapto; and L is a member selected from the group consisting of hydrogen, lower alkyloxycarbonyl, di($Ar^1$)cycloalkyl, ($Ar^1$O)cycloalkyl, 2,3-dihydro-1H-indenyl, a radical having the formula $$-C_rH_{2r}-R \qquad (a)$$

wherein r is an integer of from 1 to 6 inclusive and R is $Ar^2$; and
a radical having the formula $$-C_nH_{2n}-X-C_mH_{2m}-Y-Q \qquad (b),$$

wherein n is an integer of from 1 to 4 inclusive, X is a member selected from the group consisting of a direct bond, —CH(OH)— and —NH—, m is 0 or an integer of from 1 to 4 inclusive, Y is a bivalent radical selected from the group consisting of a direct bond, —CO—, —NHCO—, —CONH—, —CH=CH—, C—$CR^8$(Q), —C($OR^6$) ($R^7$)— and, where m is other than 0, Y may also be —O—, —S—, —$SO_2$—, and $NR^9$—, wherein $R^6$ is lower alkyl, $R^7$ is hydrogen, cycloalkyl, lower alkyloxy, or lower alkyl, $R^8$ is hydrogen, $Ar^1$, lower alkyloxycarbonyl, cyano, aminocarbonyl, or mono- or di(lower alkyl)aminocarbonyl, $R^9$ is lower alkyl, $Ar^1$, ($Ar^1$)lower alkyl, ($Ar^1$)carbonyl, or ($Ar^1$)sulfonyl and, where X is other than a direct bond, $R^6$ and $R^9$ may each be hydrogen; and Q is hydrogen, cycloalkyl, $Ar^1$, di($Ar^1$)methyl, tri-($Ar^1$)methyl, and, when Y is other than a direct bond, Q may also be lower alkyl or ($Ar^1$)lower alkyl;

wherein $Ar^1$ is a member selected from the group consisting of phenyl being optionally substituted with up to 3 substituents each independently selected from the group consisting of halo, hydroxy, lower alkyl, lower alkyloxy, aminosulfonyl, lower alkylcarbonyl, nitro, trifluoromethyl, amino, aminocarbonyl and phenylcarbonyl, said phenyl being optionally substituted with up to 3 halo atoms, and thienyl being optionally substituted with halo or lower alkyl; and $Ar^2$ is a member selected from the group consisting of naphthalenyl, thienyl, pyridinyl, pyrazinyl, 1H-indolyl, 1H-benzimidazolyl, 2,3-dihydro-2-oxo-1H-benzimidazolyl being optionally substituted with 1 or 2 halo atoms, 4,5,6,7-tetrahydro-1H-benzimidazolyl, benzodioxolyl, 2,3-dihydro-1,4-benzodioxinyl, imidazolyl being optionally substituted with a lower alkyl radical, imidazo[1,2-a]-pyridinyl being optionally substituted with a lower alkyl radical, 1,4-dihydro-2,4-dioxo-quinazolinyl, isoxazolyl being optionally substituted with an aryl radical, (1H-imidazolyl)phenyl, furanyl being optionally substituted with a lower alkyloxycarbonyl radical, 2,2-di($Ar^1$)-1,3-dioxolanyl and 1-($Ar^1$)-1,3-dihydro-1-isobenzofuranyl In the foregoing definitions the term "halo" is generic to fluoro, chloro, bromo and iodo; the term "lower alkyl" is meant to include straight and branched saturated hydrocarbon radicals having from 1 to 6 carbon atoms such as, for example, methyl, ethyl, 1-methylethyl, 1,1-dimethylethyl, propyl, butyl, pentyl, hexyl and the like; and the term "cycloalkyl" denotes cyclic hydrocarbon radicals, comprising cyclopropyl, cyclobutyl, cyclopentyl and cyclohexyl radicals.

Preferred compounds within the scope of the present invention are those wherein $R^3$, $R^4$ and $R^5$ are, each independently from each other, selected from the group consisting of halo, amino, mono- and di(lower alkyl)-amino and lower alkyloxy.

Particularly preferred compounds are those wherein $R^3$ is methoxy, $R^4$ is amino or methylamino and $R^5$ is chloro, said $R^3$, $R^4$ and $R^5$ being attached to the phenyl ring in the 2-, respectively 4- and 5-positions.

An especially preferred compound within the present invention is cis-4-amino-5-chloro-N-[1-[3-(4-fluorophenoxy)propyl]-3-methoxy-4-piperidinyl]-2-methoxybenzamide.

The compounds of formula (I) may generally be prepared by the reaction of an amine of formula

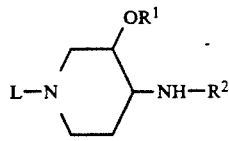  (II)

with an appropriately substituted carboxylic acid of formula

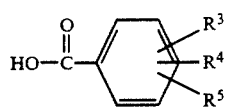  (III)

or a functional derivative thereof. Suitable functional derivatives are acyl halides, having the formula

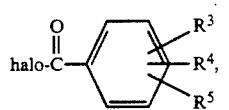  (III-a)

esters, having the formula

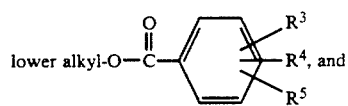  (III-b)

anhydrides, having the formula

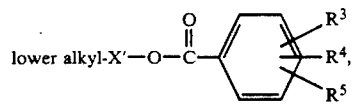  (III-c)

wherein X' is

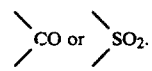

The reaction of (II) with (III), (III-a), (III-b) or (III-c) may conveniently be carried out by stirring and, if desired, heating the reactants together in the presence of a suitable reaction-inert solvent such as, for example, a halogenated hydrocarbon, e.g., dichloromethane and the like.

The water, the alcohol or the acid which is liberated during the coarse of the reaction is preferably removed from the reaction mixture following art-known procedures such as, for example, by azeotropical destillation, by complexation, by salt-formation and the like methods.

The compounds of formula (I) wherein $R^1$ is hydrogen and wherein the substituents in the 3- and 4-positions of the piperidine ring have the trans configuration, said compounds being represented by the formula (I-a-1), can aslo be prepared by reacting a 7-oxo-3-azabicyclo[4,1,0]-heptane of formula (IV) with a benzamide of formula (V). The compounds of formula (I) wherein the substituents in the 3- and 4-positions of the piperidine ring have the trans configuration and wherein $R^1$ is other than hydrogen, said $R^1$ being represented by $R^{1-a}$ and said compounds by the formula (I-a-2), may be derived from the compounds of formula (I-a-1) by reacting the latter with (VI) following art-known O-alkylating procedures.

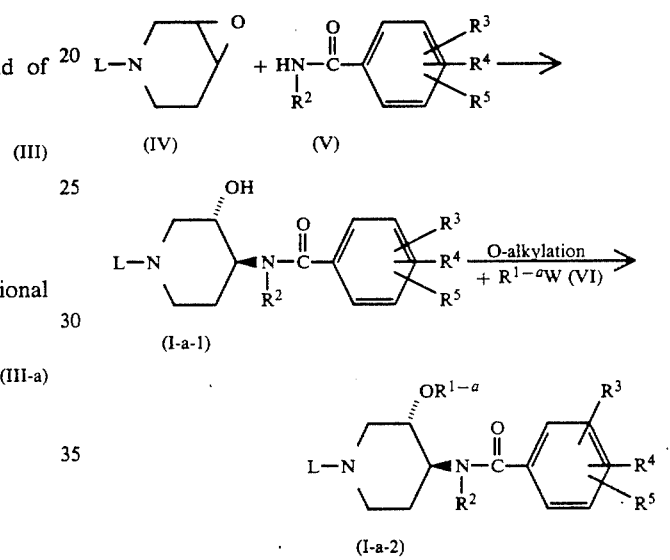

In (VI) W has the meaning of a reactive leaving group such as, halo, preferably, chloro, bromo or iodo, a sulfonyloxy group, e.g., methylsulfonyloxy, 4-methylphenylsulfonyloxy, lower alkylcarbonyloxy, such as, acetoxy, and the like.

The reaction of (IV) with (V) may conveniently be conducted by stirring and, if desired, heating the reactants together in a suitable reaction-inert solvent, such as, for example, an alcohol, e.g., ethanol and the like.

The O-alkylation or O-acylation is conveniently conducted in an inert organic solvent such as, for example, an aromatic hydrocarbon, e.g., benzene, methylbenzene, dimethylbenzene and the like; alower alkanol, e.g., methanol, ethanol, 1-butanol and the like; a ketone, e.g., 4-methyl-2-pentanone and the like; an ether, e.g., 1,4-dioxane, 1,1'-oxybisethane and the like; N,N-dimethylformamide; nitrobenzene and the like. The addition of an appropriate base such as, for example, an alkali metal carbonate or hydrogen carbonate, or an organic base such as, for example, N,N-diethylethanamine and the like may be utilized to pick up the acid which is liberated during the course of the reaction. In certain cases the addition of an iodide salt, preferably an alkali metal iodide, is appropriate. Somewhat elevated temperatures may be used to enhance the reaction rate.

The compounds of formula (I) wherein the substituents in the 3- and 4-positions of the piperidine ring have the cis configuration, said compounds being represented by the formula (I-b), can also be prepared by the reductive N-alkylation reaction of a piperidinone of formula (VII) with a benzamide of formula (V).

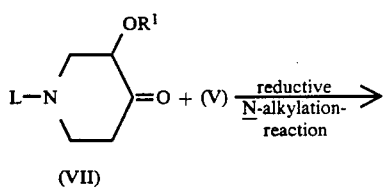

(VII)

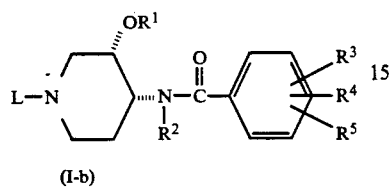

(I-b)

Said reductive N-alkylation-reaction may conviently be carried out by catalytically hydrogenating a stirred and heated mixture of the reactants in a suitable reaction-inert organic solvent according to art-known catalytically hydrogenating procedures. Suitable solvents are, for example, water; lower alkanols, e.g., methanol, 2-propanol and the like; cyclic ethers, e.g., 1,4-dioxane and the like; halogenated hydrocarbons, e.g., trichloromethane and the like; N,N-dimethylformamide; dimethyl sulfoxide and the like; or a mixture of 2 or more of such solvents. The term "art-known catalytically hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction-mixture, e.g., thiophene and the like.

The compounds of formula (I) may also be converted into each other following art-known functional group-transformation procedures.

The compounds of formula (I) wherein L is hydrogen, said compounds being represented by the formula (I-c), can be converted into the corresponding compounds of formula (I) wherein L is other than hydrogen, said L being represented by $L_1$ and said compounds by the formula (I-d), following art-known N-alkylating or N-acylating procedures by reacting the former with a reagent of formula (VIII).

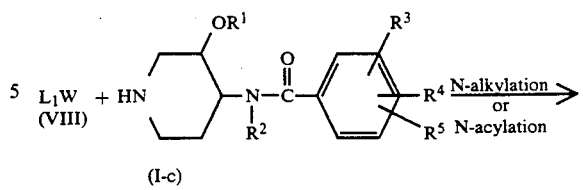

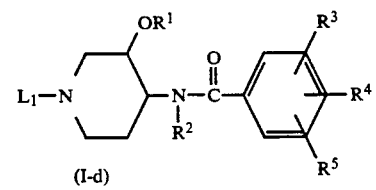

(I-d)

In the reagent of formula (VIII) $L_1$ has the meaning as previously described for L provided that hydrogen is not included.

In some particular cases it may be advantageous to react the reagent of formula (III) with a precursor of a reagent of formula (II).

The compounds of formula (I) wherein L is other than hydrogen or lower alkyloxycarbonyl, said L being represented by $L_2$ and said compounds by the formula (I-e), can also be prepared by the reductive amination reaction of an appropriate carbonyl compound of formula $L_2'{=}C{=}O$ (IX), said $L_2'{=}C{=}O$ being a compound of formula $L_2$—H wherein a —CH$_2$— radical is displaced by a carbonyl radical.

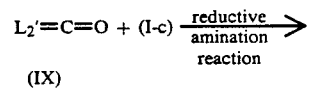

(IX)

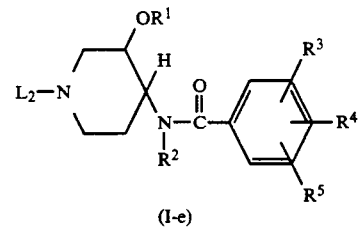

(I-e)

In case $L_2$ is a cycloalkyllower alkyl radical the compounds of formula (I-e) may also be prepared starting from a corresponding reagent of formula (IX) wherein said ring is fully or partly unsaturated.

The compounds of formula (I) wherein L represents a radical of formula Q—Y—C$_m$H$_{2m}$—NH—CH$_2$—CH$_2$—, said compounds being represented by the formula (I-f), can also be prepared by reacting a reagent of formula (X) with a piperidine of formula (I-c).

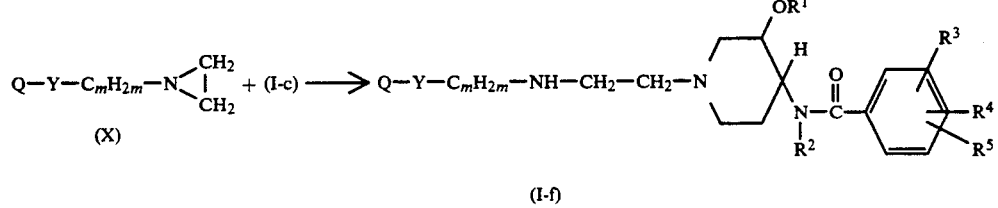

(I-f)

The compounds of formula (I) wherein L represents a radical of formula Q—Y—C$_m$H$_{2m}$—CH(OH- )—CH$_2$—, said compounds being represented by the formula (I-g), can also be prepared by reacting an oxirane of formula (XI) with a piperidine of formula (I-c).

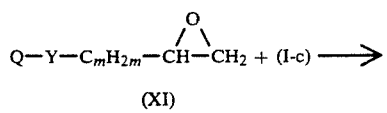

(XI)

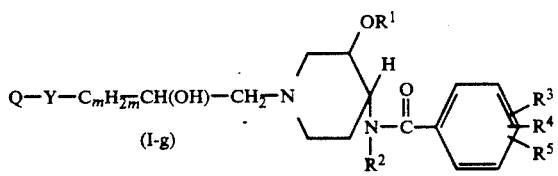

(I-g)

The preparation of the compounds of formula (I-f) and (I-g) starting from (X) and (I-c), respectively (XI) and (I-c), can conveniently be conducted in a suitable reaction-inert organic solvent such as, for example, an alcohol, such as, for example, methanol, ethanol, 2-propanol and the like, or an aliphatic or alicyclic ketone, such as, for example, 2-propanone, 2-butanone, 4-methyl-2-pentanone, cyclohexanone and the like. The addition of an appropriate base, such as, for example, an alkali metal carbonate or hydrogen carbonate, may be utilized to enhance the rate of reaction. The reaction is preferably carried out at a somewhat elevated temperature and most preferably at the reflux temperature of the reaction mixture.

The compounds of formula (I) wherein L is lower alkyloxycarbonyl, said compounds being represented by the formula (I-h), may be converted into the corresponding compounds of formula (I-c), by stirring and, if desired, heating the starting compounds (I-h) in a suitable organic solvent such as, for example, an alcohol, e.g., 2-propanol and the like, an ether, e.g., tetrahydrofuran and the like, in the presence of an appropriate base, e.g., alkali- or earth alkaline metal hydroxides, carbonates or hydrogen carbonates, e.g., sodium hydroxide, potassium carbonate, sodium hydrogen carbonate and the like.

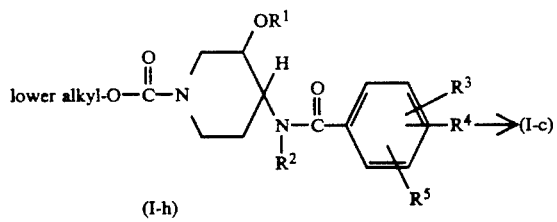

(I-h)

The compounds of formula (I) wherein L is an Ar$^2$CH$_2$-radical, said compounds being represented by the formula (I-i), may, for example, be converted into the compounds of formula (I-c) by a catalytic hydrogenolysis reaction, e.g., by stirring the starting (I-i) in a suitable reaction-inert solvent, such as, methanol and the like solvents, under hydrogen atmosphere, in the presence of an appropriate catalyst such as, for example, palladium-on-charcoal, platinum-on-charcoal and the like. In case R$^1$ is an arylmethyl radical, said radical may simultaneously be converted into the hydrogen radical.

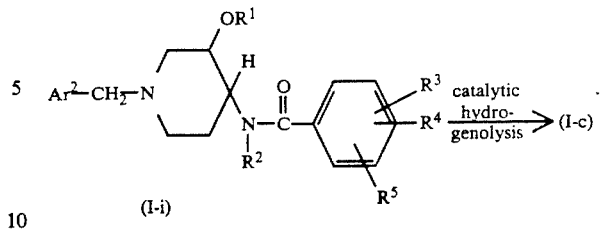

(I-i)

A number of the radicals R$^1$, R$^2$, R$^3$, R$^4$ and/or R$^5$ may also be converted into each other following art-known functional group transformation procedures. For example, the nitro function may be converted into an amine function following art-known nitro-to-amine reducing procedures by stirring and, if desired, heating the starting nitro-compound in a suitable solvent, e.g., methanol and the like, in the presence of an appropriate catalyst, e.g., palladium-on-charcoal, platinum-on-charcoal and the like. A cyanide function may be converted into an aminocarbonyl function by stirring the starting compound in strong acidic medium, e.g., in concentrated sulfuric acid and the like. A lower alkylcarbonyloxy function can be converted into a hydroxy-function following art-known alkaline-hydrolysis procedures. Vice versa, the hydroxy function can be converted into a lower alkylcarbonyloxy function by stirring the former with an appropriate acylating agent, e.g., an acid anhydride and the like.

From formula (I) it is evident that the compounds of this invention have at least two asymmetric carbon atoms in their structure, namely those located in the 3- and the 4-positions of the piperidine nucleus, and consequently they can exist under different stereochemically isomeric forms. The stereochemically isomeric forms of (I) and the pharmaceutically acceptable acid addition salts thereof are intended to be embraced within the scope of this invention.

The diastereomeric racemates of (I), denoted as cis and trans forms respectively, according to the rules described in C.A., 76, Index Guide, Section IV, p. 85 (1972), may be obtained separately by conventional methods. Appropriate methods which may advantageously be employed therefore include, for example, selective crystallization and chromatography separation, e.g., column-chromatography.

Since the stereochemical configuration is already fixed in the intermediates (II) it is also possible to separate cis and trans forms at this or even an earlier stage, whereupon the corresponding forms of (I) may be derived therefrom in the previously indicated manner. The separation of cis and trans forms of such intermediates may be performed by conventional methods as described hereinabove for the separation of cis and trans forms of the compounds of formula (I).

It is evident that the cis and trans diastereomeric racemates may be further resolved into their optical isomers, cis(+), cis(−), trans(+) and trans(−) by the application of methodologies known to those skilled in the art.

The compounds of formula (I) having basic properties may be converted to their therapeutically useful acid addition salts by reaction with an appropriate acid, such as, for example, an inorganic acid such as hydrohalic acid, i.e., hydrochloric, hydrobromic or hydroiodic acid; sulfuric, nitric or thiocyanic acid; a phosphoric acid; and organic acid such as acetic, propanoic, hydroxyacetic, 2-hydroxypropanoic, 2-oxopropanoic, ethanedioic, propanedioic, 1,4-butanedioic, (Z)-2-butenedioic, (E)-2-butenedioic, 2-hydroxy-1,4-butanedioic, 2,3-dihydroxy-1,4-butanedioic, 2-hydroxy-1,2,3-propanetricarboxylic, benzoic, 3-phenyl-2-propenoic, α-hydroxybenzeneacetic, methanesulfonic, ethanesulfonic, 2-hydroxyethanesulfonic, 4-methylbenzenesulfonic, 2-hydroxybenzoic, 4-amino-2-hydroxybenzoic, 2-phenoxybenzoic or 2-acetyloxybenzoic acid.

The salts are in turn converted to the corresponding free bases in the usual manner, e.g., by reaction with alkali such as sodium or potassium hydroxide.

The compounds of formula (I) may conveniently be converted into their quaternary ammonium salts by reacting the former with an appropriate quaternizing agent and, if desired, subsequently exchanging the anion of the thus obtained quaternary compound.

A number of the intermediates and starting materials used in the foregoing preparations are known compounds, others may be prepared according to art-known methodologies of preparing similar compounds and some of them are novel and consequently their preparations will be described hereinafter.

The intermediates of formula (II) can generally be prepared in a stereospecific way starting from an appropriately substituted 7-oxa-3-azabicyclo[4,1,0]-heptane (XII) or from an appropriately substituted 4-piperidinone (XIII) as shown in scheme 1, wherein P represents an appropriate protective group such as, for example, phenylmethyl, ethoxycarbonyl and the like protective groups.

The intermediates (II) having the substituents in the 3- and 4-positions of the piperidine ring in trans configuration and $R^1$ being hydrogen, (II-a-1), can be prepared by reacting (XII) with a reagent of formula (XIV) and eliminating P of the thus obtained (XV). The intermediates (II) having the substituents in the 3- and 4-position of the piperidine ring in trans configuration and $R^1$ being $R^{1-a}$, (II-a-2), can be derived from (II-a-1), by reacting the latter with (VI). The intermediates (II-a-2) can also be prepared by reacting (XV) with (VI) and subsequently eliminating P of the thus obtained (XVI).

The intermediates (II) having the substituents in the 3- and 4-positions of the piperidine ring in cis configuration, (II-b), can be prepared by reacting (XIII) with (XIV), following art-known reductive N-alkylating procedures, and subsequently eliminating P of the thus obtained (XVII).

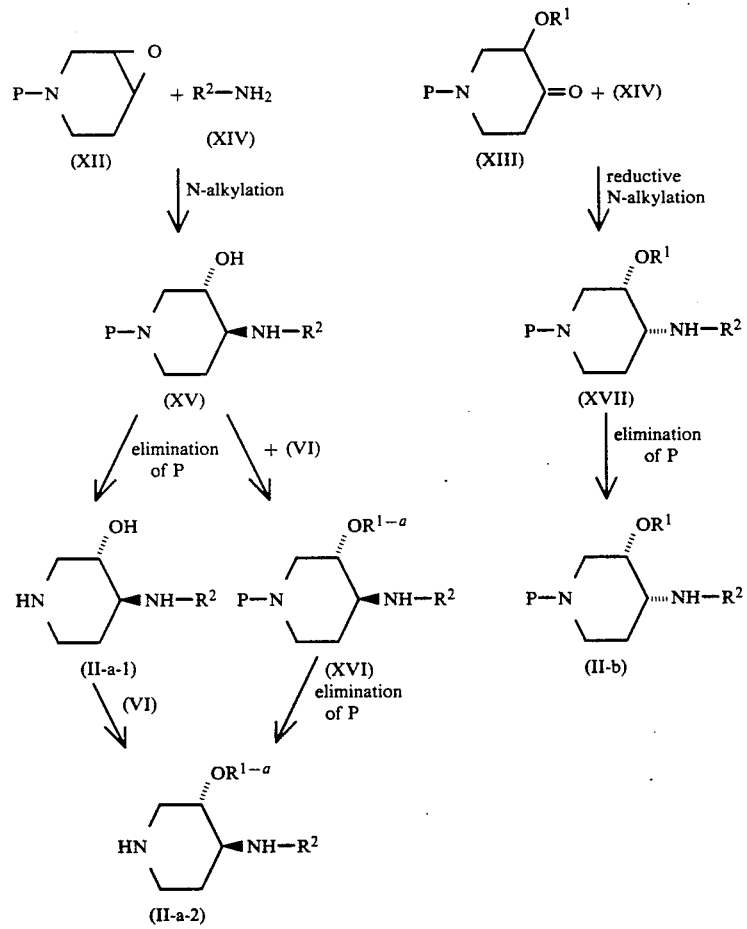

Scheme 1

The trans-4-amino-3-piperidinols (XV) can be converted into the corresponding cis-4-amino-3-piperidinols (XVII), following art-known standard methods, e.g., by converting the amine function into an amide function, converting the alcohol function into an appropriate leaving group with retention of the configuration and, finally, reacting the thus obtained intermediates with hydrazine, if desired, at elevated temperature.

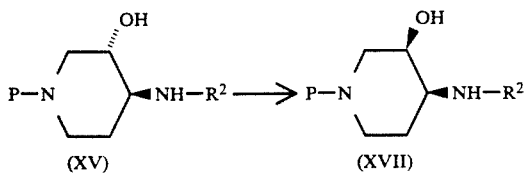

An analogous convertion has been described in Helv. Chim. Acta 62, 932-941 (1979).

The intermediates (IV), respectively (VII), can be derived from (XII), respectively (XIII) by eliminating P and subsequently reacting the thus formed intermediates of formula (IV), respectively (VII) wherein L is hydrogen, (IV-a), respectively (VII-a) with (VIII) following art-known N-alkylating or N-acylating procedures.

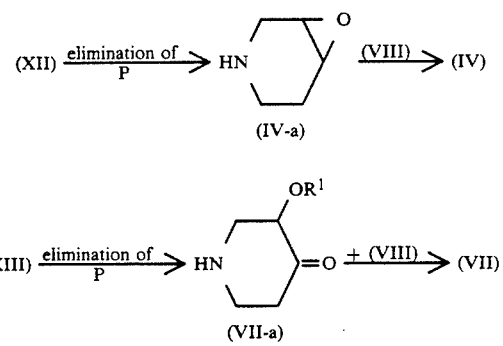

The 7-oxa-3-azabicyclo[4,1,0]heptanes (XII), used as starting materials in the foregoing reactions, may be prepared by oxidizing the corresponding 1,2,3,6-tetrahydropyridines (XIX) with an appropriate epoxidizing agent such as, for example, hydrogen peroxide, 3-chlorobenzeneperoxoic acid and the like.

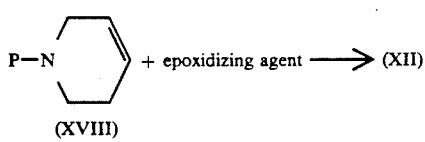

The 4-piperidinones (XIII), used as starting materials in the foregoing reactions, may be derived from an appropriately substituted 4-piperidinone (XIX), e.g., by halogenating (XIX) with a halogenating agent such as bromine and the like and subsequently reacting the thus obtained (XX) with an appropriate alcohol of formula $R^1OH$ or an appropriate alkali metal or earth alkaline metal salt thereof.

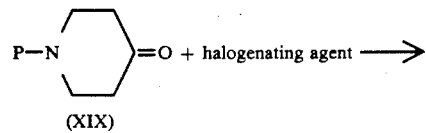

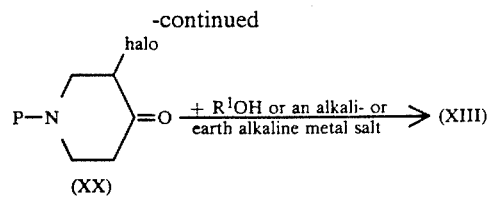

In case a piperidine of formula (XXI) is intermediately formed said (XXI) can be converted into (XIII) by stirring the latter in acidic aqueous medium.

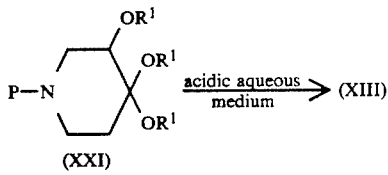

The intermediates of formula (XXI) can be derived from a corresponding vinyl ether by reacting the latter with a suitable epoxidizing agent in an appropriate alcohol (see, for example, Synthetic Communications, 10, (1), 83–87 (1980) and Synthesis, 38–39 (1974).)

The compounds of formula (I), their pharmaceutically acceptable acid addition salts and the stereochemically isomeric forms thereof, when systemically administered to vertebrates, stimulate the motility of the gastro-intestinal system.

The stimulatory effect of the subject compounds on the motility of the gastro-intestinal system is evidenced by the data collected in the tables 1 and 2, which data illustrate the amplification of the contractions of the guinea pig ileum (Test A), the antagonism of dopamine-induced gastric relaxations (Test B) and the antroduodenal motility of the dog (Test C) caused by the subject compounds.

TEST A

Amplification of Contractions Induced by Transmural Stimulation of Guinea-Pig Ileum Non-terminal ileum segments of the guinea-pig were vertically suspended with a preload of 1 g in a 100 ml tyrode bath (37.5° C.) and gassed with a mixture of 95% $O_2$ and 5% $CO_2$. Contractions were measured isometrically. Transmural excitation was applied over the whole length of the ileum strip by means of two platinum electrodes (0.5 mm diameter), the anode was passed through the lumen of the ileum, the cathode was dipped into a physiological solution.

The tissue was excited with single rectangular stimuli of 1 msec duration and submaximal intensity at a frequency of 6 per minute, said stimuli being known to release acetylcholine from intramural nerve endings.

After a stabilization period of 30 minutes, a single dose of the test substance was added to the bath solution and its effect was followed for another 15 minutes. Drug effects are expressed as percentage of the initial contractility value.

Column 1 of table 1 illustrates the lowest effective concentration of the test substance whereby a significant stimulation of the acetylcholine release is noted.

References: Arch. Intern. Pharmacodyn. Ther., 204, 37–55 (1973) and Drug Research 24, 1641–1645 (1974).

TEST B

Antagonism of Dopamine-Induced Gastric Relaxation

Experiments were performed on stomachs taken from fasted guinea pigs. The oesophagus, the first 10 cm of the duodenum, the vagal truncae and the coeliac axic with the gastric branches thereof were removed together with the stomach. The gastro-intestinal content was removed by repeated washing. A polyethylene cannula was placed in the coeliac axis. After ligating the oesophagus, the stomach was filled with 20 ml of saline and suspended in 200 ml of oxygenated (95% $O_2$; 5% $CO_2$) Krebs-Henseleit solution maintained at 37° C. A glass cannula was placed into the duodenum and connected to an ultrasonic transit time device. The cannula was further connected to a bottle of saline ensuring a constant hydrostatic pressure of 6 cm saline in the stomach. With this system changes in gastric content can be continuously recorded. Emptying and filling of the stomach correspond to contractions and relaxations of the gastric wall, respectively. Dopamine (50 μg) was injected via the coeliac axis in volumes of 0.1–0.2 ml. The test substances studied for antagonistic effects were added to the bath solution in 0.5 ml of saline.

Column 2 of table 1 illustrates the lowest effective dose whereby antagonistic effects are observed.

Reference: Life Sciences, 23, 453–457 (1978).

TEST C

Antroduodenal Motility of the Conscious Dog

Strain gauge force transducers are constructed and calibrated ex vivo (see, for example, "Gastrointestinal Motility in Health and Disease", p. 647-654, edited by L. L. Duthie, MTP, Lancaster).

Labrador dogs, weighing 25-33 kg, were implanted with force transducers under aseptic conditions. Transducers were sutured in transverse direction to the serosal side of the gastric antrum and the duodenum (respectively 4 cm and 8 cm from the gastroduodenal junction). The lead wires were brought out via a subcutaneous tunnel on the left costal flank through a stab wound between the scapulas. Before each experiment the connector was soldered to the lead wires. Experiments were started in the ginescence phase of the interdigestive state after a fasting period of 18 hours. Water was available ad libitum. During the experiments the dogs layed down at ease in little carriages. Antroduodenal motor patterns were amplified (J.S.I., transducer amplifier) and recorded on a carbon paper writer (Scwarzer). Parameters measured are:

amplitude (force) of contractions in grams, frequency of contractions and percentage of coordination defined as the relative number of antral waves that propagated to the duodenum. Drugs were administered either orally or via injection into a brachial vein. Drug response was followed for at least 2 hours.

Table 2 shows the minimal effective dose, in mg/kg body weight, whereby the rhythmic activity of the stomach is augmented and regularized.

The data illustrated in tables 1 and 2 are intended to illustrate and not to limit the scope of the present invention.

TABLE 1

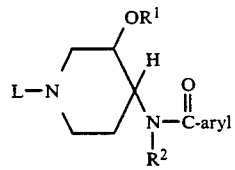

| L | $R^1$ | $R^2$ | aryl | iso-merism | base/salt form | colunm 1 low.effective conc. mg/l | column 2 low.effect conc. mg/l |
|---|---|---|---|---|---|---|---|
| $C_6H_5$—$CH_2$ | $CH_3$ | H | 2-$CH_3O$,4-$NH_2$,5-Cl—$C_6H_2$ | cis | base | 0.01 | 2.5 |
| $C_6H_5$—$CH_2$ | H | H | 2-$CH_3O$,4-$NH_2$,5-Cl—$C_6H_2$ | cis | base | 0.04 | 2.5 |
| $C_6H_5$—CH=CH—$CH_2$ | H | H | 2-$CH_3O$,4-$NH_2$,5-Cl—$C_6H_2$ | cis | base | 0.04 | 2.5 |
| H | $CH_3$ | H | 2-$CH_3O$,4-$NH_2$,5-Cl—$C_6H_2$ | cis | base | 0.04 | — |
| (4-F—$C_6H_4$)$_2$CH(CH$_2$)$_3$ | $CH_3$ | H | 2-$CH_3O$,4-$NH_2$,5-Cl—$C_6H_2$ | cis | HCl | 0.01 | 0.01 |
| 4-F—$C_6H_4$—CO—(CH$_2$)$_3$ | $CH_3$ | H | 2-$CH_3O$,4-$NH_2$,5-Cl—$C_6H_2$ | cis | HCl | 0.0025 | ≦0.16 |
| 4-F—$C_6H_4$—$CH_2$ | $CH_3$ | H | 2-$CH_3O$,4-$NH_2$,5-Cl—$C_6H_2$ | cis | base | 0.0025 | 2.5 |
| $C_6H_5$—CH=CH—$CH_2$ | $CH_3$ | H | 2-$CH_3O$,4-$NH_2$,5-Cl—$C_6H_2$ | cis | base | 0.0025 | 2.5 |
| (2,3-dihydro-2-oxo-1H-benzimidazol-1-yl)-(CH$_2$)$_3$ | $CH_3$ | H | 2-$CH_3O$,4-$NH_2$,5-Cl—$C_6H_2$ | cis | base | 0.01 | 1.25 |
| 4-$CH_3O$—$C_6H_4$—(CH$_2$)$_3$ | $CH_3$ | H | 2-$CH_3O$,4-$NH_2$,5-Cl—$C_6H_2$ | cis | base | 0.04 | 2.5 |
| 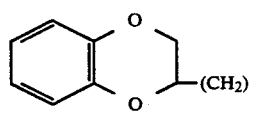 | $CH_3$ | H | 2-$CH_3O$,4-$NH_2$,5-Cl—$C_6H_2$ | cis | base | 0.01 | 0.63 |
| 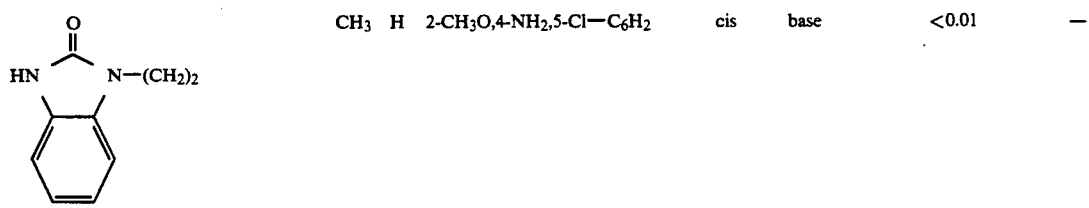 | $CH_3$ | H | 2-$CH_3O$,4-$NH_2$,5-Cl—$C_6H_2$ | cis | base | <0.01 | — |
| $CH_2$=CH—$CH_2$ | $CH_3$ | H | 2-$CH_3O$,4-$NH_2$,5-Cl—$C_6H_2$ | cis | base | 0.0025 | 2.5 |

TABLE 1-continued

| | | | | | | | |
|---|---|---|---|---|---|---|---|
| 4-Cl—C₆H₄—CH₂ | CH₃ | H | 2-CH₃O,4-NH₂,5-Cl—C₆H₂ | cis | base | 0.01 | 1.25 |
| (2,6-Cl₂—C₆H₃)NHCOCH₂ | CH₃ | H | 2-CH₃O,4-NH₂,5-Cl—C₆H₂ | cis | base | 0.04 | — |
| (2,6-Cl₂—C₆H₃)NH—CO(CH₂)₂ | CH₃ | H | 2-CH₃O,4-NH₂,5-Cl—C₆H₂ | cis | base | 0.01 | 0.63 |
| (CH₃)₂CH | CH₃ | H | 2-CH₃O,4-NH₂,5-Cl—C₆H₂ | cis | base | 0.16 | 2.5 |
| 4-F—C₆H₄—O—(CH₂)₃ | CH₃ | H | 2-CH₃O,4-NH₂,5-Cl—C₆H₂ | cis | (COOH)₂ | 0.00016 | 0.31 |
| 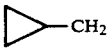 | CH₃ | H | 2-CH₃O,4-NH₂,5-Cl—C₆H₂ | cis | base | 0.00063 | — |
| 3-F—C₆H₄—CH₂ | CH₃ | H | 2-CH₃O,4-NH₂,5-Cl—C₆H₂ | cis | base | 0.04 | ≦2.5 |
| 4-i.C₃H₇—C₆H₄—CH₂ | CH₃ | H | 2-CH₃O,4-NH₂,5-Cl—C₆H₂ | cis | base | 0.04 | ≦0.063 |
| 4-F—C₆H₄CONHCH₂CH₂ | CH₃ | H | 2-CH₃O,4-NH₂,5-Cl—C₆H₂ | cis | base | 0.04 | 2.5 |
| 4-NO₂—C₆H₄—CH₂ | CH₃ | H | 2-CH₃O,4-NH₂,5-Cl—C₆H₂ | cis | base | 0.04 | — |
| 4-CH₃—C₆H₄—CH₂ | CH₃ | H | 2-CH₃O,4-NH₂,5-Cl—C₆H₂ | cis | base | <0.04 | — |
| 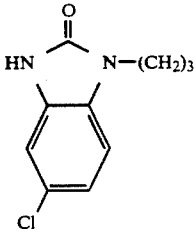 | CH₃ | H | 2-CH₃O,4-NH₂,5-Cl—C₆H₂ | cis | base | 0.04 | 0.63 |
| 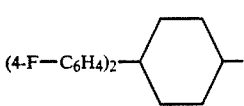 | CH₃ | H | 2-CH₃O,4-NH₂,5-Cl—C₆H₂ | cis | base | 0.16 | 2.5 |
| 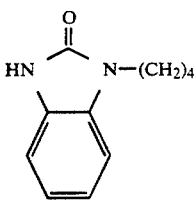 | CH₃ | H | 2-CH₃O,4-NH₂,5-Cl—C₆H₂ | cis | ½H₂O | <0.04 | — |
| 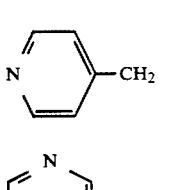 | CH₃ | H | 2-CH₃O,4-NH₂,5-Cl—C₆H₂ | cis | base | 0.16 | — |
| 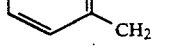 | CH₃ | H | 2-CH₃O,4-NH₂,5-Cl—C₆H₂ | cis | base | 0.16 | — |
| 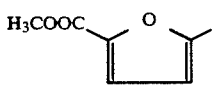 | CH₃ | H | 2-CH₃O,4-NH₂,5-Cl—C₆H₂ | cis | base | 0.16 | — |
| 4-F—C₆H₄—COCH₂ | CH₃ | H | 2-CH₃O,4-NH₂,5-Cl—C₆H₂ | cis | base | 0.04 | 2.5 |
| 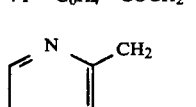 | CH₃ | H | 2-CH₃O,4-NH₂,5-Cl—C₆H₂ | cis | base | 0.0025 | — |
| 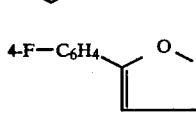 | CH₃ | H | 2-CH₃O,4-NH₂,5-Cl—C₆H₂ | cis | base | 0.16 | — |
| 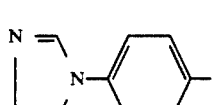 | CH₃ | H | 2-CH₃O,4-NH₂,5-Cl—C₆H₂ | cis | base | 0.04 | 0.63 |

TABLE 1-continued

| L | R¹ | R² | R³,⁴,⁵ | isomerism | salt form | column 1 low.effective conc. mg/l | column 2 low.effective conc. mg/l |
|---|---|---|---|---|---|---|---|
| 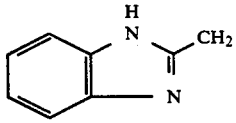 | CH₃ | H | 2-CH₃O,4-NH₂,5-Cl—C₆H₂ | cis | base | 0.16 | — |
| 4-(H₂N—SO₂)—C₆H₄—CH₂ | CH₃ | H | 2-CH₃O,4-NH₂,5-Cl—C₆H₂ | cis | HCl.H₂O | 0.16 | — |
| 3-CF₃—C₆H₄—CH₂ | CH₃ | H | 2-CH₃O,4-NH₂,5-Cl—C₆H₂ | cis | base | 0.16 | 1.25 |
| 3-Cl—C₆H₄—CH=CH—CH₂ | CH₃ | H | 2-CH₃O,4-NH₂,5-Cl—C₆H₂ | cis | H₂O | 0.16 | 0.63 |
|  | CH₃ | H | 2-CH₃O,4-NH₂,5-Cl—C₆H₂ | cis | base | 0.04 | 2.5 |
| 4-CH₃O—C₆H₄—CH₂ | CH₃ | H | 2-CH₃O,4-NH₂,5-Cl—C₆H₂ | cis | H₂O | 0.01 | 2.5 |
| 2,6-(CH₃)₂—C₆H₃—NHCO(CH₂)₂ | CH₃ | H | 2-CH₃O,4-NH₂,5-Cl—C₆H₂ | cis | base | ≦0.04 | — |
| C₂H₅ | CH₃ | H | 2-CH₃O,4-NH₂,5-Cl—C₆H₂ | cis | H₂O | 0.01 | — |
| C₆H₅—CH₂ | H | H | 2-CH₃O,4-NH(CH₃),5-Cl—C₆H₂ | trans | base | 0.16 | — |
| 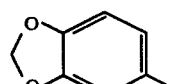 | CH₃ | H | 2-CH₃O,4-NH₂,5-Cl—C₆H₂ | cis | H₂O | <0.04 | — |
| 3-CH₃O—C₆H₄—CH₂ | CH₃ | H | 2-CH₃O,4-NH₂,5-Cl—C₆H₂ | cis | ½H₂O | <0.04 | — |
| C₆H₅—CH₂ | H | H | 2-CH₃O,4-NH(CH₃),5-Cl—C₆H₂ | cis | base | ≦0.16 | — |
| (C₆H₅)₂—C[CON(CH₃)₂]—CH₂—CH(CH₃) | H | H | 2-CH₃O,4-NH₂,5-Cl—C₆H₂ | cis | base | 0.16 | 0.63 |
| (4-F—C₆H₄)CH—(CH₂)₃ | CH₃ | H | 2-CH₃O,4-NH₂,5-Cl—C₆H₂ | trans | (COOH)₂ | 0.16 | — |
| 4-F—C₆H₄—O—(CH₂)₃ | CH₃ | H | 2-CH₃O,4-NH₂,5-Cl—C₆H₂ | cis | H₂O | 0.00016 | 0.31 |
| 4-F—C₆H₄—O—(CH₂)₂ | CH₃ | H | 2-CH₃O,4-NH₂,5-Cl—C₆H₂ | cis | base | 0.01 | 0.63 |
| 4-F—C₆H₄—O—(CH₂)₄ | CH₃ | H | 2-CH₃O,4-NH₂,5-Cl—C₆H₂ | cis | base | 0.01 | 0.31 |
| 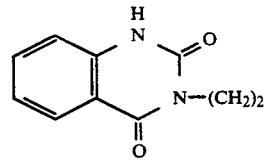 | CH₃ | H | 2-CH₃O,4-NH₂,5-Cl—C₆H₂ | cis | base | 0.0025 | 2.5 |
| 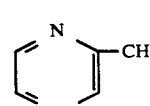 | CH₃ | H | 2-CH₃O,4-NH₂,5-Cl—C₆H₂ | cis | base | 0.04 | 1.25 |
| (4-F,2-CH₃CO—C₆H₃)—O—(CH₂)₃ | CH₃ | H | 2-CH₃O,4-NH₂,5-Cl—C₆H₂ | cis | H₂O | <0.16 | — |
| C₆H₅—O—CH(CH₃)—CH₂ | CH₃ | H | 2-CH₃O,4-NH₂,5-Cl—C₆H₂ | cis | H₂O | 0.00063 | 1.25 |
| 4-F—C₆H₄—O—(CH₂)₃ | H | H | 2-CH₃O,4-NH₂,5-Cl—C₆H₂ | cis | base | 0.0025 | ≦0.63 |
| (4-F—C₆H₄)₂C(COOC₂H₅)—(CH₂)₃ | CH₃ | H | 2-CH₃O,4-NH₂,5-Cl—C₆H₂ | cis | H₂O | 0.16 | — |
| (4-F—C₆H₄)₂C(CN)—(CH₂)₃ | CH₃ | H | 2-CH₃O,4-NH₂,5-Cl—C₆H₂ | cis | H₂O | 0.04 | — |
| 4-F—C₆H₄—SO₂—(CH₂)₃ | CH₃ | H | 2-CH₃O,4-NH₂,5-Cl—C₆H₂ | cis | base | 0.00063 | — |
| 4-F—C₆H₄—S—(CH₂)₃ | CH₃ | H | 2-CH₃O,4-NH₂,5-Cl—C₆H₂ | cis | base | 0.01 | 0.31 |
| 2,6-(CH₃)₂—C₆H₃—NHCOCH₂ | CH₃ | H | 2-CH₃O,4-NH₂,5-Cl—C₆H₂ | cis | base | 0.04 | — |
| 4-F—C₆H₄—O—(CH₂)₃ | C₂H₅ | H | 2-CH₃O,4-NH₂,5-Cl—C₆H₂ | cis | ½H₂O | 0.01 | — |
| 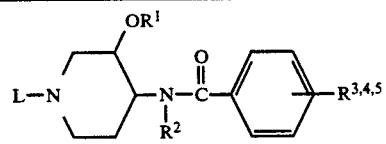 | C₂H₅ | H | 2-CH₃O,4-NH₂,5-Cl—C₆H₂ | cis | base | 0.01 | — |
| 4-F—C₆H₄—CH=CH—CH₂—CH₂ | CH₃ | H | 2-CH₃O,4-NH₂,5-Cl—C₆H₂ | cis | H₂O | 0.01 | — |

$$L-N\overset{OR^1}{\underset{}{\bigcirc}}\overset{O}{\underset{R^2}{N-C}}-\overset{}{\bigcirc}-R^{3,4,5}$$

| L | R¹ | R² | R³,⁴,⁵ | isomerism | salt form | column 1 low.effective conc. mg/l | column 2 low.effective conc. mg/l |
|---|---|---|---|---|---|---|---|
| (2-pyridinyl)CH₂ | H | H | 2-OMe,4-NH₂,5-Cl | cis | base | 0.0025 | — |
| (2,3-dihydro-1H-inden-2-yl) | CH₃ | H | 2-OMe,4-NH₂,5-Cl | cis | base | 0.16 | — |
| (1H-indol-3-yl)CH₂CH₂ | CH₃ | H | 2-OMe,4-NH₂,5-Cl | cis | H₂O | 0.01 | ≦0.63 |

TABLE 1-continued

| compound | | | | iso-merism | base salt form | column 1 low effective conc. mg/l | column 2 low effective conc. mg/l |
|---|---|---|---|---|---|---|---|
| 4-F,2-NO$_2$—C$_6$H$_3$—O(CH$_2$)$_3$ | CH$_3$ | H | 2-OMe,4-NH$_2$,5-Cl | cis | H$_2$O | 0.01 | 0.31 |
| 4-F,2-NH$_2$—C$_6$H$_3$—O(CH$_2$)$_3$ | CH$_3$ | H | 2-OMe,4-NH$_2$,5-Cl | cis | base | 0.16 | — |
| 4-F—C$_6$H$_4$—O(CH$_2$)$_2$CH(CH$_3$) | CH$_3$ | H | 2-OMe,4-NH$_2$,5-Cl | cis | base | 0.16 | 0.31 |
| (4,5,6,7-tetrahydro-1H-benzimidazol-2-yl)CH$_2$ | CH$_3$ | H | 2-OMe,4-NH$_2$,5-Cl | cis | base | 0.16 | — |
| 4-F—C$_6$H$_4$—O—CH$_2$CH$_2$CH$_2$ | COCH$_3$ | H | 2-OMe,4-NH$_2$,5-Cl | cis | base | 0.16 | — |
| (5-Me-1H-imidazol-4-yl)CH$_2$ | CH$_3$ | H | 2-OMe,4-NH$_2$,5-Cl | cis | H$_2$O | 0.16 | — |
| [4-F,2-(4-F—C$_6$H$_4$CO)C$_6$H$_3$]—OCH$_2$CH$_2$CH$_2$ | CH$_3$ | H | 2-OMe,4-NH$_2$,5-Cl | cis | base | 0.16 | — |
| 4-F—C$_6$H$_4$—O—CH$_2$CH$_2$CH$_2$ | CH$_3$ | H | 2-OMe,4-NH$_2$,5-Br | cis | H$_2$O | 0.01 | — |
| (2-pyridinyl)CH$_2$ | COCH$_3$ | H | 2-OMe,4-NHAc,5-Cl | cis | base | 0.16 | — |
| (2-pyridinyl)CH$_2$ | COCH$_3$ | H | 2-OMe,4-NH$_2$,5-Cl | cis | base | 0.16 | 0.63 |
| (4-F—C$_6$H$_4$)OCH$_2$CH(OH)CH$_2$ | CH$_3$ | H | 2-OMe,4-NH$_2$,5-Cl | cis | base | 0.01 | — |
| C$_6$H$_5$—NH—CH$_2$CH$_2$ | CH$_3$ | H | 2-OMe,4-NH$_2$,5-Cl | cis | H$_2$O | 0.00063 | — |
| 4-F,2-NH$_2$CO—C$_6$H$_3$O(CH$_2$)$_3$ | CH$_3$ | H | 2-OMe,4-NH$_2$,5-Cl | cis | base | 0.00016 | — |
| (C$_6$H$_5$)$_2$C(CONMe$_2$)CH$_2$CH$_2$ | CH$_3$ | H | 2-OMe,4-NH$_2$,5-Cl | cis | H$_2$O | 0.16 | — |
| C$_6$H$_5$CH$_2$N(Me)CH$_2$CH(OH)CH$_2$ | CH$_3$ | H | 2-OMe,4-NH$_2$,5-Cl | cis | (COOH)$_2$ H$_2$O | 0.16 | — |
| (4-F—C$_6$H$_4$)CH(2-thienyl)(CH$_2$)$_3$ | CH$_3$ | H | 2-OMe,4-NH$_2$,5-Cl | cis | H$_2$O | 0.01 | 0.16 |
| 2-COCH$_3$—C$_6$H$_4$—O—(CH$_2$)$_3$ | CH$_3$ | H | 2-OMe,4-NH$_2$,5-Cl | cis | H$_2$O | 0.01 | — |
| 2-COCH$_3$—C$_6$H$_4$—O—(CH$_2$)$_3$ | CH$_3$ | H | 2-OMe,4-NH$_2$,5-Cl | cis | H$_2$O | 0.16 | — |
| 2-OH,4-F—C$_6$H$_3$CO(CH$_2$)$_3$ | CH$_3$ | H | 2-OMe,4-NH$_2$,5-Cl | cis | HCl | 0.00063 | — |
| Et$_3$N—CH$_2$CH$_2$ | CH$_3$ | H | 2-OMe,4-NH$_2$,5-Cl | cis | 2H$_2$O | 0.16 | 0.63 |
| 4-F—C$_6$H$_4$—(CH$_2$)$_4$ | CH$_3$ | H | 2-OMe,4-NH$_2$,5-Cl | cis | H$_2$O | 0.01 | — |
| CH$_3$CO(CH$_2$)$_3$ | CH$_3$ | H | 2-OMe,4-NH$_2$,5-Cl | cis | H$_2$O | 0.01 | — |
| (4-F—C$_6$H$_4$)—O—(CH$_2$)$_3$ | CH$_3$ | H | H,H,H | trans | base | 0.16 | — |
| H | CH$_3$ | H | 2-OMe,4-NH$_2$,5-CONH$_2$ | cis | ½H$_2$O | 0.16 | — |
| 4-Cl,2-Me—C$_6$H$_3$O—(CH$_2$)$_3$ | CH$_3$ | H | 2-OMe,4-NH$_2$,5-Cl | cis | H$_2$O | 0.16 | — |
| 3-CF$_3$—C$_6$H$_4$—O—(CH$_2$)$_3$ | CH$_3$ | H | 2-OMe,4-NH$_2$,5-Cl | cis | base | 0.16 | — |
| 4-F—C$_6$H$_4$—O—(CH$_2$)$_3$ | CH$_3$ | H | 2-OMe,4-NH$_2$,5-Cl | cis+ | base | 0.01 | 0.63 |
| 4-F—C$_6$H$_4$—O—(CH$_2$)$_3$ | CH$_3$ | H | 2-OMe,4-NH$_2$,5-Cl | cis− | base | 0.04 | 0.16 |
| 4-NO$_2$—C$_6$H$_4$—O—(CH$_2$)$_3$ | CH$_3$ | H | 2-OMe,4-NH$_2$,5-Cl | cis | base | 0.01 | <0.63 |
| 4-NH$_2$—C$_6$H$_4$—O—(CH$_2$)$_3$ | CH$_3$ | H | 2-OMe,4-NH$_2$,5-Cl | cis | base | 0.0063 | — |
| 4-F—C$_6$H$_4$—O—(CH$_2$)$_5$ | CH$_3$ | H | 2-OMe,4-NH$_2$,5-Cl | cis | H$_2$O | 0.01 | 0.31 |
| (C$_6$H$_5$)$_2$N—(CH$_2$)$_3$ | CH$_3$ | H | 2-OMe,4-NH$_2$,5-Cl | cis | H$_2$O | 0.16 | 0.16 |
| (4-F—C$_6$H$_4$)O(CH$_2$)$_6$ | CH$_3$ | H | 2-OMe,4-NH$_2$,5-Cl | cis | H$_2$O | 0.00063 | 0.16 |
| C$_6$H$_5$—O—(CH$_2$)$_3$ | CH$_3$ | H | 2-OMe,4-NH$_2$,5-Cl | cis | HCl | 0.01 | 0.63 |
| (4-F—C$_6$H$_4$)$_2$CH—O—CH$_2$CH$_2$ | CH$_3$ | H | 2-OMe,4-NH$_2$,5-Cl | cis | H$_2$O | 0.01 | 0.16 |
| 4-F—C$_6$H$_4$—O—(CH$_2$)$_3$ | CH$_3$ | H | 2-OMe,4-NHAc,5-Cl | cis | base | 0.16 | — |
| (C$_6$H$_5$)$_2$N—CO—CH$_2$CH$_2$ | CH$_3$ | H | 2-OMe,4-NH$_2$,5-Cl | cis | H$_2$O | 0.16 | — |
| 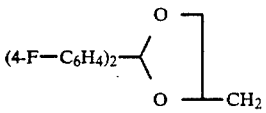 | CH$_3$ | H | 2-OMe,4-NH$_2$,5-Cl | cis | base | 0.16 | ≦0.63 |
| 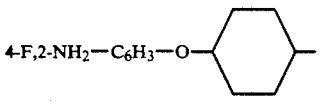 | CH$_3$ | H | 2-OMe,4-NH$_2$,5-Cl | cis | base | 0.01 | 0.63 |
| MeO—(CH$_2$)$_3$ | CH$_3$ | H | 2-OMe,4-NH$_2$,5-Cl | cis | base | 0.01 | — |
| 4-F—C$_6$H$_4$—O—CH$_2$CH(CH$_3$)CH$_2$ | CH$_3$ | H | 2-OMe,4-NH$_2$,5-Cl | cis | base | 0.016 | 0.16 |
| (C$_6$H$_5$)$_2$CH—CO—(CH$_2$)$_3$ | CH$_3$ | H | 2-OMe,4-NH$_2$,5-Cl | cis | base | 0.16 | — |
| [1-(4-F—C$_6$H$_4$)-1,3-dihydro-1-isobenzofuranyl]-(CH$_2$)$_3$ | CH$_3$ | H | 2-OMe,4-NH$_2$,5-Cl | cis | base | 0.01 | — |
| 4-F—C$_6$H$_4$—C(OMe)$_2$—CH(OH)CH$_2$CH$_2$ | CH$_3$ | H | 2-OMe,4-NH$_2$,5-Cl | cis | base | 0.00063 | — |
| 4-F—C$_6$H$_4$—CO—CH(OH)CH$_2$CH$_2$ | CH$_3$ | H | 2-OMe,4-NH$_2$,5-Cl | cis | base | 0.00063 | — |
| 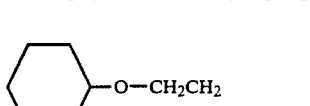 | CH$_3$ | H | 2-OMe,4-NH$_2$,5-Cl | cis | base | 0.01 | — |

TABLE 1-continued

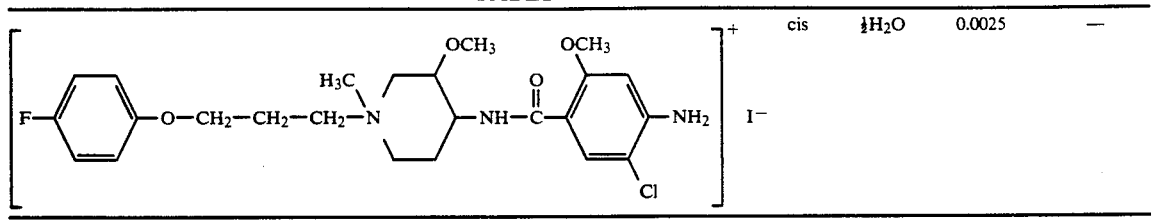

| | | | | cis | ½H₂O | 0.0025 | — |

TABLE 2

| L | iso-merism | base/salt form | minimal effective dose in mg/kg body weight when administered | |
|---|---|---|---|---|
| | | | orally | intravenously |
| (N-CH₂ pyridylmethyl) | cis | base | ≦0.31 | ≦0.08 |
| 4-F—C₆H₄—O—(CH₂)₃ | cis | H₂O | ≦0.31 | ≦0.08 |

In view of their activity to stimulate the motility of the gastro-intestinal system the subject compounds are useful to normalize or to improve the gastric and intestinal emptying in subjects suffering from a decreased peristalsis of the stomach and/or the small and/or the large intestines.

In view of their useful activity to stimulate the motility of the gastro-intestinal system the subject compounds may be formulated into various pharmaceutical forms for administration purposes. To prepare the pharmaceutical compositions of this invention an effective amount of the particular compound or compounds, in base or acid-addition salt form, as the active ingredients, is combined in intimate admixture with a pharmaceutically acceptable carrier, which carrier may take a wide variety of forms depending on the form of preparation desired for administration, said amount being an amount which is effective to stimulate the motility of the gastro-intestinal system.

These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are abviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier.

Examples of such dosage unit forms are tablets (including scored or coated tablets), capsules, pills, powder packets, wafers, injectable solutions or suspensions, teaspoonfuls, tablespoonfuls and the like, and segregated multiples thereof.

The amount of active ingredient per dosage unit will be from about 0.25 mg to about 100 mg and, preferably from about 1 to about 50 mg.

The following formulations exemplify compositions typical for the stimulation of the motility of the gastrointestinal system in dosage unit form suitable for systemic administration to animal and human subjects in accordance with the instant invention.

Oral Drops

The following formulation provides 50 liters of an oral-drop solution comprising 10 milligrams of cis-4-amino-5-chloro-N-[1-[3-(4-fluorophenoxy)propyl]-3-methoxy-4-piperidinyl]-2-methoxybenzamide as the active ingredient (A.I.) per milliliter.

| A.I. | 500 grams |
|---|---|
| 2-hydroxypropanoic acid | 0.5 liter |
| Sodium saccharin | 1750 grams |
| Cocoa flavor | 2.5 liters |
| Purified water | 2.5 liters |
| Polyethylene glycol q.s. ad | 50 liters |

The A.I. was dissolved in the 2-hydroxypropanoic acid and 1.5 liters of the polyethylene glycol at 60°-80° C. After cooling to 30°-40° C. there were added 35 liters of polyethylene glycol and the mixture was stirred well. Then there was added a solution of the sodium saccharin in 2.5 liters of purified water and while stirring there were added the cocoa flavor and polyethylene glycol q.s. ad volume. The resulting solution was filled into suitable containers.

Injectable Solution

The following formulation provides 20 liters of a parenteral solution comprising 2 milligrams of cis-4-amino-5-chloro-N-[1-[3-(4-fluorophenoxy)-propyl]-3-methoxy-4-piperidinyl]-2-methoxybenzamide as the active ingredient per milliliter.

| | |
|---|---|
| A.I. | 40 grams |
| 2,3-dihydroxybutanedioic acid | 20 grams |
| methyl 4-hydroxybenzoate | 36 grams |
| propyl 4-hydroxybenzoate | 4 grams |
| water for injection q.s. ad | 20 liters. |

The methyl and propyl 4-hydroxybenzoates were dissolved in about 10 liters of boiling water for injection. After cooling to about 50° C. there were added while stirring the 2,3-dihydroxybutanedioic acid and thereafter the A.I.. The solution was cooled to room temperature and supplemented with water for injection q.s. ad volume. The solution was sterilized by filtration (U.S.P. XVII p. 811) and filled in sterile containers.

Oral Solution

The following formulation provides 20 liters of an oral solution comprising 5 milligrams of cis-4-amino-5-chloro-N-[1-[3-(4-fluorophenoxy)propyl]-3-methoxy-4-piperidinyl]-2-methoxybenzamide as the active ingredient per teaspoonful (5 milliliters).

| | |
|---|---|
| A.I. | 20 grams |
| 2,3-dihydroxybutanedioic acid | 10 grams |
| Sodium saccharin | 40 grams |
| 1,2,3-propanetriol | 12 liters |
| Sorbitol 70% solution | 3 liters |
| Methyl 4-hydroxybenzoate | 9 grams |
| Propyl 4-hydroxybenzoate | 1 gram |
| Raspberry essence | 2 milliliters |
| Gooseberry essence | 2 milliliters |
| Purified water q.s. ad | 20 liters. |

The methyl and propyl 4-hydroxybenzoates were dissolved in 4 liters of boiling purified water. In 3 liters of this solution were dissolved first the 2,3-dihydroxybutanedioic acid and thereafter the A.I.. The latter solution was combined with the remaining part of the former solution and the 1,2,3-propanetriol and the sorbitol solution were added thereto. The sodium saccharin was dissolved in 0.5 liters of water and the raspberry and gooseberry essences were added. The latter solution was combined with the former, water was added q.s. ad volume and the resulting solution was filled in suitable containers.

Film-Coated Tablets 10,000 Compressed tablets, each containing as the active ingredient 10 milligrams of cis-4-amino-5-chloro-N-[1-[3-(4-fluorophenoxy)propyl]-3-methoxy-4-piperidinyl]-2-methoxybenzamide, were prepared from the following formulation:

| | |
|---|---|
| Tablet core: | |
| A.I. | 100 grams |
| Lactose | 570 grams |
| Starch | 200 grams |
| Polyvinylpyrrolidone (Kollidon K 90) | 10 grams |
| Microcrystalline cellulose (Avicel) | 100 grams |
| Sodium dodecyl sulfate | 5 grams |
| Hydrogenated vegetable oil (Sterotex) | 15 grams |
| Coating: | |
| Methyl cellulose (Methocel 60 HG) | 10 grams |
| Ethyl cellulose (Ethocel 22 cps) | 5 grams |
| 1,2,3-propanetriol | 2.5 milliliters |
| Polyethylene glycol 6000 | 10 grams |
| Concentrated colour suspension (Opaspray K-1-2109) | 30 milliliters |
| Polyvinylpyrrolidone (Povidone) | 5 grams |
| Magnesium octadecanoate | 2.5 grams |

Preparation of Tablet Core

A mixture of the A.I., the lactose and the starch was mixed well and thereafter humidified with a solution of the sodium dodecyl sulfate and the polyvinylpyrrolidone in about 200 milliliters of water. The wet powder was sieved, dried and sieved again. Then there was added the microcrystalline cellulose and the hydrogenated vegetable oil. The whole was mixed well and compressed into tablets.

Coating

To a solution of the methyl cellulose in 75 milliliters of denaturated ethanol there was added a solution of the ethyl cellulose in 150 milliliters of dichloromethane. Then there were added 75 milliliters of dichloromethane and the 1,2,3-propanetriol. The polyethylene glycol was molten and dissolved in 75 milliliters of dichloromethane. The latter solution was added to the former and then there were added the magnesium octadecanoate, the polyvinylpyrrolidone and the concentrated colour suspension and the whole was homogenised.

The tablet cores were coated with the thus obtained mixture in a coating apparatus.

Suppositories

Hundred suppositories each containing 30 milligrams cis-4-amino-5-chloro-N-[1-[3-(4-fluorophenoxy)-propyl]-3-methoxy-4-piperidinyl]-2-methoxybenzamide as the active ingredient were prepared from the following formulations:

| | |
|---|---|
| A.I. | 3 grams |
| 2,3-dihydroxybutanedioic acid | 3 grams |
| Polyethylene glycol 400 | 25 milliliters |
| Surfactant (Span) | 12 grams |
| Triglycerides (Witepsol 555) q.s. ad | 300 grams. |

The A.I. was dissolved in a solution of the 2,3-dihydroxybutanedioic acid in polyethylene glycol 400. The surfactant and the triglycerides were molten together. The latter mixture was mixed well with the former solution. The thus obtained mixture was poured into moulds at a temperature of 37°-38° C. to form the suppositories.

In view of the activity of the subject compounds to stimulate the motility of the gastro-intestinal system, it is evident that the present invention provides a method of stimulating the motility of the gastro-intestinal system in vertebrates by the systemic administration of an effective amount of at least one compound of formula (I), an acid addition salt or a stereochemically isomeric form thereof in admixture with a pharmaceutical carrier, said amount being effective to stimulate the motility of the gastro-intestinal system.

Due to their gastro-intestinal motility stimulating activity the subject compounds may be useful in diagnostic and therapeutic applications when modifications of the gastro-intestinal motility are required such as, for example, an improved peristalsis of the esophagus, the stomach, the small and large intestines and the normalization of the tonus of the sphincters in this system without effects on the systemic autonomic system. Illustrative examples are the improved gastric emptying and the enhanced intestinal transit time.

The following examples are intended to illustrate and not to limit the scope of the present invention. Unless otherwise stated all parts therein are by weight.

EXAMPLES

A) Preparation of Intermediates

EXAMPLE I

To a stirred and cooled (2-propanone/$CO_2$-bath)-Grignard complex previously prepared starting from 254.1 parts of 3-bromo-1-propene, 54.7 parts of magnesium and 1540 parts of anhydrous 1,1'-oxybisethane was added dropwise, during a 1 hour-period, a solution of 330 parts of cyclopropyl (4-fluorophenyl)methanone in 280 parts of anhydrous 1,1'-oxybisethane at a temperature below $-5°$ C. The reaction mixture was allowed to reach room temperature and stirring was continued overnight at room temperature. The mixture was cooled to 0° C. and decomposed with 350 parts of a saturated ammonium chloride solution. The 1,1'-oxybisethane was decanted and the residual salts were suspended twice in 140 parts of 1,1'-oxybisethane. The latter was decanted and the combined 1,1'-oxybisethane-phases were washed with 500 parts of water.

The organic phase was dried, filtered and evaporated. From the residue, the forerun was distilled off by "Spinning Band". The distillation residue yielded 255.7 parts (62%) of α-cyclopropyl-4-fluoro-α-(2-propenyl)benzenemethanol (intermediate 1).

Following the same Grignard procedure and starting from the appropriate ketones or aldehydes there were also prepared:

4-fluoro-α-(2-propenyl)benzenemethanol; bp. 75°–80° C. at 1 mm. pressure (intermediate 2); and
4-fluoro-α-methyl-α-(2-propenyl)benzenemethanol (intermediate 3).

EXAMPLE II

30 Parts of a sodium hydride dispersion 50% were suspended twice in petroleumether and the latter was decanted each time. To the residue were added 432 parts of N,N-dimethylformamide. Then there was added dropwise a solution of 123.6 parts of α-cyclopropyl-4-fluoro-α-(2-propenyl)benzenemethanol in 216 parts of N,N-dimethylformamide at 50° C. while nitrogen gas was introduced. The mixture was allowed to cool to room temperature and 89.4 parts of iodomethane were added dropwise under nitrogen atmosphere: exothermic reaction (cooling in an ice-bath to 20° C.). Upon completion, stirring was continued for 1 hour at room temperature. The reaction mixture was poured onto 2000 parts of ice-water and the product was extracted with 1,1'-oxybisethane. The extract was washed with water, dried, filtered and evaporated. The oily residue was distilled, yielding 100.1 parts (75.8%) of 1-(1-cyclopropyl-1-methoxy-3-butenyl)-4-fluorobenzene; bp. 110°–114° C. at 2 mm. pressure (intermediate 4).

In a similar manner there were also prepared:
1-fluoro-4-(1-methoxy-3-butenyl)benzene; bp. 145° C. at 7 mm. pressure (intermediate 5); and
1-fluoro-4-(1-methoxy-1-methyl-3-butenyl)benzene; bp. 48° C. at 1 mm. pressure (intermediate 6).

EXAMPLE III

To a stirred mixture of 100.6 parts of 1-(1-cyclopropyl-1-methoxy-3-butenyl)-4-fluorobenzene and 238 parts of dichloromethane was added a solution of 101.5 parts of 3-chlorobenzeneperoxoic acid in 952 parts of dichloromethane (exothermic reaction after 30 minutes). The whole was stirred overnight at room temperature. The precipitate was filtered off and the filtrate was washed successively with a saturate sodium carbonate solution, a saturate sodium sulfite solution, a 5% sodium hydroxide solution and water. The organic phase was dried, filtered and evaporated, yielding 106 parts of [2-cyclopropyl-2-(4-fluorophenyl)-2-methoxyethyl]oxirane as a residue (intermediate 7).

Following the same epoxidizing procedure there were also prepared:
[2-(4-fluorophenyl)-2-methoxyethyl]oxirane as a residue (intermediate 8);
[2-(4-fluorophenyl)-2-methoxypropyl]oxirane as a residue (intermediate 9);
α-cyclopropyl-α-(4-fluorophenyl)oxiraneethanol as an oily residue (intermediate 10); and
α-(4-fluorophenyl)oxiraneethanol as a residue (intermediate 11).

EXAMPLE IV

A mixture of 15 parts of methyl 2-amino-4-pyridinecarboxylate, 13.75 parts of 1-chloro-2-propanone and 160 parts of absolute methanol was stirred and refluxed for 18 hours. The reaction mixture was treated with a sodium hydroxide solution 1N in methanol. The solvent was evaporated in vacuo and the residue was dissolved in trichloromethane. The solution was filtered and the filtrate was evaporated. The residue was purified by column-chromatography over silica gel using a mixture of trichloromethane and methanol (98:2 by volume) as eluent. The pure fractions were collected and the eluent was evaporated. The residue was crystallized from 4-methyl-2-pentanone. The product was filtered off, washed with 2,2'-oxybispropane and dried, yielding 9.7 parts of methyl 2-methylimidazo[1,2-a]pyridine-7-carboxylate; mp. 149.1° C. (intermediate 12).

EXAMPLE V

A mixture of 1.31 parts of 2-bromo-1,1-diethoxyethane, 10 parts of water and 1.5 parts of a hydrobromic acid solution 48% in water was stirred and refluxed for 1 hours. The mixture was poured onto 50 parts of water and the whole was neutralized with potassium carbonate. Then there were added successively 5 parts of sodium hydrogen carbonate and 3 parts of methyl 2-amino-4-pyridinecarboxylate. The reaction mixture was stirred and heated for 15 minutes at 55° C. in an oil-bath. After 30 minutes, gas-evolution had ceased and the mixture was cooled. The product was extracted with dichloromethane. The extract was dried, filtered and evaporated. The residue was stirred in 2,2'-oxybispropane. The product was filtered off and dried, yielding 2.9 parts (82.3%) of methyl imidazo-[1,2-a]pyridine-7-carboxylate; mp. 143.2° C. (intermediate 13).

EXAMPLE VI

A mixture of 5.1 parts of lithium iodide dihydrate and 40 parts of acetonitrile was stirred till all solid enters solution. Then there were added successively 1.5 parts of sodium borohydride and 3.8 parts of methyl 2-methylimidazo[1,2-a]pyridine-7-carboxylate and the whole was stirred and refluxed for 3 hours. The solvent was evaporated and the residue was stirred in 100 parts of water. The mixture was acidified with concentrated hydrochloric acid and the whole was stirred and refluxed for 30 minutes. After cooling, the mixture was alkalized with ammonium hydroxide and salted out with potassium carbonate. The product was extracted with dichloromethane. The extract was dried, filtered and evaporated. The residue was converted into the hydrochloride salt in 40 parts of 2-propanone. The salt was filtered off and dried, yielding 2.4 parts (60.4%) of 2-methylimidazo[1,2-a]-pyridine-7-methanol monohydrochloride; mp. 213.6° C. (intermediate 14).

In a similar manner there was also prepared:
imidazo[1,2-a]pyridine-7-methanol monohydrochloride; mp. 199.7° C. (intermediate 15).

EXAMPLE VII

To a stirred mixture of 10.7 parts of 2-methylimidazo[1,2-a]pyridine-7-methanol monohydrochloride and 150 parts of trichloromethane were added dropwise 9.6 parts of thionyl chloride. The resulting solution was stirred for 15 minutes at room temperature. The reaction mixture was evaporated in vacuo and the residue was stirred in 80 parts of 2-propanone. The product was filtered off, washed with 2,2'-oxybispropane and dried, yielding 11.8 parts (100%) of 7-(chloromethyl)-2-methylimidazo-[1,2-a]pyridine monohydrochloride; mp. 178.5 (intermediate 16).

In a similar manner there was also prepared:
7-(chloromethyl)imidazo[1,2-a]pyridine monohydrochloride; mp. 158.6° C. (intermediate 17).

EXAMPLE VIII

A mixture of 13.6 parts of 1H-imidazole, 16.8 parts of ethyl 4-fluorobenzoate, 0.1 parts of potassium iodide and 54 parts of N,N-dimethylacetamide was stirred and refluxed for 20 hours. The reaction mixture was cooled to room temperature and poured onto a lot of water. The product was extracted a few times with benzene. The combined extracts were washed thoroughly with water, dried, filtered and evaporated. The residue was stirred in hexane. The product was filtered off and dried, yielding 7.2 parts (33.3%) of ethyl 4-(1H-imidazol-1-yl)benzoate; mp. 100.3° C. (intermediate 18).

To 90 parts of tetrahydrofuran were added 5 parts of lithium aluminum hydride. Then there was added dropwise (slowly) a solution of 35 parts of ethyl 4-(1H-imidazol-1-yl)benzoate in 135 parts of tetrahydrofuran: temperature rose to 60° C. Upon completion, stirring was continued first for 1 hour at 60°–65° C. and further overnight at room temperature. While cooling, the reaction mixture was decomposed by the successive dropwise additions of 3 parts of water, 10 parts of a sodium hydroxide solution 50% and 10 parts of water. After stirring for a while at room temperature, the precipitate was filtered off and washed with benzene. The filtrate was dried, filtered and evaporated. The residue was crystallized from 4-methyl-2-pentanone. The product was filtered off, washed with 2,2'-oxybispropane and dried, yielding 16.2 parts (58%) of 4-(1H-imidazol-1-yl)-benzenemethanol; mp. 124.7° C. (intermediate 19).

A stirred solution of 11.3 parts of 4-(1H-imidazol-1-yl)benzenemethanol in 375 parts of trichloromethane was acidified with gaseous hydrogen chloride at room temperature. Then there were added dropwise 10.6 parts of thionyl chloride at room temperature. Upon completion, stirring was continued first for 30 minutes at reflux and further for 30 minutes at room temperature. The reaction mixture was evaporated. The residue was taken up a few times in methylbenzene and the latter was evaporated each time. The residue was stirred for 1 hour in 2,2'-oxybispropane. The product was filtered off, washed with 2,2'-oxybispropane and dried in vacuo overnight, yielding 13.5 parts of 1-[4-(chloromethyl)phenyl]-1H-imidazole monohydrochloride (intermediate 20).

EXAMPLE IX

A mixture of 3 parts of α-(3-chloropropyl)-4-fluoro-α-(4-fluorophenyl)benzeneacetonitrile, 92 parts of concentrated sulfuric acid, 50 parts of water and 50 parts of acetic acid was stirred and refluxed for 24 hours. The reaction mixture was concentrated to about 100 parts and the product was extracted with methylbenzene. The extract was washed with water, dried, filtered and evaporated. The residue was suspended in petroleumether. The product was filtered off and crystallized from 2,2'-oxybispropane, yielding 1.41 parts of 3,3-bis(4-fluorophenyl)tetrahydro-2H-pyran-2-one; mp. 122.4° C. (intermediate 21).

A mixture of 5.8 parts of 3,3-bis(4-fluorophenyl)-tetrahydro-2H-pyran-2-one and 30 parts of a solution of hydrobromic acid in glacial acetic acid was stirred over week-end at room temperature. The reaction mixture was poured onto water. The precipitated product was filtered off and dissolved in 2,2'-oxybispropane. The organic phase was washed with water, dried, filtered and evaporated. The residue was boiled in a mixture of 42 parts of 2,2'-oxybispropane and 42 parts of petroleumether. The product was filtered off and crystallized from 2,2'-oxybispropane, yielding 1.27 parts of α-(3-bromopropyl)-4-fluoro-α-(4-fluorophenyl)benzeneacetic acid; mp. 161° C. (intermediate 22).

To a stirred solution of 29.5 parts of α-(3-bromopropyl)-4-fluoro-α-(4-fluorophenyl)benzeneacetic acid in 300 parts of trichloromethane were added 28.8 parts of thionyl chloride and the whole was stirred and refluxed for 3 hours. The reaction mixture was evaporated, yielding 30 parts of α-(3-bromopropyl)-4-fluoro-α-(4-fluorophenyl)-benzeneacetyl chloride as a residue.

A mixture of 30 parts of α-(3-bromopropyl)-4-fluoro-α-(4-fluorophenyl)benzeneacetyl chloride, 9.3 parts of ethanol and 90 parts of methylbenzene was stirred overnight at room temperature. The reaction mixture was evaporated, the residue was taken up in ethanol and the latter was evaporated again. The residue was taken up in 2,2'-oxybispropane. The whole was washed with a saturate sodium hydrogen carbonate solution and with water, dried, filtered and evaporated. The residue was purified by column-chromatography over silica gel using a mixture of trichloromethane and hexane (50:50 by volume) as eluent. The pure fractions were collected and the eluent was evaporated, yielding 19.6 parts of ethyl α-(3-bromopropyl)-4-fluoro-α-(4-fluorophenyl)-benzeneacetate as a residue (intermediate 23).

EXAMPLE X

To a stirred mixture of 30.4 parts of 1,3-propanediol and 90 parts of N,N-dimethylformamide were added 5.28 parts of a sodium hydride dispersion 50% at a temperature below 20° C. Stirring was continued for 2 hours at room temperature under nitrogen atmosphere. Then there were added dropwise 15.9 parts of 1,4-difluoro-2-nitrobenzene so that the temperature had been maintained below 30° C. Upon completion, stirring was continued overnight at room temperature. The reaction mixture was poured onto water and the product was extracted with trichloromethane. The extract was washed with water, dried, filtered and evaporated. The residue was purified by column-chromatography over silica gel using trichloromethane as eluent. The pure fractions were collected and the eluent was evaporated, yielding 21.5 parts 3-(4-fluoro-2-nitrophenoxy)-propanol as a residue (intermediate 24).

To a stirred mixture of 12.6 parts of 3-(4-fluoro-2-nitrophenoxy)propanol, 0.9 parts of N,N-dimethylformamide and 150 parts of trichloromethane were added dropwise 8.36 parts of thionyl chloride and stirring was continued for 1 hour at room temperature. The whole was further stirred and refluxed for 3 hours. The reaction mixture was evaporated under methylbenzene. The residue was stirred in petroleumether. The product was filtered off and dried, yielding 7.41 parts (55%) of 1-(3-chloropropoxy)-4-fluoro-2-nitrobenzene; mp. 143.3° C. (intermediate 25).

EXAMPLE XI

To a stirred solution of 134 parts of 4-fluorophenol and 2 parts of 4-methylbenzenesulfonic acid in 1080 parts of benzene were added 42 parts of 3-buten-2-one. Stirring was continued for 4 days at room temperature. 700 Parts of 1,1'-oxybisethane were added and the whole was washed four times with 500 parts of a cold sodium hydroxide solution 1N and with water. The organic phase was dried, filtered and evaporated. The oily residue was purified by column-chromatography over silica gel using trichloromethane as eluent. The pure fractions were collected and the eluent was evaporated. The oily residue solidified upon cooling. The product was suspended in cold petroleumether. The product was filtered off and dried at room temperature, yielding 43.4 parts (39.7%) of 4-(4-fluorophenoxy)-2-butanone (intermediate 26).

To a stirred mixture of 37.6 parts of 4-(4-fluorophenoxy)-2-butanone and 400 parts of ethanol were added portionwise 21.2 parts of sodium borohydride at a temperature below 20° C. Upon completion, stirring was continued for 1 hour at room temperature. The reaction mixture was concentrated to half its volume. After cooling, 500 parts of water were added and evaporation was continued till all ethanol was removed. After cooling, the product was extracted with 1,1'-oxybisethane. The extract was washed with water, dried, filtered and evaporated. The oily residue was distilled, yielding 20.80 parts (55.1%) of 4-(4-fluorophenoxy)-2-butanol; bp. 140°–141° C. (water-jet) (intermediate 27).

To a stirred and cooled mixture of 10 parts of 4-(4-fluorophenoxy)-2-butanol and 30 parts of pyridine were added portionwise 7.4 parts of methanesulfonyl chloride at a temperature below 10° C. Upon completion, stirring was continued for 1 hour at room temperature. The reaction mixture was allowed to stand overnight in an ice-box. Then it was poured onto water and the product was extracted with dichloromethane. The extract was washed with a cold hydrochloric acid solution 20% and with water, dried, filtered and evaporated. The oily residue was purified by column-chromatography over silica gel using a mixture of trichloromethane and methanol (95:5 by volume) as eluent. The pure fractions were collected and the eluent was evaporated, yielding 10 parts (64%) of 4-(4-fluorophenoxy)-2-butanol methanesulfonate (ester) as an oily residue (intermediate 28).

EXAMPLE XII

A mixture of 9.3 parts of 5-chloro-1,3-dihydro-1-(3-hydroxypropyl)-2H-benzimidazol-2-one and 83 parts of a hydrobromic acid solution 48% in water was stirred and refluxed for 6 hours. The reaction mixture was cooled and allowed to crystallize overnight at room temperature. The precipitated product was filtered off and stirred a few times in 100 parts of water till the pH of the filtrate was greater than 2. The product was stirred and refluxed for 1 hour in 55 parts of chlorobenzene with 1.3 parts of activated charcoal. The latter was filtered off and the filtrate was allowed to crystallize overnight in an ice-box. The product was filtered off and recrystallized twice: first from chlorobenzene (activated charcoal) and then from methylbenzene (activated charcoal), yielding 4.9 parts of 1-(3-bromopropyl)-5-chloro-1,3-dihydro-2H-benzimidazol-2-one; mp. 161.5° C. (intermediate 29).

EXAMPLE XIII

To a stirred (vigourously) mixture of 17.4 parts of 2-chloroethanamine hydrochloride, 20.7 parts of potassium carbonate and 225 parts of water was added dropwise a mixture of 31.3 parts of 2,6-dichlorobenzoyl chloride and 120 parts of dichloromethane at room temperature: slightly exothermic reaction. Upon completion, stirring at room temperature was continued for one hour. The organic phase was separated and the aqueous phase was extracted with dichloromethane. The combined organic phases were washed with water, dried, filtered and evaporated. The residue was crystalized from methylbenzene. The product was filtered off and dried, yielding 25.8 parts (68.8%) of 2,6-dichloro-N-(2-chloroethyl)benzamide; mp. 113.8° C. (intermediate 30).

EXAMPLE XIV

To a stirred solution of 17.3 parts of 2,2-dimethyl-1,3-dioxane-4,6-dione in 130 parts of dichloromethane were added 18 parts of pyridine under nitrogen atmosphere. Then there were added dropwise, during a 20 minutes-period a solution of 35.4 parts of 1-chloro-4,4-bis(4-fluorophenyl)-1-butanone in 65 parts of dichloromethane at about 0° C. while nitrogen gas was still introduced. Upon completion, stirring was continued first for 1 hour at about 0° C. and further for 1 hour at room temperature. Dichloromethane and water were added and the layers were separated. The organic phase was washed with water, dried, filtered and evaporated. The residue was boiled in 750 parts of a mixture of acetic acid and water (1:2 by volume) for 5 hours. Methylbenzene was added. The organic phase was separated, washed with water, with a sodium hydrogen carbonate solution and again with water, dried, filtered and evaporated. The residue was purified by column-chromatography over silica gel using trichloromethane as eluent. The pure fractions were collected and the eluent was evaporated, yielding 18.5 parts of 5,5-bis(4-fluorophenyl)-2-pentanone as a residue (intermediate 31).

EXAMPLE XV

A mixture of 118.6 parts of methyl 4-(acetylamino)-2-ethoxybenzoate, 200 parts of acetic acid and 156 parts of acetic acid anhydride was stirred and heated to 50° C. After cooling to 15° C. (ice-bath) there were added dropwise 47.1 parts of fuming nitric acid 100% using a bromine funnel: an exothermic reaction occured. The temperature was kept at about 20° C. by cooling in an ice-bath. Upon completion, the temperature was allowed to rise to 40° C. and stirring was continued at this temperature for one hour. If necessary the whole was cooled with ice-water to keep the temperature at about 40° C. When the exothermic reaction was ceased, the whole was allowed to cool for one hour and was further cooled to 0° C. The reaction mixture was poured onto ice-water while stirring. Upon stirring for one hour, the precipitated product was filtered off and dissolved in 1950 parts of dichloromethane. The solution was washed twice with 500 parts of water, dried, filtered and evaporated. The residue was crystallized overnight at room temperature from 2-propanol. The product was filtered off, washed with 2,2'-oxbispropane and dried, yielding 67.6 parts (47.9%) of methyl 4-(acetylamino)-2-ethoxy-5-nitrobenzoate; mp. 110° C. (intermediate 32).

To 100 parts of a hydrochloric acid solution 6N were added 5.65 parts of methyl 4-(acetylamino)-2-ethoxy-5-nitrobenzoate and the whole was stirred and refluxed for 30 minutes. After cooling, the precipitated product was filtered off and crystallized from 80 parts of 2-propanol at 0° C. The product was filtered off and dried, yielding 1.9 parts (42.2%) of methyl 4-amino-2-ethoxy-5-nitrobenzoate; mp. 210° C.; (intermediate 33).

A mixture of 4.8 parts of methyl 4-amino-2-ethoxy-5-nitrobenzoate, 1.6 parts of sodium hydroxide and 30 parts of water was stirred and refluxed for 30 minutes. The reaction mixture was cooled and 50 parts of water were added. The whole was neutralized by the dropwise addition of glacial acetic acid. The precipitated product was filtered off and crystallized from 2-propanol at 0° C. The product was filtered off, washed with a small amount of 2,2'-oxybispropane and dried, yielding 3 parts (66.6%) of 4-amino-2-ethoxy-5-nitrobenzoic acid; mp. 230° C. (intermediate 34).

EXAMPLE XVI

A mixture of 3.4 parts of ethyl 7-oxa-3-azabicyclo[4, 1, 0]heptane-3-carboxylate, 2.1 parts of benzenemethanamine and 40 parts of ethanol was stirred and refluxed for 17 hours. Another 0.3 parts of ethyl 7-oxa-3-azabicyclo[4, 1, 0]heptane-3-carboxylate were added and stirring at reflux was continued for 4 hours. The reaction mixture was evaporated. The residue was purified by column-chromatography over silica gel using a mixture of trichloromethane and methanol (97:3 by volume) as eluent. The pure fractions were collected and the eluent was evaporated, yielding 3.4 parts (61.8%) of a mixture of ethyl trans-3-hydroxy-4-[(phenylmethyl)amino]-1-piperidinecarboxylate and ethyl trans-4-hydroxy-3-[(phenylmethyl)amino]-1-piperidinecarboxylate as an oily residue (intermediates 35 and 36).

A mixture of 62.8 parts of ethyl trans-3-hydroxy-4-[(phenylmethyl)amino]-1-piperidinecarboxylate and 400 parts of methanol was hydrogenated at normal pressure and at room temperature with 5 parts of palladium-on-charcoal catalyst 10%. After the calculated amount of hydrogen was taken up, the catalyst was filtered off and the filtrate was evaporated. The oily residue was separated by column-chromatography over silica gel: using a mixture of trichloromethane and methanol (95:5 by volume) as eluent, ethyl trans-3-amino-4-hydroxy-1-piperidinecarboxylate was obtained (intermediate 37).

Using then a mixture of trichloromethane and methanol (95:5 by volume), saturated with ammonia, as eluent an oily residue was obtained which was triturated in methylbenzene. The product was filtered off and dried, yielding 10 parts (24%) of ethyl trans-4-amino-3-hydroxy-1-piperidinecarboxylate; mp. 76.9° C. (intermediate 38).

EXAMPLE XVII

A mixture of 195.4 parts of potassium hydroxide and 1065 parts of 2-propanol was stirred and warmed till all solid entered solution. After cooling to room temperature, 97 parts of ethyl trans-3-hydroxy-4-[(phenylmethyl)amino]-1-piperidinecarboxylate were added and the whole was stirred and refluxed for 4 hours. The reaction mixture was evaporated to dry and 500 parts of water were added. The whole was concentrated to a volume of about 300 parts. After cooling to room temperature, the product was extracted with dichloromethane. The extract was washed with water, dried, filtered and evaporated. The oily residue was crystallized from acetonitrile. The product was filtered off and dried, yielding 51 parts (70.8%) of trans-4-[(phenylmethyl)amino]-3-piperidinol; mp. 136° C. (intermediate 39).

A mixture of 8.59 parts of 4-fluoro-γ-(4-fluorophenyl)benzenebutanal, 4 parts of trans-4-[(phenylmethyl)amino]-3-piperidinol, 2 parts of potassium acetate, 1 part of a solution of thiophene in ethanol 5% and 120 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated. The oily residue was dissolved in 1,1'-oxybisethane. The solution was washed with water and shaken with a hydrochloric acid solution 10%. The 1,1'-oxybisethane-phase was separated and evaporated. From the residue the free base was liberated in the conventional manner with sodium hydroxide in water. The free base was extracted with dichloromethane. The extract was dried, filtered and evaporated. The oily residue was purified by column-chromatography over silica gel using a mixture of trichloromethane and methanol (90:10 by volume) as eluent. The pure fractions were collected and the eluent was evaporated. The oily residue was converted into the hydrochloride salt in 1,1'-oxybisethane and 2-propanol. The salt was filtered off and crystallized from 2-propanol, yielding 2.67 parts of trans-1-[4,4-bis(4-fluorophenyl)butyl]-4-[(phenylmethyl)amino]-3-piperidinol dihydrochloride; mp. 231.1° C. (intermediate 40).

A mixture of 14.8 parts of trans-1-[4,4-bis(4-fluorophenyl)butyl]-4-[(phenylmethyl)amino]-3-piperidinol and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The oily residue was converted into the hydrochloride salt in methylbenzene and 2-propanol. Upon the addition of petroleumeter, the salt was precipitated. It was filtered off and dried, yielding 11.18 parts of trans-4-amino-1-[4,4-bis(4-fluorophenyl)butyl]-3-piperidinol dihydrochloride; mp. 234.2° C. (intermediate 41).

EXAMPLE XVIII

To a stirred mixture of 14.4 parts of sodium methoxide solution 30% and 80 parts of methanol were added 14 parts of 3-bromo-1-(phenylmethyl)-4-piperidinone hydrobromide and the whole was stirred for 2 hours at room temperature. The reaction mixture was evaporated. 175 Parts of 1,1'-oxybisethane were added to the residue. The mixture was washed twice with water, dried, filtered and evaporated. The solid residue was crystallized from 2-propanol at 0° C. The product was filtered off, washed with 2,2'-oxybispropane and dried, yielding 2.4 parts of 4,4-dimethoxy-1-(phenylmethyl)-3-piperidinol; mp. 90.1° C. (intermediate 42).

To a stirred mixture of 37.8 parts of 4,4-dimethoxy-1-(phenylmethyl)-3-piperidinol and 135 parts of N,N-dimethylformamide were added portionwise 4.8 parts of sodium hydride dispersion 78%. The whole was heated to 60°-70° C. and stirring was continued for 30 minutes at 50° C. After cooling to room temperature, there were added dropwise 18.9 parts of (chloromethyl)benzene (exothermic reaction: temperature roses to 37° C. ). Upon completion, stirring was continued fo 2 hours at room temperature. The reaction mixture was poured onto 500 parts of water and the product was extracted twice with 1,1'-oxybisethane. The combined extracts were washed with water, dried, filtered and evaporated. The residue was purified by column-chromatography over silica gel using a mixture of trichloromethane and methanol (98:2 by volume) as eluent. The pure fractions were collected and the eluent was evaporated. The residue was distilled, yielding 33.1 parts (64.6%) of 4,4-dimethoxy-3-(phenylmethoxy)-1-(phenylmethyl)piperidine; bp. 180°-185° C. at 0.3 mm. pressure (intermediate 43).

A mixture of 125 parts of 4,4-dimethoxy-3-(phenylmethoxy)-1-(phenylmethyl)piperidine and 3000 parts of sulfuric acid solution 1% in water was stirred and refluxed for 3 hours. The reaction mixture was cooled to room temperature and neutralized with sodium carbonate. The product was extracted three times with 280 parts of 1,1'-oxybisethane. The combined extracts were washed with 200 parts of water, dried, filtered and evaporated. The residue was taken up in benzene and the latter was evaporated again. The residue was converted into the hydrochloride salt in 2-propanol. The solvent was evaporated and the residue solidified on triturating in 4-methyl-2-pentanone while heating. The hydrochloride salt was filtered off and dried, yielding 120 parts of 3-(phenylmethoxy)-1-(phenylmethyl)-4-piperidinone hydrochloride; mp. 174.3° C. (intermediate 44).

To a stirred mixture of 29.5 parts of 3-(phenylmethoxy)-1-(phenylmethyl)-4-piperidinone, 12.4 parts of sodium carbonate, 20 parts of ethanol and 25 parts of water was added dropwise a solution of 7 parts of hydroxylamine hydrochloride in 25 parts of water (slightly exothermic reaction). Upon completion, the whole was heated to reflux and stirring was continued for 16 hours at reflux temperature. The reaction mixture was cooled and the product was extracted twice with trichloromethane. The combined extracts were washed with water, dried, filtered and evaporated. The residue was dissolved in 210 parts of 1,1'-oxybisethane and the solution was stirred with activated charcoal. The latter was filtered off and the filtrate was evaporated. The oily residue was converted into the hydrochloride salt in 2-propanol. The salt was filtered off and dried, yielding 30.7 parts of 3-(phenylmethoxy)-1-(phenylmethyl)-4-piperidinone, oxime hydrochloride; mp. 218.5° C. (intermediate 45).

A mixture of 26 parts of 3-(phenylmethoxy)-1-(phenylmethyl)-4-piperidinone, oxime in 200 parts of methanol, previously saturated with gaseous ammonia was hydrogenated at normal pressure and at room temperature with 3 parts of Raney-nickel catalyst. After the calculated amount of hydrogen was taken up, the catalyst was filtered off and the filtrate was evaporated. The residue was triturated in 2,2'-oxybispropane. The mixture was filtered and the filtrate was evaporated. The residue was converted into the hydrochloride salt in 2-propanol. The solvent was evaporated. The residue solidified on triturating in a mixture of 2-propanol and 4-methyl-2-pentanone (1:4 by volume). The product was filtered off and washed with 2,2'-oxybispropane, yielding, after drying, 18.5 parts (A+B)-3-(phenylmethoxy)-1-(phenylmethyl)-4-piperidinamine dihydrochloride hemihydrate; mp. 200° C. (intermediate 46).

EXAMPLE XIX

To a stirred mixture of 10 parts of 3-(phenylmethoxy)-1-(phenylmethyl)-4-piperidinone and 65 parts of dichloromethane were added dropwise 5 parts of ethyl carbonochloridate at room temperature. After stirring for 6.30 hours at reflux, there were added 5 parts of N,N-diethylethanamine. Upon completion, stirring at reflux was continued for 24 hours. The reaction mixture was washed successively with water, a diluted hydrochloric acid solution and again with water, dried, filtered and evaporated. The residue was purified by column-chromatography over silica gel using a mixture of trichloromethane and methanol (95:5 by volume) as eluent. The pure fractions were collected and the eluent was evaporated, yielding 8.1 parts (86.5%) of ethyl 4-oxo-3-(phenylmethoxy)-1-piperidinecarboxylate as an oily residue (intermediate 47).

To 5 parts of a solution of 2 parts of thiophene in 40 parts of ethanol, were added 135 parts of ethyl 4-oxo-3-(phenylmethoxy)-1-piperidinecarboxylate, 55 parts of benzenemethanamine and 400 parts of methanol. The whole was hydrogenated at normal pressure and at 50° C. with 8 parts of palladium-on-charcoal catalyst 10%. After the calculated amount of hydrogen was taken up, the catalyst was filtered off and the filtrate was evaporated, yielding 170 parts of ethyl cis-3-(phenylmethoxy)-4-[(phenylmethyl)amino]-1-piperidinecarboxylate as an oily residue (intermediate 48).

A mixture of 170 parts of ethyl cis-3-(phenylmethoxy)-4-[(phenylmethyl)amino]-1-piperidinecarboxylate and 400 parts of methanol was hydrogenated at normal pressure and at 80° C. with 20 parts of palladium-on-charcoal catalyst 10%. After the calculated amount of hydrogen was taken up, the catalyst was filtered off and the filtrate was evaporated. The oily residue was distilled, yielding 75 parts of ethyl cis-4-amino-3-hydroxy-1-piperidinecarboxylate; bp. 175°-185° C. at 0.4 mm. pressure. (intermediate 49).

EXAMPLE XX

A mixture of 94 parts of ethyl 4,4-dimethoxy-3-(phenylmethoxy)-1-piperidinecarboxylate and 2300 parts of a sulfuric acid solution 1% in water was stirred and refluxed for 2.50 hours. The reaction mixture was cooled and the product was extracted three times with dichloromethane. The combined extracts were washed with a small amount of water, dried, filtered and evaporated. The residue was taken up in methylbenzene and the latter was evaporated again. The residue was stirred in petroleumether. The latter was separated and the solvent was evaporated, yielding 64.9 parts of ethyl 4-oxo-3-(phenylmethoxy)-1-piperidinecarboxylate as a residue (intermediate 50).

In a similar manner there were also prepared:
3-methoxy-1-methyl-4-piperidinone ethanedioate ethanolate; mp. 90° C. (intermediate 51);
ethyl 3-methoxy-4-oxo-1-piperidinecarboxylate as an oily residue (intermediate 52); and
1-[4,4-bis(4-fluorophenyl)butyl]-3-methoxy-4-piperidinone as a residue (intermediate 53).

EXAMPLE XXI

To 2 parts of a solution of 2 parts of thiophene in 40 parts of ethanol were added 126 parts of ethyl 3-methoxy-4-oxo-1-piperidinecarboxylate, 70 parts of benzenemethanamine and 400 parts of methanol. The whole was hydrogenated at normal pressure and at room temperature with 5 parts of palladium-on-charcoal catalyst 10%. After up-take of one equivalent of hydrogen, the catalyst was filtered off and hydrogenation was continued with another 5 parts of palladium-on-charcoal catalyst 10%. After the calculated amount of hydrogen was taken up, the catalyst was filtered off and the filtrate was evaporated. The residue contained some oil drops which were separated, yielding 92.9 parts of ethyl cis-4-amino-3-methoxy-1-piperidinecarboxylate (intermediate 54).

In a similar manner there were also prepared:
cis-3-methoxy-1-methyl-N-phenyl-4-piperidinamine as an oily residue (intermediate 55); and
cis-1-[4,4-bis(4-fluorophenyl)butyl]-3-methoxy-4-piperidinamine as a residue (intermediate 56).

EXAMPLE XXII

A mixture of 4.7 parts of ethyl trans-4-amino-3-hydroxy-1-piperidinecarboxylate, 3.7 parts of 1,3-dihydroisobenzofuran-1,3-dione and 45 parts of methylbenzene was stirred and refluxed for 2 hours using a water-separator. The reaction mixture was decanted from some insoluble tar. The methylbenzene-phase was evaporated in vacuo in a boiling water-bath. The residue was boiled in 2,2'-oxybispropane. After cooling, the solvent was decanted. The remaining oil solidified on scratching in 2,2'-oxybis-propane. The product was filtered off and dissolved in dichloromethane. The solution was washed successively with a dilute hydrochloric acid solution, water, a dilute sodium hydroxide solution and again water. The organic phase was dried, filtered and evaporated in vacuo. The residue solidified on scratching in 2,2'-oxybispropane. The product was filtered off and crystallized from 2-propanol, yielding 2.12 parts of ethyl trans-4-(1,3-dihydro-1,3-dioxo-2H-isoindol-2-yl)-3-hydroxyl-1-piperidinecarboxylate; mp. 128.4° C. (intermediate 57).

EXAMPLE XXIII

To a stirred mixture of 85 parts of 4,4-dimethoxy-1-(phenylmethyl)-3-piperidinol and 480 parts of sodium hydroxide solution 60% were added 288 parts of benzene and 0.5 parts of N,N,N-triethylbenzenemethanaminium chloride. Then there were added dropwise 49.2 parts of dimethyl sulfate at a temperature below 30° C. After stirring overnight at room temperature, there was added another portion of 13.3 parts of dimethyl sulfate and stirring was continued for 4 hours at room temperature. The reaction mixture was cooled, 640 parts of water were added and the layers were separated. The aqueous phase was extracted with benzene. The formed suspension was filtered and the filter-cake was set aside. The combined organic phases were washed with water, dried, filtered and evaporated. The oily residue was distilled (bp. 138° C. at 1 mm. pressure). The distillate was converted into the ethanedioate salt in 2-propanol. The salt was filtered off and crystallized from ethanol, yielding 34.9 parts of 3,4,4-trimethoxy-1-(phenylmethyl)piperidine ethanediote; mp. 180.6° C. (intermediate 58).

The filter-cake, which was set aside (see above), was dissolved in trichloromethane. The solution was washed with a small amount of water, dried, filtered and evaporated. The residue was crystallized from 2-propanol, yielding 22.3 parts of 3,4,4-trimethoxy-1-methyl-1-(phenylmethyl)piperidinium methylsulfate; mp. 170.1° C. (intermediate 59).

EXAMPLE XXIV

A mixture of 38.1 parts of 3,4,4-trimethoxy-1-(phenylmethyl)piperidine and 1200 parts of sulfuric acid solution 1% was stirred and refluxed for 7 hours. The reaction mixture was allowed to cool overnight to room temperature and treated with sodium carbonate till a turbid solution was obtained. The product was extracted with 1,1'-oxybisethane. The extract was washed with water, dried, filtered and evaporated, yielding 28.8 parts (98.6%) of 3-methoxy-1-(phenylmethyl)-4-piperidinone as an oily residue (intermediate 60).

EXAMPLE XXV

A mixture of 93 parts of 3,4,4-trimethoxy-1-methyl-1-(phenylmethyl)piperidinium methylsulfate in 400 parts of methanol was hydrogenated at normal pressure and at room temperature with 5 parts of palladium-on-charcoal catalyst 10%. After the calculated amount of hydrogen was taken up, the catalyst was filtered off and the filtrate was evaporated. The solid residue was dissolved in water and the whole was alkalized with a sodium hydroxide solution. The product was extracted with dichloromethane. The extract was washed with water and the aqueous phase was set aside. The organic phase was dried, filtered and evaporated, yielding 20 parts of an oily residue. The aqueous phase, which was set aside (see above), was concentrated. The product was extracted with dichloromethane. The extract was washed with a saturated sodium chloride solution, dried, filtered and evaporated, yielding 18 parts of an oily residue. The combined oily residues (resp. 20 and 18 parts) were dissolved in 2,2'-oxybispropane. The solution was filtered and the filtrate was evaporated. The residue was taken up in benzene and evaporation was continued, yielding 34 parts (75.7%) of 3,4,4-trimethoxy-1-methylpiperidine as a residue (intermediate 61).

EXAMPLE XXVI

To a stirred mixture of 17.1 parts of ethyl 4-oxo-1-piperidinecarboxylate and 225 parts of trichloromethane was added dropwise a solution of 16 parts of bromine in 75 parts of trichloromethane at −5°–0° C. The trichloromethane-phase was washed with ice-water, dried, filtered and evaporated, yielding 25 parts of ethyl 3-bromo-4-oxo-1-piperidinecarboxylate as an oily residue (intermediate 62).

To a stirred mixture of 200 parts of sodium methoxide solution 30% and 640 parts of methanol were added 250 parts of ethyl 3-bromo-4-oxo-1-piperidinecarboxylate at about 20° C. The whole was stirred for 3 hours at room temperature. The solvent was evaporated and the oily residue was dissolved in 2,2'-oxybispropane. The solution was washed with water, dried, filtered and evaporated, yielding 190 parts of ethyl 3-hydroxy-4,4-dimethoxy-1-piperidinecarboxylate as an oily residue (intermediate 63).

To a stirred mixture of 35 parts of ethyl 3-hydroxy-4,4-dimethoxy-1-piperidinecarboxylate and 144 parts of N,N-dimethylformamide were added portionwise 8.2 parts of sodium hydride dispersion 50%: exothermic reaction (temp. roses to 30° C.; cooling in a water-bath was necessary to keep the temperature below 30° C.). The whole was stirred for 1.50 hours at about 30° C. and then it is cooled to room temperature. 24.1 Parts of iodomethane were added dropwise (strong exothermic reaction) while the temperature was kept below 30° C. Upon completion, stirring was continued over weekend at room temperature. The reaction mixture was poured onto water and the product was extracted with 4-methyl-2-pentanone. The extract was washed with water, dried, filtered and evaporated, yielding 35.9 parts (95.7%) of ethyl 3,4,4-trimethoxy-1-piperidinecarboxylate as an oily residue (intermediate 64).

A mixture of 117.7 parts of ethyl 3,4,4-trimethoxy-1-piperidinecarboxylate, 267.3 parts of potassium hydroxide and 720 parts of 2-propanol was stirred and refluxed for 4 hours. The reaction mixture was evaporated. 900 Parts of water were added to the residue and the whole was stirred in a boiling water-bath. The last traces of 2-propanol were removed by evaporation on a Rotavapor. After cooling to 10° C., the product was extracted twice with 280 parts of 1,1'-oxybisethane. The extracts were dried, filtered and evaporated, yielding 62.9 parts (75.4%) of 3,4,4-trimethoxypiperidine as a residue (intermediate 65).

A mixture of 56.2 parts of 1,1'-(4-chlorobutylidene)bis[4-fluorobenzene], 31.5 parts of 3,4,4-trimethoxypiperidine, 42.5 parts of sodium carbonate, 1 part of potassium iodide and 960 parts of 4-methyl-2-pentanone was stirred and refluxed for 18 hours. The reaction mixture was cooled, filtered and the filtrate was evaporated, yielding 82.5 parts of 1-[4,4-bis(4-fluorophenyl)butyl]-3,4,4-trimethoxypiperidine as a residue (intermediate 66).

EXAMPLE XXVII

To a stirred solution of 35 parts of ethyl 3-hydroxy-4,4-dimethoxy-1-piperidinecarboxylate in 144 parts of N,N-dimethylformamide were added portionwise 8.2 parts of a sodium hydride dispersion 50% at about 30° C. After stirring for 1.50 hours at about 30° C., the mixture was cooled to room temperature and 26.5 parts of iodoethane were added dropwise at a temperature below 30° C. Upon completion, stirring was continued for 18 hours at room temperature. The reaction mixture was poured onto water and the product was extracted with 4-methyl-2-pentanone. The extract was washed with water, dried, filtered and evaporated, yielding 34.1 parts (87%) of ethyl 3-ethoxy-4,4-dimethoxy-1-piperidinecarboxylate as a residue (intermediate 67).

A mixture of 34.1 parts of ethyl 3-ethoxy-4,4-dimethoxy-1-piperidinecarboxylate and 1110 parts of a sulfuric acid solution 1% in water was stirred and refluxed for 3 hours. The reaction mixture was cooled and saturated with sodium carbonate. The product was extracted with dichloromethane. The extract was washed with a small amount of water, dried, filtered and evaporated. The residue was stirred in petroleumether. The product was separated and distilled, yielding 21.1 parts of ethyl 3-ethoxy-4-oxo-1-piperidinecarboxylate bp. ±95° C. at 0.05 mm. pressure (intermediate 68).

A mixture of 21 parts of ethyl 3-ethoxy-4-oxo-1-piperidinecarboxylate, 11 parts of benzenemethanamine, 1 part of a solution of thiophene in ethanol 4% and 320 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 18 parts of ethyl cis-4-amino-3-ethoxy-1-piperidinecarboxylate as a residue (intermediate 69).

EXAMPLE XXVIII

To a stirred suspension of 97.1 parts of 3-methoxy-1-(phenylmethyl)-4-piperidinone and 42.3 parts of sodium carbonate in 80 parts of ethanol and 100 parts of water was added dropwise a solution of 31.6 parts of hydroxylamine hydrochloride in 100 parts of water (exothermic reaction). Upon completion, stirring was continued overnight at reflux temperature. The reaction mixture was cooled to room temperature and the product was extracted with trichloromethane. The extract was washed with water, dried, filtered and evaporated. The oily residue was purified by column-chromatography over silica gel using a mixture of trichloromethane and methanol (95:5 by volume) as eluent. The pure fractions were collected and the eluent was evaporated, yielding 83.3 parts (84%) of 3-methoxy-1-(phenylmethyl)-4-piperidinone, oxime as a residue. (intermediate 70)

A mixture of 83 parts of 3-methoxy-1-(phenylmethyl)-4-piperidinone, oxime and 400 parts of methanol saturated with ammonia was hydrogenated at normal pressure and at 50° C. with 6 parts of Raney-nickel catalyst. After the calculated amount of hydrogen was taken up, the catalyst was filtered off and the filtrate was evaporated, yielding 78 parts (100%) of (cis+trans)-3-methoxy-1-(phenylmethyl)-4-piperidinamine as a residue (intermediate 71).

EXAMPLE XXIX

A mixture of 15 parts of trans-N-[3-hydroxy-1-(phenylmethyl)-4-piperidinyl]benzamide and 204 parts of a concentrated hydrochloric acid solution was stirred and refluxed for 18 hours. The reaction mixture was filtered and the filtrate was treated with sodium hydroxide. Upon cooling in an ice-bath, the addition of sodium hydroxide was continued till turbid. The product was extracted three times with 180 parts of methylbenzene. The combined extracts were dried, filtered and evaporated. The oily residue was dissolved in trichloromethane. The solution was washed with a small amount of water, dried, filtered and evaporated. The oily residue was purified by column-chromatography over silica gel using a mixture of trichloromethane and methanol, saturated with ammonia, (85:15 by volume) as eluent. The pure fractions were collected and the eluent was evaporated. The residue solidified on triturating in petroleumether. The product was filtered off and dried, yielding 3.8 parts of trans-4-amino-1-(phenylmethyl)-3-piperidinol; mp. 74.1° C. (intermediate 72).

In a similar manner there were also prepared:
cis-3-methoxy-1-(phenylmethyl)-4-piperidinamine as an oily residue (intermediate 73);
cis-4-amino-1-(phenylmethyl)-3-piperidinol as a residue (intermediate 74);
trans-3-methoxy-1-(phenylmethyl)-4-piperidinamine as a residue (intermediate 75); and
trans-1-[4,4-bis(4-fluorophenyl)butyl]-3-methoxy-4-piperidinamine as an oily residue (intermediate 76).

EXAMPLE XXX

To a stirred and refluxing mixture of 136 parts of 1-(2-hydroxyphenyl)ethanone and 222 parts of 1,3-dibromopropane in 500 parts of water was added dropwise a solution of 40 parts of sodium hydroxide in 140 parts of water. Upon completion, stirring was continued at reflux temperature overnight. The organic layer was separated, dried and distilled, yielding 80 parts of 1-[2-(3-bromopropoxy)phenyl]ethanone; bp. 135° C. at 0.05 mm. pressure (intermediate 77).

Following the same procedure and using equivalent amounts of the appropriate starting materials there were also prepared:
1-(5-bromopentyloxy)-4-fluorobenzene; bp. 116°–117° C. at 0.4 mm. pressure (intermediate 78);
1-(3-chloropropoxy)-3-(trifluoromethyl)benzene; bp. 97°–98° C. at 5 mm. pressure (intermediate 79); and
1-[(6-bromohexyl)oxy]-4-fluorobenzene; bp. 93°–95° C. at 0.03 mm. pressure (intermediate 80).

EXAMPLE XXXI

Through a stirred mixture of 11.7 parts of (5-fluoro-2-hydroxyphenyl)(4-fluorophenyl)methanone and 45 parts of N,N-dimethylformamide nitrogen was bubbled while cooling at about 5° C. (ice-bath). Then there were added portionwise 2.4 parts of sodium hydride dispersion 50%: heavy foaming occured. Upon completion, there were added 23.6 parts of 1-bromo-3-chloropropane while still cooling at 5° C. The whole was heated to 40° C. and stirring at this temperature was continued for one hour. After cooling to 5° C., the reaction mixture was poured onto 400 parts of water and the product was extracted twice with 180 parts of benzene. The extract was dried, filtered and evaporated. The residue was purified by column-chromatography over silica gel using trichloromethane as eluent. The pure fractions were collected and the eluent was evaporated. The residue solidified on triturating in petroleumether. After cooling to 0° C., the product was filtered off and dried, yielding 10.7 parts (69%) of [2-(3-chloropropoxy)-5-fluorophenyl] (4-fluorophenyl)methanone; mp. 60° C. (intermediate 81).

EXAMPLE XXXII

To a stirred sodium ethoxide solution, prepared starting from 3.5 parts of sodium in 24 parts of ethanol, were added 16.8 parts of 4-fluorophenol. After stirring for 15 minutes, there was added dropwise a solution of 77 parts of 1-bromo-3-chloro-2-methylpropane in 72 parts of ethanol at room temperature. Upon completion, stirring was continued for 20 hours at reflux temperature. The reaction mixture was filtered and the filtrate was evaporated. The residue was taken up in 2,2'-oxybispropane. The organic phase was washed with water and with alkaline water 5%, dried, filtered and evaporated. The residue was distilled, yielding 11.6 parts of 1-(3-chloro-2-methylpropoxy)-4-fluorobenzene; bp. 126° C. (water-jet) (intermediate 82).

EXAMPLE XXXIII

To a stirred solution of 10.6 parts of N-(4-fluorophenyl)-4-methylbenzenesulfonamide in 68 parts of N,N-dimethylformamide were added portionwise 2.1 parts of a sodium hydride dispersion 50%: temp. roses to 35° C. After stirring for 20 minutes, the whole was cooled in an ice-bath (about 15° C.) and 12.6 parts of 1-bromo-3-chloropropane were added quickly. Stirring was continued first for 20 minutes at room temperature, then for 3 hours at 75° C. and further overnight at room temperature. The reaction mixture was poured onto ice-water and the product was extracted with methylbenzene. The extract was washed three times with water, dried, filtered and evaporated. The residue was crystallized from petroleumether. The product was filtered off and recrystallized from 2,2'-oxybispropane, yielding 11.37 parts (83.2%) of N-(3-chloropropyl)-N-(4-fluorophenyl)-4-methylbenzenesulfonamide (intermediate 83).

In a similar manner there was also prepared: N-(3-chloropropyl)-4-fluoro-N-(4-fluorophenyl)benzamide as a residue (intermediate 84).

EXAMPLE XXXIV

To a stirred mixture of 46.46 parts of 1,4-cyclohexanediol and 135 parts of N,N-dimethylformamide were added 5.28 parts of sodium hydride dispersion 50% at a temperature below 20° C. Stirring was continued for 2 hours at room temperature under nitrogen atmosphere. Then there were added dropwise 15.9 parts of 1,4-difluoro-2-nitrobenzene at about 20° C. Upon completion, stirring was continued overnight at room temperature. The reaction mixture was poured onto water. The precipitated product was filtered off and taken up in trichloromethane. The solution was washed with water, dried, filtered and evaporated. The residue was boiled in 2-propanol. Upon cooling, the precipitate was filtered off and the filtrate was evaporated. The residue was purified by column-chromatography over silica gel using a mixture of trichloromethane and methanol (95:5 by volume) as eluent. The pure fractions were collected and the eluent was evaporated. The residue was stirred in petroleumether. The product was filtered off and dried, yielding 17.1 parts of 4-(4-fluoro-2-nitrophenoxy)-cyclohexanol; mp. 150.8° C. (intermediate 85).

EXAMPLE XXXV

To 31.4 parts of 3-fluorophenol were added dropwise 29.3 parts of cyclopropanecarbonyl chloride at 80° C. Upon completion, the whole was stirred for 1 hour at 80° C. The reaction mixture was distilled, yielding 49.7 parts (98%) of (3-fluorophenyl)cyclopropanecarboxylate; bp. 75°–85° C. at 0.5 mm. pressure (intermediate 86).

To a stirred and cooled (0° C.) mixture of 40.7 parts of (3-fluorophenyl) cyclopropanecarboxylate and 156 parts of dry dichloromethane were added portionwise 33.1 parts of aluminium chloride. The whole was heated in an oil-bath at 60° C. and the dichloromethane was distilled off. The whole was further heated till an internal temperature of 110° C. and stirring was continued for 15 minutes at this temperature. After cooling, the solid reaction mixture was pulverized and poured portionwise into a mixture of 400 parts of ice-water and 36 parts of concentrated hydrochloric acid. The whole was stirred for 3 hours at room temperature and the product was extracted twice with 140 parts of 1,1'- oxybispropane. The combined extracts were dried, filtered and evaporated. The residue was cooled and suspended in 35 parts of petroleumether. After cooling to 5° C., the product was filtered off (the filtrate was set aside) and dried, yielding 21.2 parts of crude product. The filtrate (which was set aside) was allowed to stand overnight at −15° C. The product was filtered off, yielding a second fraction of 2.4 parts of crude product. The combined crude crops (resp. 21.2 parts and 2.4 parts) were purified by column-chromatography over silica gel using trichloromethane as eluent. The pure fractions were collected and the eluent was evaporated. The residue was crystallized from 21 parts of petroleumether at 0° C. The product was filtered off and dried, yielding 15.2 parts of cyclopropyl (4-fluoro-2-hydroxyphenyl)methanone; mp. 58° C. (intermediate 87).

EXAMPLE XXXVI

A mixture of 16 parts of 1-cyclopropyl-2,2-diphenylethanone and 300 parts of hydrochloric acid were stirred and refluxed for 4 hours. The reaction mixture was cooled and extracted with 2,2'-oxybispropane. The extract was washed with water and with a diluted sodium hydrogen carbonate solution, dried, filtered and evaporated, yielding 17 parts of 5-chloro-1,1-diphenyl-2-pentanone as a residue (intermediate 88).

EXAMPLE XXXVII 30.6 Parts of cyclopropyl (4-fluoro-2-hydroxyphenyl)-methanone were added portionwise to 450 parts of hydroiodic acid solution 50%. The whole was heated to reflux and stirring was continued for 1.50 hours at reflux temperature. The reaction mixture was cooled to 0° C. The precipitated product was filtered off and dissolved in 300 parts of trichloromethane. The solution was dried, filtered and evaporated. The residue was dissolved in 210 parts of petroleumether while heating. The solution was treated twice with activated charcoal and the latter was filtered off each time. The filtrate was evaporated and the residue was suspended in 35 parts of petroleumether. After cooling to 0° C., the product was filtered off and dried, yielding 36.4 parts (70%) of 1-(4-fluoro-2-hydroxyphenyl)-4-iodo-1-butanone; mp. 41.4° C. (intermediate 89).

EXAMPLE XXXVIII

To a stirred mixture of 25 parts of 1,3-isobenzofurandione and 108.5 parts of fluorobenzene were added portionwise 50 parts of aluminium chloride. Upon completion, the whole was heated slowly to reflux and stirring was continued for 1.50 hours at reflux temperature. The reaction mixture was cooled and poured onto a mixture of crushed ice and 60 parts of concentrated hydrochloric acid. The product was extracted twice with dichloromethane. The combined extracts were washed with a sodium hydroxide solution 10%. The aqueous phase was separated, washed with 2,2'-oxybispropane and acidified with concentrated hydrochloric acid while cooling. The whole was stirred for 1 hour at room temperature. The precipitated product was filtered off and dissolved in benzene. The solution was distilled azeotropically to dry. The solid residue was stired in hexane. The product was filtered off and dried in vacuo at about 50° C., yielding 33.5 parts (80.7%) of 2-(4-fluorobenzoyl)-benzoic acid; mp. 129.2° C. (intermediate 90).

To 1190 parts of 1,1'-oxybisethane were added at once 50 parts of lithium aluminium hydride. Then there was added dropwise a solution of 213.7 parts of 2-(4-fluorobenzoyl)benzoic acid in 875 parts of 1,1'-oxybisethane so that the mixture was kept at reflux temperature. Upon completion, stirring was continued first for 30 minutes at room temperature, then for 2 hours at reflux and further overnight at room temperature. The reaction mixture was cooled to 0° C. and there were added dropwise successively 50 parts of water, 50 parts of a 15% sodium hydroxide solution and 150 parts of water all at 0° C. The reaction mixture was filtered over Hyflo and washed thoroughly with 1,1'-oxybisethane. The organic phase was separated, washed with water, dried, filtered and evaporated. The residue was crystallized from a mixture of benzene and hexane, yielding 170.4 parts of α-(4-fluorophenyl)-1,2-benzenedimethanol; mp. ±75° C. (intermediate 91).

A mixture of 200 parts of α-(4-fluorophenyl)-1,2-benzenedimethanol and 2295 parts of phosphoric acid 60% was stirred for 3 hours at 100° C. Stirring was continued overnight at room temperature. The reaction mixture was poured onto water and the product was extracted twice with 1,1'-oxybisethane. The combined extracts were washed with water, with a 10% sodium carbonate solution and again with water, dried, filtered and evaporated. The residue was distilled, yielding 57 parts of 1-(4-fluorophenyl)-1,3-dihydroisobenzofuran; bp. 108° C. at 0.2 mm. pressure (intermediate 92).

To a stirred and cooled (2-propanone/$CO_2$-bath) amount of 1080 parts of ammonia was added 1 part of iron (III) chloride, followed by the portionwise addition of 7.7 parts of sodium under nitrogen atmosphere. After stirring for 20 minutes, there was added dropwise a solution of 64.5 parts of 1-(4-fluorophenyl)-1,3-dihydroisobenzofuran in 105 parts of 1,1'-oxybisethane while still cooling. Then there was added dropwise a solution of 75 parts of 2-(3-bromopropoxy)tetrahydro-2H-pyran in 37 parts of 1,1'-oxybisethane. Upon completion, stirring was continued for 2 hours under nitrogen atmosphere in a 2-propanone/$CO_2$-bath. Without cooling and without nitrogen, there were added dropwise slowly 490 parts of 1,1'-oxybisethane and stirring was continued overnight at room temperature. 225 Parts of a saturate ammonium chloride solution were added dropwise followed by the addition of 200 parts of water. The layers were separated and the aqueous phase was extracted twice with 1,1'-oxybisethane. The combined organic phases were washed with water, dried, filtered and evaporated. The residue was purified by column-chromatography over silica gel using a mixture of trichloromethane and methanol (99.5:0.5 by volume) as eluent. The second fraction was collected and the eluent was evaporated, yielding 39.6 parts of 1-(4-fluorophenyl)-1,3-dihydro-1-[3-(tetrahydro-2H-pyran-2-yloxy)propyl]isobenzofuran as a residue (intermediate 93).

39.6 Parts of 1-(4-fluorophenyl)-1,3-dihydro-1-[3-(tetrahydro-2H-pyran-2-yloxy)propyl]isobenzofuran were dissolved in 9.8 parts of a hydrochloric acid solution 0.1M and 788 parts of ethanol and the whole was stirred and refluxed for 1 hour. The solvent was evaporated and the residue was taken up in methylbenzene and water. The organic phase was separated, washed with water, dried, filtered and evaporated. The residue was purified by column-chromatography over silica gel using a mixture of trichloromethane and methanol (99:1 by volume) as eluent. The pure fractions were collected and the eluent was evaporated, yielding 24.2 parts of 1-(4-fluorophenyl)-1,3-dihydroisobenzofuran-1-propanol as a residue (intermediate 94).

EXAMPLE XXXIX

A mixture of 4.4 parts of 3,4-pyridinediamine, 4.0 parts of isothiocyanatomethane, 90 parts of tetrahydrofuran and 40 parts of acetonitrile was stirred and refluxed overnight. The reaction mixture was evaporated, yielding 7.3 parts of N-(3-amino-4-pyridinyl)-N'-methylthiourea as a residue (intermediate 95).

A mixture of 7.3 parts of N-(3-amino-4-pyridinyl)-N'-methylthiourea, 15 parts of mercury (II)oxide, 90 parts of tetrahydrofuran and 80 parts of acetonitrile was stirred and refluxed for 20 hours. The reaction mixture was filtered hot over Hyflo and the filter-cake was washed with 240 parts of boiling ethanol. The filtrate was evaporated in vacuo and the residue was boiled in acetonitrile. The product was filtered off and dried, yielding 5 parts of N-methyl-3H-imidazo[4,5-c]pyridin-2-amine; mp. 255.7° C. (intermediate 96).

A mixture of 5.6 parts of 1-(chloromethyl)-4-fluorobenzene, 5.2 parts of N-methyl-3H-imidazo[4,5-c]-pyridine-2-amine, 4.2 parts of sodium carbonate and 90 parts of N,N-dimethylformamide was stirred and heated first for 3 hours at 90°-100° C. and further overnight at 60° C. The reaction mixture was poured onto water and the product was extracted four times with dichloromethane. The combined extracts were dried, filtered and evaporated. The residue was purified by column-chromatography over silica gel using a mixture of trichloromethane and methanol (92.5:7.5 by volume) as eluent. The pure fractions were collected and the eluent was evaporated. The residue was boiled in 2-propanone, yielding 6 parts of 5-[(4-fluorophenyl)methyl]-N-methyl-5H-imidazo[4,5-c]pyridin-2-amine; mp. 209.5° C. (intermediate 97).

A mixture of 3.0 parts of 5-[(4-fluorophenyl)methyl]-N-methyl-5H-imidazo[4,5-c]pyridin-2-amine, 2.4 parts of methyl carbonochloridate, 1.2 parts of N,N-diethylethanamine and 260 parts of dichloromethane was stirred for 2 days at room temperature. The reaction mixture was evaporated. The solid residue was purified by column-chromatography over silica gel using a mixture of trichloromethane and methanol (94:6 by volume) as eluent. The pure fractions were collected and the eluent was evaporated. The residue was crystallized from 2-propanone, yielding 1 part of methyl [[5-[(4-fluorophenyl)methyl]-5H-imidazo[4,5-c]pyridin-2-yl]methyl]-carbamate; mp. 178.8° C. (intermediate 98).

EXAMPLE XL

A mixture of 10 parts of bis(4-fluorophenyl)methanone, 22.1 parts of 3-chloro-1,2-propanediol, 0.2 parts of 4-methylbenzenesulfonic acid hydrate and 90 parts of methylbenzene was stirred and refluxed for 23 hours using a water-separator. The reaction mixture was poured onto alkaline water. Upon stirring, the layers were separated. The organic phase was washed with alkaline water, dried, filtered and evaporated, yielding 14 parts (100%) of 2,2-bis(4-fluorophenyl)-4-(chloromethyl)-1,3-dioxolane as a residue (intermediate 99).

EXAMPLE XLI

To a stirred solution of 24.2 parts of 1-(4-fluorophenyl)-1,3-dihydroisobenzofuran-1-propanol in 8 parts of pyridine and 90 parts of trichloromethane were added dropwise 12.1 parts of thionyl chloride. Upon completion, the whole was heated slowly to 50° C. and stirring at this temperature was continued for 3 hours. The reaction mixture was poured onto ice-water. The organic phase was separated, washed with a sodium hydrogen carbonate solution (10%), dried and evaporated, yielding 20 parts of 1-(3-chloropropyl)-1-(4-fluorophenyl)-1,3-dihydroisobenzofuran as a residue (intermediate 100).

EXAMPLE XLII

To a stirred mixture of 324 parts of 2-(2,4-dichlorophenoxy)-1-propanol and 700 parts of N,N-diethylethanamine were added dropwise at room temperature 335 parts of methanesulfonyl chloride (exothermic reaction: the temperature roses to reflux temperature). While cooling in a water-bath, stirring was continued for 30 minutes at room temperature. The reaction mixture was poured onto water and the product was extracted with 2,2'-oxybispropane. The extract was dried, filtered and evaporated. The residue was distilled by vacuum distillation, yielding 300 parts of 2-(2,4-dichlorophenoxy)-1-propanol methanesulfonate (ester); bp. 130° C. at $2 \times 10^{-4}$ mm. pressure (intermediate 101).

EXAMPLE XLIII

To a stirred mixture of 18.3 parts of 4-(4-fluoro-2-nitrophenoxy)cyclohexanol, 6.23 parts of pyridine and 135 parts of trichloromethane were added dropwise, during a 10 minutes period, 9 parts of methanesulfonyl chloride. Upon completion, stirring was continued overnight at room temperature. The whole was further stirred and refluxed for 2 hours. The reaction mixture was evaporated and the residue was stirred in water. The product was extracted with trichloromethane. The extract was dried, filtered and evaporated. The residue was purified by column-chromatography over silica gel using trichloromethane as eluent. The pure fractions were collected and the eluent was evaporated. The residue was crystallized from 1,1'-oxybisethane, yielding 8.5 parts of 4-(4-fluoro-2-nitrophenoxy)cyclohexanol methanesulfonate (ester); mp. 111.7° C. (intermediate 102).

EXAMPLE XLIV

A solution of 20 parts of ethyl 3-methoxy-4-oxo-1-piperidinecarboxylate, 12 parts of (−)-α-methylbenzenemethanamine, 2 parts of a solution of thiophene in ethanol 4% and 200 parts of methanol was hydrogenated at normal pressure and at room temperature with 4 parts of palladium-on-charcoal catalyst 10%. After the calculated amount of hydrogen was taken up, the catalyst was filtered off and the filtrate was evaporated in vacuo. The residue was purified by HPLC using a mixture of hexane, trichloromethane and methanol (50:49.5:0.5 by volume) as eluent. The pure A-fractions were collected and the eluent was evaporated, yielding 15.62 parts (51%) of (−)-ethyl cis-3-methoxy-4-[(1-phenylethyl)-amino]-1-piperidinecarboxylate as a residue (intermediate 103).

In a similar manner there were also prepared:
(+)-ethyl cis-3-methoxy-4-[(1-phenylethyl)amino]-1-piperidinecarboxylate as a residue (intermediate 104); and
ethyl cis-3-methoxy-4-[(phenylmethyl)amino]-1-piperidinecarboxylate monohydrochloride; mp. 185.8° C. (intermediate 104).

EXAMPLE XLV

A solution of 16 parts of (+)-ethyl cis-3-methoxy-4-[(1-phenylethyl)amino]-1-piperidinecarboxylate in 170 parts of a hydrochloric acid solution 6N was stirred and refluxed for 45 hours. The reaction mixture was cooled and washed with dichloromethane. The aqueous phase was cooled in an ice-bath and treated with ammonium hydroxide. The product was extracted three times with 130 parts of dichloromethane. The combined extracts were washed with 10 parts of water, dried, filtered and evaporated. The residue was dissolved in methylbenzene and the latter was evaporated again, yielding 12.2 parts (100%) of (+)-cis-3-methoxy-N-(1-phenylethyl)-4-piperidinamine as a residue (intermediate 105).

In a similar manner there was also prepared:
(−)-cis-3-methoxy-N-(1-phenylethyl)-4-piperidinamine as an oily residue (intermediate 106).

EXAMPLE XLVI

A mixture of 134 parts of ethyl cis-3-methoxy-4-[(phenylmethyl)amino]-1-piperidinecarboxylate, 255.2 parts of potassium hydroxide and 1760 parts of 2-propanol was stirred and refluxed for 3.50 hours. The reaction mixture was evaporated, water was added and the whole was evaporated again. The residue was taken up in water and extracted with dichloromethane. The extract was washed with water, dried, filtered and evaporated. The residue was purified by column-chromatography over silica gel using a mixture of trichloromethane and methanol (92.5:7.5 by volume) as eluent. The pure fractions were collected and the eluent was evaporated. The residue was converted into the hydrochloride salt in acetonitrile and 2-propanol. The salt was filtered off and dried, yielding 1.96 parts of cis-3-methoxy-N-(phenylmethyl)-4-piperidinamine dihydrochloride monohydrate; mp. 188° C. (intermediate 107).

EXAMPLE XLVII

To a stirred mixture of 62.83 parts of 4,4-dimethoxy-1-(phenylmethyl)-3-piperidinol and 180 parts of N,N-dimethylformamide were added portionwise 12.96 parts of a sodium hydride dispersion 50% at a temperature below 30° C. Stirring was continued for 2 hours at room temperature: mixture I.

43.02 Parts of 2-chloro-N,N-diethylethanamine hydrochloride were taken up in a dilute ammonium hydroxide solution and 1,1'-oxybisethane was added. The organic phase was separated, dried, filtered and evaporated. The residue was taken up in 45 parts of N,N-dimethylformamide and this solution was added dropwise to mixture I (see above). Upon completion, stirring was continued overnight at room temperature. The reaction mixture was poured onto water and the product was extracted with trichloromethane. The extract was washed with water, dried, filtered and evaporated. The residue was purified by column-chromatography over silica gel using a mixture of trichloromethane and methanol (90:10 by volume) as eluent. The pure fractions were collected and the eluent was evaporated, yielding 46.5 parts (53%) of N,N-diethyl-2-[[4,4-dimethoxy-1-(phenylmethyl)-3-piperidinyl]oxy]ethanamine as a residue (intermediate 108).

A mixture of 13.5 parts of N,N-diethyl-2-[[4,4-dimethoxy-1(phenylmethyl)-3-piperidinyl]oxy]ethanamine and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 10.5 parts (100%) of N,N-diethyl-2-[(4,4-dimethoxy-3-piperidinyl)oxy]ethanamine as a residue (intermediate 109).

EXAMPLE XLVIII

To a stirred solution of 4.1 parts of ethyl 4-amino-5-cyano-2-hydroxybenzoate in 40 parts of 2-propanone were added successively 2.52 parts of dimethyl sulfate and 4.1 parts of potassium carbonate. The whole was stirred and refluxed for 3 hours. The reaction mixture was filtered while hot and the filter-cake was washed with 2-propanone. The filtrate was evaporated and the solid residue was crystallized from 24 parts of 2-propanol, yielding 3.5 parts (79.5%) of ethyl 4-amino-5-cyano-2-methoxybenzoate; mp. 164.5° C. (intermediate 110).

EXAMPLE IL

A suspension of 10.69 parts of ethyl 4-amino-5-cyano-2-methoxybenzoate in 12 parts of a sodium hydroxide solution 50% and 500 parts of water was stirred and heated to 50° C. and stirring was continued for 1 hour at 50°-55° C. The reaction mixture was cooled and filtered. The filtrate was acidified with concentrated hydrochloric acid to pH 1-2. The precipitated product was filtered off, washed thoroughly with water and dried overnight at 80° C., yielding 8.6 parts (93.2%) of 4-amino-5-cyano-2-methoxybenzoic acid; mp. 236.7° C. (intermediate 111).

Following the same hydrolyzing procedure there was also prepared:
5-chloro-4-hydroxy-2-methoxybenzoic acid; mp. 239.4° C. (intermediate 112).

EXAMPLE L

A mixture of 9 parts of cis-1-(1H-benzimidazol-2-ylmethyl)-3-methoxy-4-piperidinamine and 150 parts of acetic acid was hydrogenated at normal pressure and at room temperature with 2 parts of rhodium-on-charcoal catalyst 5%. After the calculated amount of hydrogen was taken up, the catalyst was filtered off and the filtrate was evaporated. The residue was purified by column-chromatography over silica gel using a mixture of trichloromethane and methanol (90:10 by volume) saturated with ammonia, as eluent. The second fraction was collected and the eluent was evaporated, yielding 5 parts of cis-3-methoxy-1-[(4,5,6,7-tetrahydro-1H-benzimidazol-2-yl)-methyl]-4-piperidinamine as a residue (intermediate 113).

EXAMPLE LI

To a stirred solution of 11.2 parts of (4-fluorophenyl)(4-piperidinyl)methanone in 80 parts of 4-methyl-2-pentanone were added 5 parts of N-(2-chloroethyl)-3-pyridinecarboxamide and the whole was stirred and refluxed overnight. The reaction mixture was filtered and the filtrate was evaporated. The residue was purified by column-chromatography over silica gel using a mixture of trichloromethane and methanol (95:5 by volume) as eluent. The pure fractions were collected and the eluent was evaporated. The residue was crystallized from a mixture of 4-methyl-2-pentanone and 2,2'-oxybispropane, yielding 1.6 parts (16.5%) of N-[2-[4-(4-fluorobenzoyl)-1-piperidinyl]ethyl]-3-pyridinecarboxamide; mp. 118.3° C. (intermediate 114).

EXAMPLE LII

A mixture of 7.5 parts of 1-(3-chloropropoxy)-4-fluorobenzene, 10.5 parts of N,N-diethyl-2-[(4,4-dimethoxy-3-piperidinyl)oxy]ethanamine, 7 parts of N,N-diethylethanamine, 1 part of potassium iodide and 90 parts of N,N-dimethylformamide was stirred for 17 hours at 60° C. The reaction mixture was poured onto water and the product was extracted with trichloromethane. The extract was washed with water, dried, filtered and evaporated. The residue was purified by column-chromatography over silica gel using a mixture of trichloromethane and methanol (95:5 by volume) saturated with ammonia, as eluent. The pure fractions were collected and the eluent was evaporated. The residue was converted into the hydrochloride salt in acetonitrile and 2-propanol. The whole was evaporated and the residue was taken up in acetonitrile. The solution was evaporated, yielding 14 parts (75%) of N,N-diethyl-2-[[1-[3-(4-fluorophenoxy)propyl]-4,4-dimethoxy-3-piperidinyl]oxy]ethanamine as a residue (intermediate 115).

In a similar manner there were also prepared:
cis-1-(1H-benzimidazol-2-ylmethyl)-3-methoxy-N-(phenylmethyl)-4-piperidinamine as a residue (intermediate 116);
cis-1-[3-(4-fluorophenoxy)propyl]-3-methoxy-N-(phenylmethyl)-4-piperidinamine dihydrochloride (intermediate 117);
(+)-cis-1-[3-(4-fluorophenoxy)propyl]-3-methoxy-N-(1-phenylethyl)-4-piperidinamine as a residue (intermediate 118); and
(−)-cis-1-[3-(4-fluorophenoxy)propyl]-3-methoxy-N-(1-phenylethyl)-4-piperidinamine as a residue (intermediate 119).

EXAMPLE LIII

A mixture of 14.07 parts of N,N-diethyl-2-[[1-[3-(4-fluorophenoxy)propyl]-4,4-dimethoxy-3-piperidinyl]oxy]ethanamine dihydrochloride, 7.36 parts of a sulfuric acid solution 96% and 500 parts of water was stirred and refluxed for 17 hours. The reaction mixture was allowed to cool and washed with 2,2'-oxybispropane. The aqueous phase was separated and alkalized with sodium carbonate. The product was extracted with dichloromethane. The extract was dried, filtered and evaporated. The residue was purified by column-chromatography over silica gel using a mixture of trichloromethane and methanol (95:5 by volume) saturated with ammonia, as eluent. The pure fractions were collected and the eluent was evaporated, yielding 8.0 parts (75%) of 3-[2-(diethylamino)-ethoxy]-1-[3-(4-fluorophenoxy) propyl]-4-piperidinone as a residue (intermediate 120).

EXAMPLE LIV

A mixture of 5.1 parts of trans-N-[1-[3-(4-fluorophenoxy)propyl]-3-methoxy-4-piperidinyl]benzamide and 84 parts of a concentrated hydrochloric acid solution was stirred and refluxed for 22 hours in an oil-bath at 140° C. The reaction mixture was cooled, filtered and the filter-cake was washed with water. The filtrate was evaporated. The residue was taken up in 35 parts of water and the whole was treated with sodium hydroxide solution. The product was extracted three times with methylbenzene. The combined extracts were washed with a small amount of water, dried, filtered and evaporated, yielding 2.9 parts (79%) of trans-1-[3-(4-fluorophenoxy)propyl]-3-methoxy-4-piperidinamine as a residue (intermediate 121).

EXAMPLE LV

A mixture of 18 parts of cis-1-(1H-benzimidazol-2-ylmethyl)-3-methoxy-N-(phenylmethyl)-4-piperidinamine and 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated. The residue was purified by column-chromatography over silica gel using a mixture of trichloromethane and methanol (93:7 by volume), saturated with ammonia, as eluent. The pure fractions were collected and the eluent was evaporated. The residue solidified slowly and the solid product was suspended in 2,2'-oxybispropane. The product was filtered off and dried at the air, yielding 6 parts of cis-1-(1H-benzimidazol-2-ylmethyl)-3-methoxy-4-piperidinamine dihydrate:mp. 92.0° C. (intermediate 122).

Following the same hydrogenating procedure there were also prepared:
cis-1-[3-(4-fluorophenoxy)propyl]-3-methoxy-4-piperidinamine as a residue (intermediate 123);
(+)-cis-1-[3-(4-fluorophenoxy)propyl]-3-methoxy-4-piperidinamine as a residue (intermediate 124): and
(−)-cis-1-[3-(4-fluorophenoxy)propyl]-3-methoxy-4-piperidinamine as a residue (intermediate 125).

EXAMPLE LVI

A mixture of 8.0 parts of 3-[2-(diethylamino)ethoxy]-1-[3-(4-fluorophenoxy)propyl]-4-piperidinone, 2.5 parts of benzenemethanamine, 1 part of a solution of thiophene in ethanol 4% and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column-chromatography over silica gel using a mixture of trichloromethane and methanol (95:5 by volume) saturated with ammonia, as eluent. The pure fractions were collected and the eluent was evaporated, yielding 3.6 parts (45%) of cis-3-[2-(diethylamino)ethoxy]-1-[3-(4-fluorophenoxy)-propyl]-4-piperidinamine as a residue (intermediate 126).

B. Preparation of Final Compounds

EXAMPLE LVII

A mixture of 4.7 parts of 1-(3-chloropropoxy)-4-fluorobenzene, 3.015 parts of cis-4-amino-5-chloro-2-methoxy-N-(3-methoxy-4-piperidinyl)benzamide, 0.1 parts of potassium iodide, 3 parts of N,N-diethylethanamine and 45 parts of N,N-dimethylformamide was stirred and heated for 18 hours at 60° C. The reaction mixture was poured onto water. The precipitated product was filtered off and dissolved in trichloromethane. The solution was washed with water. The organic phase was separated, dried, filtered and evaporated. The residue was purified by column-chromatography over silica gel using a mixture of trichloromethane and methanol (90:10 by volume) as eluent. The pure fractions were collected and the eluent was evaporated. The oily residue was crystallized from 2-propanol. The product was filtered off and dried, yielding 3.11 parts (42.8%) of cis-4-amino-5-chloro-N-[1-[3-(4-fluorophenoxy)propyl]-3-methoxy-4-piperidinyl]-2-methoxybenzamide monohydrate; mp. 109.8° C. (compound 1).

Following the same procedure and using equivalent amounts of the appropriate starting materials there were also prepared:

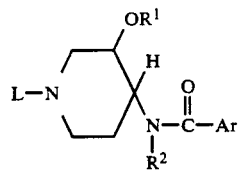

| No. | L | $R^1$ | $R^2$ | Ar | cis/trans isomerism | base/salt form | mp. °C. |
|---|---|---|---|---|---|---|---|
| 2 | $CH_3$ | $CH_3$ | $C_6H_5$ | $C_6H_5$ | cis | base | 119.3 |
| 3 | $4\text{-}F\text{-}C_6H_4\text{-}CO\text{-}(CH_2)_3$ | H | H | $C_6H_5$ | cis | base | 138.5 |
| 4 | (1H-indol-3-yl)-$(CH_2)_2$ | H | H | $C_6H_5$ | cis | base | 186.0 |
| 5 | (1H-indol-3-yl)-$(CH_2)_2$ | $CH_3$ | H | $C_6H_5$ | cis | base | 140.7 |
| 6 | 2,3-dihydro-1,4-benzo-dioxin-2-ylmethyl | $CH_3$ | H | $C_6H_5$ | cis | base | 151.6 |
| 7 | 2,3-dihydro-1,4-benzo-dioxin-2-ylmethyl | $CH_3$ | H | $C_6H_5$ | trans | base | 167.6 |
| 8 | (1H-indol-3-yl)-$(CH_2)_2$ | $CH_3$ | H | $C_6H_5$ | trans | base | 177.2 |
| 9 | 2,3-dihydro-1,4-benzo-dioxin-2-ylmethyl | H | H | $C_6H_5$ | trans | base | 163.0 |
| 10 | 2,3-dihydro-1,4-benzo-dioxin-2-ylmethyl | H | H | $C_6H_5$ | cis | base | 135.2 |
| 11 | (1H-indol-3-yl)$CH_2\text{-}CH_2$ | H | H | $C_6H_5$ | trans | base | 203.2 |
| 12 | $C_6H_4\text{-}CH_2$ | H | H | $C_6H_5$ | trans | base | 213.2 |
| 13 | $4\text{-}Cl\text{-}C_6H_3\text{-}CH_2$ | H | H | $4\text{-}NH_2,5\text{-}Cl,2\text{-}OCH_3\text{-}C_6H_2$ | cis | base | 208 |
| 14 | $(4\text{-}F\text{-}C_6H_4)_2CH(CH_2)_3$ | H | H | $4\text{-}NH_2,5\text{-}Cl,2\text{-}OCH_3\text{-}C_6H_2$ | cis | base | 128.4 |
| 15 | $(4\text{-}Cl\text{-}C_6H_4)CH(CH_3)$ | H | H | $4\text{-}NH_2,5\text{-}Cl,2\text{-}OCH_3\text{-}C_6H_2$ | cis | base | 185.3 |
| 16 | $C_6H_5\text{-}CH=CHCH_2$ | H | H | $4\text{-}NH_2,5\text{-}Cl,2\text{-}OCH_3\text{-}C_6H_2$ | cis | base | 172.1 |
| 17 | (2-naphthalenylmethyl) | H | H | $4\text{-}NH_2,5\text{-}Cl,2\text{-}OCH_3\text{-}C_6H_2$ | cis | base | 192 |
| 18 | $(4\text{-}F\text{-}C_6H_4)_2CH(CH_2)_3$ | $CH_3$ | H | $C_6H_5$ | cis | $(COOH)_2$ | 192.4 |
| 19 | $CH_2=CH\text{-}CH_2$ | H | H | $4\text{-}NH_2,5\text{-}Cl,2\text{-}OCH_3\text{-}C_6H_2$ | cis | base | 141.7 |
| 20 | $(4\text{-}F\text{-}C_6H_4)_2CH(CH_2)_3$ | $CH_3$ | H | $4\text{-}NH_2,5\text{-}Cl,2\text{-}OCH_3\text{-}C_6H_2$ | cis | HCl | 228.1 |
| 21 | $4\text{-}F\text{-}C_6H_4\text{-}CH_2$ | $CH_3$ | H | $4\text{-}NH_2,5\text{-}Cl,2\text{-}OCH_3 C_6H_2$ | cis | base | 216.5 |

In a similar manner there are also prepared:

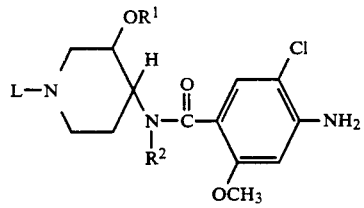

| No. | L | $R^1$ | $R^2$ | cis/trans isomerism | base/salt form | mp. °C. |
|---|---|---|---|---|---|---|
| 22 | $C_6H_5\text{-}CH=CH\text{-}CH_2$ | $CH_3$ | H | cis | base | 161.8 |
| 23 | $4\text{-}CH_3O\text{-}C_6H_4\text{-}CH_2\text{-}CH_2$ | $CH_3$ | H | cis | base | 218.5 |
| 24 | 2,3-dihydro-1,4-benzodioxin-2-ylmethyl | $CH_3$ | H | cis | base | 207.7 |
| 25 | $4\text{-}Cl\text{-}C_6H_4\text{-}CH_2$ | $CH_3$ | H | cis | base | 171.8 |
| 26 | $4\text{-}F\text{-}C_6H_4\text{-}O\text{-}(CH_2)_3$ | $CH_3$ | H | cis | $(COOH)_2.H_2O$ | 196.3 |
| 27 | $3\text{-}F\text{-}C_6H_4\text{-}CH_2$ | $CH_3$ | H | cis | base | 176.7 |
| 28 | $4\text{-}[(CH_3)_2CH]\text{-}C_6H_4\text{-}CH_2$ | $CH_3$ | H | cis | base | 144.4 |
| 29 | $4\text{-}CH_3\text{-}C_6H_4\text{-}CH_2$ | $CH_3$ | H | cis | base | 163 |
| 30 | (4-pyridinyl)-$CH_2$ | $CH_3$ | H | cis | base | 245.6 |
| 31 | [5-($CH_3COO$)-2-furanyl]-$CH_2$ | $CH_3$ | H | cis | base | 88.8 |
| 32 | $4\text{-}F\text{-}C_6H_4\text{-}CO\text{-}CH_2$ | $CH_3$ | H | cis | base | 172.1 |
| 33 | 1H-benzimidazol-2-ylmethyl | $CH_3$ | H | cis | base | 239.9 |
| 34 | $4\text{-}(NH_2SO_2)\text{-}C_6H_4\text{-}CH_2$ | $CH_3$ | H | cis | $HCl.H_2O$ | 255.9 |
| 36 | 2-thienyl-$CH_2$ | $CH_3$ | H | cis | base | 170.4 |
| 37 | $2\text{-}CH_3O\text{-}C_6H_4\text{-}O\text{-}(CH_2)_2$ | $CH_3$ | H | cis | $H_2O$ | 109.8 |
| 38 | $C_6H_5\text{-}O\text{-}CH(CH_3)\text{-}CH_2$ | $CH_3$ | H | cis | $H_2O$ | 121.7 |

-continued

In a similar manner there are also prepared:

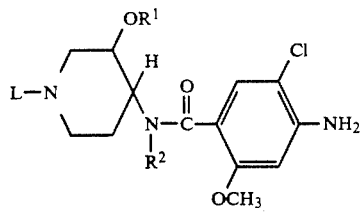

| No. | L | R¹ | R² | cis/trans isomerism | base/salt form | mp in °C. |
|---|---|---|---|---|---|---|
| 39 | 4-F—C$_6$H$_4$—O—(CH$_2$)$_3$ | H | H | cis | base | 130.5 |
| 40 | (4-F—C$_6$H$_4$)$_2$C(COOC$_2$H$_5$)—(CH$_2$)$_3$ | CH$_3$ | H | cis | H$_2$O | 109.6 |
| 41 | (4-F—C$_6$H$_4$)S—(CH$_2$)$_3$ | CH$_3$ | H | cis | base | 108.6 |
| 42 | [2,6-(CH$_3$)$_2$]—C$_6$H$_3$—NHCOCH$_2$ | CH$_3$ | H | cis | base | 266.0 |
| 43 | 4-F—C$_6$H$_4$—O—(CH$_2$)$_3$ | C$_2$H$_5$ | H | cis | ½ H$_2$O | 77.3–80.1 |
| 44 | 4-F—C$_6$H$_4$—CH=CH—(CH$_2$)$_2$ | CH$_3$ | H | cis | H$_2$O | 141.4–145.1 |
| 45 | (1H-indol-3-yl)-CH$_2$CH$_2$ | CH$_3$ | H | cis | H$_2$O | 189.5 |
| 46 | (4-F,2-NO$_2$—C$_6$H$_3$)—O—(CH$_2$)$_3$ | CH$_3$ | H | cis | H$_2$O | 115–145 |
| 47 | 4-F—C$_6$H$_4$—O—(CH$_2$)$_3$ | CH$_3$ | CH$_3$ | cis | HCl.H$_2$O | 247.1–250.2 |

| No. | L | R¹ | R² | Ar | cis/trans isomerism | base/salt form | mp in °C. |
|---|---|---|---|---|---|---|---|
| 48 | C$_6$H$_4$—CH$_2$ | H | H | C$_6$H$_5$ | cis | base | 143.2 |
| 49 | 4-NO$_2$—C$_6$H$_4$—CH$_2$ | CH$_3$ | H | 4-NH$_2$,5-Cl,2-OCH$_3$—C$_6$H$_2$ | cis | base | 209.0 |
| 50 | C$_6$H$_5$—NH—(CH$_2$)$_2$ | CH$_3$ | H | 4-NH$_2$,5-Cl,2-OCH$_3$—C$_6$H$_2$ | cis | H$_2$O | 115.7 |
| 51 | (2-pyridinyl)CH$_2$ | CH$_3$ | CH$_3$ | 4-NH$_2$,5-Cl,2-OCH$_3$—C$_6$H$_2$ | cis | 2HCl.2H$_2$O | 168.9 |
| 52 | (2-pyridinyl)CH(CH$_3$) | CH$_3$ | H | 4-NH$_2$,5-Cl,2-OCH$_3$—C$_6$H$_2$ | cis | 2HCl.2H$_2$O | 227.1 |
| 53 | 4-F—C$_6$H$_4$—CH(2-thienyl)-(CH$_2$)$_3$ | CH$_3$ | H | 4-NH$_2$,5-Cl,2-OCH$_3$—C$_6$H$_2$ | cis | H$_2$O | 103.1 |
| 54 | 2-CH$_3$CO—C$_6$H$_4$—O—(CH$_2$)$_3$ | CH$_3$ | H | 4-NH$_2$,5-Cl,2-OCH$_3$—C$_6$H$_2$ | cis | H$_2$O | 108.4–111.7 |
| 55 | 2-CH$_3$O—C$_6$H$_4$—O—(CH$_2$)$_3$ | CH$_3$ | H | 4-NH$_2$,5-Cl,2-OCH$_3$—C$_6$H$_2$ | cis | H$_2$O | 103.9 |
| 56 | (C$_2$H$_5$)$_2$N—(CH$_2$)$_2$ | CH$_3$ | H | 4-NH$_2$,5-Cl,2-OCH$_3$—C$_6$H$_2$ | cis | 2H$_2$O | 98.1 |
| 57 | CH$_3$C(O)—(CH$_2$)$_3$ | CH$_3$ | H | 4-NH$_2$,5-Cl,2-OCH$_3$—C$_6$H$_2$ | cis | H$_2$O | 91.1 |
| 58 | 4-F—C$_6$H$_4$—O—(CH$_2$)$_3$ | CH$_3$ | H | C$_6$H$_5$ | trans | base | 147.0 |
| 59 | 4-F—C$_6$H$_4$—O—(CH$_2$)$_3$ | CH$_3$ | H | 4-NH$_2$,5-CONH$_2$, 2-OCH$_3$—C$_6$H$_2$ | cis | H$_2$O | 127.9–193.9 |
| 60 | 4-F—C$_6$H$_4$—O—(CH$_2$)$_5$ | CH$_3$ | H | 4-NH$_2$,5-Cl,2-OCH$_3$—C$_6$H$_2$ | cis | H$_2$O | 106.6 |
| 61 | (C$_6$H$_5$)$_2$—N—(CH$_2$)$_3$ | CH$_3$ | H | 4-NH$_2$,5-Cl,2-OCH$_3$—C$_6$H$_2$ | cis | H$_2$O | 109.1 |
| 62 | 4-F—C$_6$H$_4$—O—(CH$_2$)$_6$ | CH$_3$ | H | 4-NH$_2$,5-Cl,2-OCH$_3$—C$_6$H$_2$ | cis | H$_2$O | 86.4 |
| 63 | (4-F—C$_6$H$_4$)(4-CH$_3$—C$_6$H$_4$—SO$_2$)N—(CH$_2$)$_3$ | CH$_3$ | H | 4-NH$_2$,5-Cl,2-OCH$_3$—C$_6$H$_2$ | cis | H$_2$O | 109.0 |
| 64 | (4-F—C$_6$H$_4$)$_2$CH—O—(CH$_2$)$_2$ | CH$_3$ | H | 4-NH$_2$,5-Cl,2-OCH$_3$—C$_6$H$_2$ | cis | H$_2$O | 89.7 |
| 65 | (C$_6$H$_5$)$_2$N—C(O)—(CH$_2$)$_2$ | CH$_3$ | H | 4-NH$_2$,5-Cl,2-OCH$_3$—C$_6$H$_2$ | cis | H$_2$O | 126.2 |
| 66 | (4-F—C$_6$H$_4$)(4-F—C$_6$H$_4$—C(O))N—(CH$_2$)$_3$ | CH$_3$ | H | 4-NH$_2$,5-Cl,2-OCH$_3$—C$_6$H$_2$ | cis | base | 183.2 |
| 67 | (4-F,2-NO$_2$—C$_6$H$_3$)-O-⟨cyclohexyl⟩ | CH$_3$ | H | 4-NH$_2$,5-Cl,2-OCH$_3$—C$_6$H$_2$ | cis | base | — |
| 68 | 4-F—C$_6$H$_4$—O—CH$_2$CH(CH$_3$)CH$_2$ | CH$_3$ | H | 4-NH$_2$,5-Cl,2-OCH$_3$—C$_6$H$_2$ | cis | base | 92.3 |
| 69 | (C$_6$H$_5$)$_3$—C—(CH$_2$)$_3$ | CH$_3$ | H | 4-NH$_2$,5-Cl,2-OCH$_3$—C$_6$H$_2$ | cis | H$_2$O | 148.9 |
| 70 | [1-(4-F—C$_6$H$_4$)-1,3-dihydro-1-isobenzofuranyl](CH$_2$)$_3$ | CH$_3$ | H | 4-NH$_2$,5-Cl,2-OCH$_3$—C$_6$H$_2$ | cis | base | 124.3 |
| 71 | ⟨cyclohexyl⟩-O—(CH$_2$)$_3$ | CH$_3$ | H | 4-NH$_2$,5-Cl,2-OCH$_3$—C$_6$H$_2$ | cis | base | 95.9–100.9 |

EXAMPLE LVIII

A mixture of 4.1 parts of 1-(3-chloropropoxy)-4-fluorobenzene, 4.4 parts of cis-N-(3-hydroxy-4-piperidinyl)-benzamide, 3.8 parts of sodium carbonate, 0.1 parts of potassium iodide and 160 parts of 4-methyl-2-pentanone was stirred and refluxed for 20 hours. The reaction mixture was cooled to room temperature and washed with water. The organic phase was dried, filtered and evaporated. The residue was crystallized from 2-propanol, yielding 4.2 parts (57%) of cis-N-[1-[3-(4-fluorophenoxy)propyl]-3-hydroxy-4-piperidinyl]benzamide; mp. 130.5° C. (compound 42).

Following the same procedure and using equivalent amounts of the appropriate starting materials there were also prepared:

methoxy-N-(3-methoxy-4-piperidinyl)benzamide, 5.3 parts of sodium carbonate and 68 parts of N,N-dimethylformamide was stirred for 5 hours at about 60° C. The reaction mixture was cooled to room temperature and filtered. The filtrate was evaporated. The solid residue was purified by column-chromatography over silica gel using a mixture of trichloromethane and methanol (90:10 by volume) as eluent. The pure fractions were collected and the eluent was evaporated. The residue was crystallized from ethanol. The product was filtered off and dried, yielding 3.84 parts (64.2%) of cis-4-amino-5-chloro-2-methoxy-N-[3-methoxy-1-(3-pyridinylmethyl)-4-piperidinyl]benzamide; mp. 188.9° C. (compound 91).

Following the same procedure and using equivalent amounts of the appropriate starting materials there were also prepared:

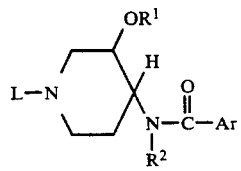

| No. | L | $R^1$ | $R^2$ | Ar | cis/trans isomerism | base/salt form | mp. °C. |
|---|---|---|---|---|---|---|---|
| 73 | (2,3-dihydro-2-oxo-1H-benzimidazol-1-yl)-(CH$_2$)$_3$ | H | H | C$_6$H$_5$ | cis | base | 190 |
| 74 | 4-F—C$_6$H$_4$—O—(CH$_2$)$_3$ | CH$_3$ | H | C$_6$H$_5$ | cis | base | 98.2 |
| 75 | (2,3-dihydro-2-oxo-1H-benzimidazol-1-yl)-(CH$_2$)$_3$ | CH$_3$ | H | C$_6$H$_5$ | cis | base | 210.3 |
| 76 | (2,3-dihydro-2-oxo-1H-benzimidazol-1-yl)-(CH$_2$)$_3$ | CH$_3$ | H | 2-CH$_3$O,4-NH$_2$,5-Cl—C$_6$H$_2$ | cis | base | 112.5 |
| 77 | 2-naphthalenylmethyl | CH$_3$ | H | 2-CH$_3$O,4-NH$_2$,5-Cl—C$_6$H$_2$ | cis | base | 156.2 |
| 78 | (2,3-dihydro-2-oxo-1H-benzimidazol-1-yl)-(CH$_2$)$_2$ | CH$_3$ | H | 2-CH$_3$O,4-NH$_2$,5-Cl—C$_6$H$_2$ | cis | base | 250.5 |
| 79 | CH$_2$=CH—CH$_2$ | CH$_3$ | H | 2-CH$_3$O,4-NH$_2$,5-Cl—C$_6$H$_2$ | cis | base | 176.3 |
| 80 | 2,6-Cl$_2$—C$_6$H$_3$—NH—CO—CH$_2$ | CH$_3$ | H | 2-CH$_3$O,4-NH$_2$,5-Cl—C$_6$H$_2$ | cis | base | 228.3 |
| 81 | 2,6-Cl$_2$—C$_6$H$_3$—NH—CO—CH$_2$CH$_2$ | CH$_3$ | H | 2-CH$_3$O,4-NH$_2$,5-Cl—C$_6$H$_2$ | cis | base | 206.1 |
| 82 | (5-Cl-2,3-dihydro-2-oxo-1H-benzimidazol-1-yl)-(CH$_2$)$_3$ | CH$_3$ | H | 2-CH$_3$O,4-NH$_2$,5-Cl—C$_6$H$_2$ | cis | base | 255.4 |
| 83 | (2,3-dihydro-2-oxo-1H-benzimidazol-1-yl)-(CH$_2$)$_4$ | CH$_3$ | H | 2-CH$_3$O,4-NH$_2$,5-Cl—C$_6$H$_2$ | cis | ½ H$_2$O | 122.5 |
| 84 | 3-Cl—C$_6$H$_4$—CH=CH—CH$_2$ | CH$_3$ | H | 2-CH$_3$O,4-NH$_2$,5-Cl—C$_6$H$_2$ | cis | H$_2$O | 92 |
| 85 | 2,6-(CH$_3$)$_2$—C$_6$H$_3$—NHCO(CH$_2$)$_2$ | CH$_3$ | H | 2-CH$_3$O,4-NH$_2$,5-Cl—C$_6$H$_2$ | cis | base | 177.1 |
| 86 | 2,6-Cl$_2$—C$_6$H$_3$—CONH—(CH$_2$)$_2$ | CH$_3$ | H | 2-CH$_3$O,4-NH$_2$,5-Cl—C$_6$H$_2$ | cis | base | 191.2 |
| 87 | (2,3-dihydro-2-oxo-1H-benzimidazol-1-yl)-(CH$_2$)$_3$ | H | H | 2-CH$_3$O,4-NH$_2$,5-Cl—C$_6$H$_2$ | cis | base | 244.4 |
| 88 | (4-F,2-CH$_3$CO)C$_6$H$_3$—O—(CH$_2$)$_3$ | CH$_3$ | H | 2-CH$_3$O,4-NH$_2$,5-Cl—C$_6$H$_2$ | cis | H$_2$O | 131.4 |
| 89 | 4-F—C$_6$H$_4$—O—CH$_2$—CH$_2$— | CH$_3$ | H | 2-CH$_3$O,4-NH$_2$,5-Cl-C$_6$H$_2$ | cis | base | 103.4 |
| 90 | (2,4-Cl$_2$—C$_6$H$_3$)—O—CH(CH$_3$)—CH$_2$ | CH$_3$ | H | 2-CH$_3$O,4-NH$_2$,5-Cl—C$_6$H$_2$ | cis | base | 134.2 |

EXAMPLE LIX

A mixture of 2.8 parts of 3-(chloromethyl)pyridine hydrochloride, 4.7 parts of cis-4-amino-5-chloro-2- also prepared:

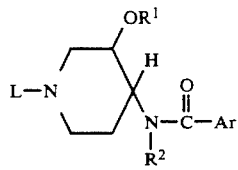

| No. | L | $R^1$ | $R^2$ | Ar | cis/trans isomerism | base/salt form | mp. °C. |
|---|---|---|---|---|---|---|---|
| 92 | 4-F—$C_6H_4$—CO—$(CH_2)_3$ | $CH_3$ | H | $C_6H_5$ | cis | base | 91.6 |
| 93 | 4-F—$C_6H_4$—CO—$(CH_2)_3$ | $CH_3$ | H | $C_6H_5$ | trans | base | 178.2 |
| 94 | 4-F—$C_6H_4$—CO—$(CH_2)_3$ | H | H | $C_6H_5$ | trans | base | 149.6 |
| 95 | 4-F—$C_6H_4$—CO—$(CH_2)_3$ | $CH_3$ | H | 2-$CH_3O$,4-$NH_2$,5-Cl—$C_6H_2$ | cis | base | 181.2 |
| 96 | 2-pyridinylmethyl | $CH_3$ | H | 2-$CH_3O$,4-$NH_2$,5-Cl—$C_6H_2$ | cis | base | 172.6 |
| 97 | 5-(4-F—$C_6H_4$)-3-isoxazolymethyl | $CH_3$ | H | 2-$CH_3O$,4-$NH_2$,5-Cl—$C_6H_2$ | cis | base | 146.6 |
| 98 | 4-(1$\underline{H}$-imidazol-1-yl)phenylmethyl | $CH_3$ | H | 2-$CH_3O$,4-$NH_2$,5-Cl—$C_6H_2$ | cis | base | 261.8 |
| 99 | 3-$CF_3$—$C_6H_4$—$CH_2$ | $CH_3$ | H | 2-$CH_3O$,4-$NH_2$,5-Cl—$C_6H_2$ | cis | base | 138.7 |
| 100 | (4-F—$C_6H_4$)$_2$—CH—$(CH_2)_3$ | $CH_3$ | H | $C_6H_5$ | trans | base | 97 |
| 101 | (2-methylimidazo[1,2-a]pyridin-7-yl)methyl | $CH_3$ | H | 2-$CH_3O$,4-$NH_2$,5-Cl—$C_6H_2$ | cis | $H_2O$ | 196.5 |
| 102 | (imidazo[1,2-a]pyridin-7-yl)methyl | $CH_3$ | H | 2-$CH_3O$,4-$NH_2$,5-Cl—$C_6H_2$ | cis | base | 195.6 |
| 103 | 4-F—$C_6H_4$—O—$(CH_2)_2$ | $CH_3$ | H | 2-$CH_3O$,4-$NH_2$,5-Cl—$C_6H_2$ | cis | base | 152.2 |
| 104 | 4-F—$C_6H_4$—O—$(CH_2)_4$ | $CH_3$ | H | 2-$CH_3O$,4-$NH_2$,5-Cl—$C_6H_2$ | cis | base | 110.3 |
| 105 | (4-F—$C_6H_4$)$_2$C(CN)—$(CH_2)_3$ | $CH_3$ | H | 2-$CH_3O$,4-$NH_2$,5-Cl—$C_6H_2$ | cis | $H_2O$ | 96.1 |
| 106 | 4-F—$C_6H_4$—$SO_2$—$(CH_2)_3$ | $CH_3$ | H | 2-$CH_3O$,4-$NH_2$,5-Cl—$C_6H_2$ | cis | base | 179.5 |
| 107 | 2-pyridinylmethyl | $C_2H_5$ | H | 2-$CH_3O$,4-$NH_2$,5-Cl—$C_6H_2$ | cis | base | 173.8 |
| 108 | 2-pyridinylmethyl | H | H | 2-$CH_3O$,4-$NH_2$,5-Cl—$C_6H_2$ | cis | base | 143.3 |
| 109 | (4-F—$C_6H_4$)$_2$—C[CON($CH_3$)$_2$]—$(CH_2)_3$ | $CH_3$ | H | 2-$CH_3O$,4-$NH_2$,5-Cl—$C_6H_2$ | cis | $H_2O$ | 130.6 |
| 110 | (5-$CH_3$-1$\underline{H}$-imidazol-4-yl)-$CH_2$ | $CH_3$ | H | 2-$CH_3O$,4-$NH_2$,5-Cl—$C_6H_2$ | cis | $H_2O$ | 181.6 |
| 111 | 4-F,2-(4-F—$C_6H_4$—CO)—$C_6H_3$—O—$(CH_2)_3$ | $CH_3$ | H | 2-$CH_3O$,4-$NH_2$,5-Cl—$C_6H_2$ | cis | base | 132.5 |
| 112 | 2-$NH_2CO$,4-F—$C_6H_3$—O—$(CH_2)_3$ | $CH_3$ | H | 2-$CH_3O$,4-$NH_2$,5-Cl—$C_6H_2$ | cis | base | 175.3 |
| 113 | (4-Cl,2-$CH_3$—$C_6H_3$)—O—$(CH_2)_3$ | $CH_3$ | H | 2-$CH_3O$,4-$NH_2$,5-Cl—$C_6H_2$ | cis | base | 101.6 |
| 114 | 3-$CF_3$—$C_6H_4$—O—$(CH_2)_3$ | $CH_3$ | H | 2-$CH_3O$,4-$NH_2$,5-Cl—$C_6H_2$ | cis | base | 83.2 |
| 115 | 4-$NO_2$—$C_6H_4$—O—$(CH_2)_3$ | $CH_3$ | H | 2-$CH_3O$,4-$NH_2$,5-Cl—$C_6H_2$ | cis | base | 186.8 |
| 116 | $C_6H_5$—O—$(CH_2)_3$ | $CH_3$ | H | 2-$CH_3O$,4-$NH_2$,5-Cl—$C_6H_2$ | cis | HCl | 258.7 |
| 117 | [2,2-(4-F—$C_6H_4$)$_2$-1,3-dioxolan-4-yl]methyl | $CH_3$ | H | 2-$CH_3O$,4-$NH_2$,5-Cl—$C_6H_2$ | cis | base | 112.1 |
| 118 | $CH_3O$—$(CH_2)_3$ | $CH_3$ | H | 2-$CH_3O$,4-$NH_2$,5-Cl—$C_6H_2$ | cis | base | 95.3 |
| 119 | ($C_6H_5$)$_2$CH—C(O)—$(CH_2)_3$ | $CH_3$ | H | 2-$CH_3O$,4-$NH_2$,5-Cl—$C_6H_2$ | cis | base | 157.5 |
| 120 | (4-F—$C_6H_4$)($CH_3O$)$_2$C—CH(OH))$(CH_2)_2$ | $CH_3$ | H | 2-$CH_3O$,4-$NH_2$,5-Cl—$C_6H_2$ | cis | base | 215.3 |
| 121 | 4-F—$C_6H_4$—O—$(CH_2)_3$ | $CH_3$ | H | 2-$CH_3O$,4-$NH_2$,5-$SOCH_3$—$C_6H_2$ | cis | $H_2O$ | 148.6–166.8 |

EXAMPLE LX

A mixture of 7.6 parts of N-(dihydro-3,3-diphenyl-2(3H)-furanylidene)-N-methylmethanaminium bromide, 4.7 parts of cis-N-(3-methoxy-4-piperidinyl)benzamide, 3.8 parts of sodium carbonate, 0.1 parts of potassium iodide and 240 parts of 4-methyl-2-pentanone was stirred and refluxed for 18 hours using a water-separator. The reaction mixture was cooled to room temperature and washed with water. The organic phase was separated, dried, filtered and evaporated. The oily residue was purified by column-chromatography over silica gel using a mixture of trichloromethane and methanol (95:5 by volume) as eluent. The pure fractions were collected and the eluent was evaporated. The residue was crystallized from 2,2′-oxybispropane. The product was filtered off and dried, yielding 3.5 parts (35%) of cis-4-(benzoylamino)-3-methoxy-N,N-dimethyl-α,α-diphenyl-1-piperidinebutanamide; mp. 146.6° C. (compound 122).

In a similar manner there were also prepared:

trans-4-(benzoylamino)-3-hydroxy-N,N-dimethyl-α,α-diphenyl-1-piperidinebutanamide; mp. 178.4° C. (compound 123);

trans-4-(benzoylamino)-3-methoxy-N,N-dimethyl-α,α-diphenyl-1-piperidinebutanamide (E)-2-butenedioate (1:1); mp. 163.4° C. (compound 124);

cis-4-(benzoylamino)-3-hydroxy-N,N-dimethyl-α,α-diphenyl-1-piperidinebutanamide ethanedioate (1:1); mp. 209.9° C. (compound 125);

trans-4-(benzoylamino)-3-methoxy-N,N,γ-trimethyl-α,α-diphenyl-1-piperidinebutanamide; mp. 196.1° C. (compound 126);

trans-4-(benzoylamino)-3-hydroxy-N,N,γ-trimethyl-α,α-diphenyl-1-piperidinebutanamide; mp. 176.7° C. (compound 127);

cis-4-(benzoylamino)-3-hydroxy-N,N,γ-trimethyl-α,α-diphenyl-1-piperidinebutanamide; mp. 198.5° C. (compound 128);

cis-4-[(4-amino-5-chloro-2-methoxybenzoyl)amino]-3-hydroxy-N,N,γ-trimethyl-α,α-diphenyl-1- piperidinebutanamide; mp. 223.4° C. (compound 129); and
cis-4-[(4-amino-5-chloro-2-methoxybenzoyl)amino]-3-methoxy-N,N-dimethyl-α,α-diphenyl-1-piperidinebutanamide monohydrate; mp. 128.8° C. (compound 130).

EXAMPLE LXI

A mixture of 11 parts of 1-(4-fluorobenzoyl)aziridine, 6.28 parts of cis-4-amino-5-chloro-2-methoxy-N-(3-methoxy-4-piperidinyl)benzamide, 45 parts of benzene and 20 parts of methanol was stirred and refluxed for 6 hours. The reaction mixture was evaporated and the residue was purified by column-chromatography over silica gel using a mixture of trichloromethane and methanol (90:10 by volume) as eluent. The pure fractions were collected and the eluent was evaporated. The residue was crystallized from acetonitrile, yielding 5.09 parts of cis-4-amino-5-chloro-N-[1-[2-[(4-fluorobenzoyl)amino]ethyl]-3-methoxy-4-piperidinyl]-2-methoxybenzamide; mp. 208.7° C. (compound 131).

EXAMPLE LXII

A mixture of 2.73 parts of α-(4-fluorophenyl)oxiraneethanol, 3.3 parts of cis-N-(3-hydroxy-4-piperidinyl)-benzamide and 80 parts of ethanol was stirred and refluxed for 4 hours. The reaction mixture was evaporated. The residue was purified by column-chromatography over silica gel using a mixture of trichloromethane and methanol (90:10 by volume) as eluent. The pure fractions were collected and the eluent was evaporated. The semi-solid residue was crystallized from acetonitrile, yielding 4.5 parts (74.5%) of cis-N-[1-[4-(4-fluorophenyl)-2,4-dihydroxybutyl-3-hydroxy-4-piperidinyl]benzamide; mp. 172.1° C. (compound 132).

none was stirred and refluxed for 24 hours. Water was added to the reaction mixture. The precipitated product was filtered off and crystallized from N,N-dimethylformamide and a small amount of water, yielding 3.3 parts of cis-4-amino-5-chloro-N-[1-[2-(1,4-dihydro-2,4-dioxo-3(2H)-quinazolinyl)ethyl]-3-methoxy-4-piperidinyl]-2-methoxybenzamide; mp. 270.8° C. (compound 142).

In a similar manner there was also prepared:
cis-4-amino-5-chloro-N-[1-[4-(4-fluoro-2-hydroxyphenyl)-4-oxobutyl]-3-methoxy-4-piperidinyl]-2-methoxybenzamide monohydrate; mp. 165.7° C. (compound 143).

EXAMPLE LXIV 4.7 Parts of cis-4-amino-5-chloro-2-methoxy-N-(3-methoxy-4-piperidinyl)benzamide were dissolved in 160 parts of 2-propanone. Then there were added successively 3.2 parts of [(2-pyrazinyl)methyl] methanesulfonate (ester) and 1.7 parts of sodium hydrogen carbonate. The whole was stirred and refluxed for 18 hours while nitrogen gas was introduced. The precipitated product was filtered off and the filtrate was evaporated. The residue was purified by column-chromatography over silica gel using a mixture of trichloromethane and methanol (95:5 by volume) as eluent. The pure fractions were collected and the eluent was evaporated. The residue was crystallized twice from acetonitrile, yielding 1.16 parts of cis-4-amino-5-chloro-2-methoxy-N-[3-methoxy-1-(2-pyrazinylmethyl)-4-piperidinyl]-benzamide; mp. 203.5° C. (compound 144).

EXAMPLE LXV

To a stirred solution of 40 parts of cis-N-[3-(phenylmethoxy)-4-piperidinyl]benzamide in 153 parts of tetrahydrofuran were added 323 parts of a sodium hydroxide In a similar manner there were also prepared:

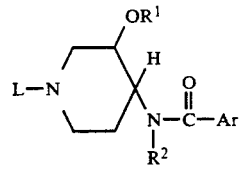

| No. | L | $R^1$ | $R^2$ | Ar | cis/trans isomerism | base/saltform | mp. °C. |
|---|---|---|---|---|---|---|---|
| 133 | 4-F—C$_6$H$_4$—CH(OH)CH$_2$CH(OH)CH$_2$ | H | H | C$_6$H$_5$ | trans | base | 174.1 |
| 134 | 4-F—C$_6$H$_4$—CH(OCH$_3$)CH$_2$CH(OH)CH$_2$ | H | H | C$_6$H$_5$ | trans | base | 167 |
| 135 | 4-F—C$_6$H$_4$—C(OH)(C—C$_3$H$_5$)CH$_2$CH(OH)—CH$_2$ | H | H | C$_6$H$_5$ | trans | base | 166.7 |
| 136 | 4-F—C$_6$H$_4$—C(OH)(C—C$_3$H$_5$)CH$_2$—CH(OH)CH$_2$ | H | H | C$_6$H$_5$ | trans | (COOH)$_2$ | 141 |
| 137 | 4-F—C$_6$H$_4$C(OCH$_3$)CH$_2$CH(OH)CH$_2$ | H | H | C$_6$H$_5$ | trans | CHCOOH ‖ CHCOOH | 199.1 |
| 138 | (4-F—C$_6$H$_4$)$_2$CH—CH$_2$CH(OH)CH$_2$ | H | H | 2-CH$_3$O,4-NH$_2$,5-Cl—C$_6$H$_2$ | cis | base | 111.2 |
| 139 | (4-F—C$_6$H$_4$)—O—CH$_2$—CH(OH)—CH$_2$ | CH$_3$ | H | 2-CH$_3$O,4-NH$_2$,5-Cl— | cis | base | 79.8 |
| 140 | C$_6$H$_4$—CH$_2$—N(CH$_3$)—CH$_2$—CH(OH)CH$_2$ | CH$_3$ | H | 2-CH$_3$O,4-NH$_2$,5-Cl— | cis | 2(COOH)$_2$H$_2$O | 146.7 |
| 141 | (4-F—C$_6$H$_4$)$_2$CH—CH$_2$—CH(OH)—CH$_2$ | CH$_3$ | H | 2-CH$_3$O,4-NH$_2$,5-Cl— | cis | ½ H$_2$O | 107.6 |

EXAMPLE LXIII

A mixture of 3.8 parts of 3-(2-chloroethyl)-2(1H), 4(3H)-quinazolinedione, 4.7 parts of cis-4-amino-5-chloro-2-methoxy-N-(3-methoxy-4-piperidinyl)benzamide, 1.7 parts of sodium hydrogen carbonate, 0.1 parts of potassium iodide and 160 parts of 4-methyl-2-pentasolution 1N. Then there was added dropwise a solution of 15.4 parts of ethyl carbonochloridate in 58 parts of tetrahydrofuran at a temperature below 5° C. Upon completion, stirring was continued for 3 hours while cooling in an ice-bath (temp. below 5° C.). Dichloromethane was added and the layers were separated. The aqueous phase was extracted with dichloromethane. The combined organic phases were washed with water, dried, filtered and evaporated. The residue was suspended in 2,2'-oxybispropane. The product was filtered off and crystallized from acetonitrile. A first fraction was filtered off, yielding 30.2 parts of cis-ethyl 4-(benzoylamino)-3-(phenylmethoxy)-1-piperidinecarboxylate; mp. 139.2° C. The mother liquor was concentrated. The precipitated product was filtered off, yielding a second fraction of 5 parts of cis-ethyl 4-(benzoylamino)-3-(phenylmethoxy)-1-piperidinecarboxylate.

Total yield: 35.2 parts of cis-ethyl 4-(benzoylamino)-3-(phenylmethoxy)-1-piperidinecarboxylate (70.8%) (compound 145).

EXAMPLE LXVI

To 1 part of a solution of 2 parts of thiophene in 40 parts of ethanol were added 12 parts of an acetaldehyde solution 10% in tetrahydrofuran, 6.3 parts of cis-4-amino-5-chloro-2-methoxy-N-(3-methoxy-4-piperidinyl)benzamide and 120 parts of methanol. The whole was hydrogenated at normal pressure and at room temperature with 2 parts of platinum-on-charcoal catalyst 5%. After the calculated amount of hydrogen was taken up, the catalyst was filtered off and the filtrate was evaporated. The residue was suspended in a mixture of 2,2'-oxybispropane and petroleumether.

The product was filtered off and crystallized from acetonitrile. The product was filtered off and dried, yielding a first fraction of 2 parts of cis-4-amino-5-chloro-N-(1-ethyl-3-methoxy-4-piperidinyl)-2-methoxybenzamide monohydrate; mp. 130.2° C.

The mother liquor was concentrated. A second fraction was filtered off, yielding 2.89 parts of cis-4-amino-5-chloro-N-(1-ethyl-3-methoxy-4-piperidinyl)-2-methoxybenzamide monohydrate; mp. 121.1° C. (compound 147);

cis-4-amino-5-chloro-N-[1-(2,3-dihydro-1H-inden-2-yl)-3-methoxy-4-piperidinyl]-2-methoxybenzamide; mp. 237.7° C. (compound 148);

cis-4-amino-5-chloro-N-[1-[2-(cyclohexyloxy)ethyl]-3-methoxy-4-piperidinyl]-2-methoxybenzamide; mp. 118.5° C. (compound 149); and cis-4-amino-5-chloro-N-[1-(2-furanylmethyl)-3-methoxy-4-piperidinyl]-2-methoxybenzamide; mp. 192.6°–195.4° C. (compound 150).

EXAMPLE LXVII

To a stirred solution of 4.3 parts of trans-1-[4,4-bis(4-fluorophenyl)butyl]-3-methoxy-4-piperidinamine and 1.27 parts of N,N-diethylethanamine in 60 parts of trichloromethane was added dropwise a solution of 2.88 parts of 3,4,5-trimethoxybenzoyl chloride in 45 parts of trichloromethane at a temperature below 5° C. The reaction mixture was allowed to reach slowly room temperature and stirring was continued for 18 hours at room temperature.

The solvent was evaporated. The residue was purified by column-chromatography over silica gel using a mixture of trichloromethane and methanol (90:10 by volume) as eluent. The pure fractions were collected and the eluent was evaporated. The residue was converted into the hydrochloride salt in 2-propanone and 2-propanol. The salt was filtered off and dried, yielding 5.27 parts (75.6%) of trans-N-[1-[4,4-bis(4-fluorophenyl)butyl]-3-methoxy-4-piperidinyl]-3,4,5-trimethoxybenzamide monohydrochloride monohydrate; mp. 135.1° C. (compound 151).

Following the same procedure and using equivalent amounts of the appropriate starting materials there were also prepared:

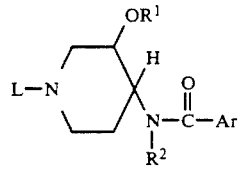

| No. | 1 | $R^1$ | $R^2$ | Ar | cis/trans isomerism | base/salt form | mp. °C. |
|---|---|---|---|---|---|---|---|
| 152 | $C_2H_5OOC$ | H | H | $C_6H_5$ | cis | base | 193 |
| 153 | $C_2H_5OOC$ | H | H | $C_6H_5$ | trans | base | 158.8 |
| 154 | $C_2H_5OOC$ | $CH_3$ | H | $C_6H_5$ | cis | base | 151.2 |
| 155 | $C_6H_5-CH_2$ | $C_6H_5CH_3$ | H | $C_6H_5$ | trans | base | 147.4 |
| 156 | $C_6H_5-CH_2$ | $CH_3$ | H | $C_6H_5$ | trans | base | 181.4 |
| 157 | $C_6H_5-CH_2$ | $C_6H_5CH_2$ | H | $C_6H_5$ | cis | base | 95.5 |
| 158 | $C_6H_5-CH_2$ | $CH_3$ | H | $C_6H_5$ | cis | base | 114.6 |
| 159 | $(4-F-C_6H_4)_2CH(CH_2)_3$ | H | $CH_3$ | $4-F-C_6H_4$ | trans | base | 106.5 |
| 160 | $(4-F-C_6H_4)_2CH(CH_2)_3$ | H | $CH_3$ | $C_6H_5$ | trans | base | 109.4 |
| 161 | $(4-F-C_6H_4)_2CH(CH_2)_3$ | H | H | $4-NO_2-C_6H_4$ | trans | base | 177 |
| 162 | $(4-F-C_6H_4)_2CH(CH_2)_3$ | H | H | $C_6H_5$ | trans | base | 175.8 |
| 163 | $(4-F-C_6H_4)_2CH(CH_2)_3$ | H | H | $3,4,5-(CH_3O)_3-C_6H_2$ | trans | base | 83.1 |
| 164 | $(4-F-C_6H_4)_2CH(CH_2)_3$ | $CH_3$ | H | $4-NO_2-C_6H_4$ | cis | base | 118.3 |
| 165 | $(4-F-C_6H_4)_2CH(CH_2)_3$ | $CH_3$ | H | $3,4,5-(CH_3O)_3-C_6H_2$ | cis | HCl | 186.2 |
| 166 | $(4-F-C_6H_4)_2CH(CH_2)_3$ | H | H | $3,4,5-(CH_3O)_3-C_6H_2$ | cis | $HCl.H_2O$ | 124.4 |
| 167 | $(4-F-C_6H_4)_2CH(CH_2)_3$ | H | H | $3,4,5-(CH_3O)_3-C_6H_2$ | cis | $HCl.H_2O$ | 118.1 | methoxybenzamide monohydrate; mp. 150.5° C. (compound 146).

In a similar manner there were also prepared:
cis-4-amino-N-[1-[4,4-bis(4-fluorophenyl)-1-methylbutyl]-3-methoxy-4-piperidinyl]-5-chloro-2-

EXAMPLE LXVIII

To a stirred solution of 22.5 parts of 4-amino-5-chloro-2-methoxybenzoic acid in 405 parts of trichloromethane were added dropwise successively 11.8 parts of N,N-diethylethanamine and 13 parts of ethyl carbonochloridate at a temperature below 10° C. Stirring was continued for 45 minutes at a temperature below 10° C. Then there was added dropwise a solution of 19.15 parts of cis-ethyl 4-amino-3-methoxy-1-piperidinecarboxylate in 360 parts of trichloromethane at the same temperature. Upon completion, stirring was continued for 18 hours at room temperature. The reaction mixture was washed successively three times with water, once with a 5% sodium hydroxide solution and again twice with water. The organic phase was dried, filtered and evaporated. The residue was purified by column-chromatography over silica gel using a mixture of trichloromethane and methanol (90:10 by volume) as eluent. The pure fractions were collected and the eluent was evaporated, yielding 29.3 parts (80%) of cis-ethyl (4-amino-5-chloro-2-methoxybenzoylamino)-3-methoxy-1-piperidinecarboxylate as a residue (compound 168).

Following the same procedure and using equivalent amounts of the appropriate starting materials there were also prepared:

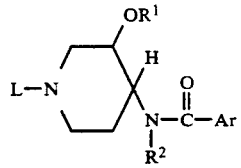

| No. | L | $R^1$ | $R^2$ | Ar | cis/trans isomerism | base/salt form | mp. °C. |
|---|---|---|---|---|---|---|---|
| 169 | $(4\text{-}F\text{-}C_6H_4)_2\text{-}CH\text{-}(CH_2)_3$ | $CH_3$ | H | $2\text{-}CH_3O,4\text{-}NH_2\text{-}C_6H_3$ | cis | $(COOH)_2.H_2O$ | 108.9 |
| 170 | $(4\text{-}F\text{-}C_6H_4)_2\text{-}CH\text{-}(CH_2)_3$ | H | H | $2\text{-}Cl,4\text{-}NO_2\text{-}C_6H_3$ | trans | $HCl.H_2O$ | 164.9 |
| 171 | $4\text{-}F\text{-}C_6H_4\text{-}CH_2$ | $CH_3$ | H | $2\text{-}CH_3O,4\text{-}NH_2,5\text{-}CN\text{-}C_6H_2$ | cis | base | 227.2 |
| 172 | $(4\text{-}F\text{-}C_6H_4)_2CH\text{-}(CH_2)_3$ | $CH_3$ | H | $2\text{-}Cl,4\text{-}NO_2\text{-}C_6H_3$ | cis | base | 131.1 |
| 173 | $(4\text{-}F\text{-}C_6H_4)_2CH\text{-}(CH_2)_3$ | $CH_3$ | H | $2\text{-}CH_3O,4\text{-}NH_2,5\text{-}Cl\text{-}C_6H_2$ | trans | $(COOH)_2$ | 170.8 |
| 174 | $(4\text{-}F\text{-}C_6H_4)_2CH\text{-}(CH_2)_3$ | H | H | $2\text{-}CH_3O,4\text{-}NH_2\text{-}C_6H_3$ | trans | base | 74.5 |
| 175 | $(4\text{-}F\text{-}C_6H_4)_2CH\text{-}(CH_2)_3$ | H | H | $2\text{-}CH_3O,5\text{-}Cl\text{-}C_6H_3$ | trans | HCl | 196.8 |
| 176 | $C_6H_5\text{-}CH_2$ | $CH_3$ | H | $2\text{-}CH_3O,4\text{-}NH(CH_3),5\text{-}Cl\ C_6H_2$ | cis | base | 201.2 |
| 177 | $C_6H_5\text{-}CH_2$ | H | H | $2\text{-}CH_3O,4\text{-}NH(CH_3),5\text{-}Cl\ C_6H_2$ | cis | base | 164.5 |
| 178 | $3\text{-}CH_3O\text{-}C_6H_4\text{-}CH_2$ | $CH_3$ | H | $2\text{-}CH_3O,4\text{-}NH_2,5\text{-}Cl\text{-}C_6H_2$ | cis | ½ $H_2O$ | 103.1 |
| 179 | 1,3-benzodioxol-5-ylmethyl | $CH_3$ | H | $2\text{-}CH_3O,4\text{-}NH_2,5\text{-}Cl\text{-}C_6H_2$ | cis | $H_2O$ | 162.1 |
| 180 | $C_6H_5\text{-}CH_2$ | H | H | $2\text{-}CH_3O,4\text{-}NH(CH_3),6\text{-}Cl\ C_6H_2$ | trans | base | 159.9 |
| 181 | $C_6H_5\text{-}CH_2$ | $CH_3$ | H | $2\text{-}CH_3O,4\text{-}NH(CH_3),6\text{-}Cl\ C_6H_2$ | trans | base | 125.4 |
| 182 | $4\text{-}CH_3O\text{-}C_6H_4\text{-}CH_2$ | $CH_3$ | H | $2\text{-}OCH_3,4\text{-}NH_2,5\text{-}Cl\text{-}C_6H_2$ | cis | $H_2O$ | 119.5 |
| 183 | $(4\text{-}F\text{-}C_6H_4)_2CH\text{-}(CH_2)_3$ | H | H | $2\text{-}OCH_3,4\text{-}NH_2,5\text{-}Cl\text{-}C_6H_2$ | trans | $HCl.H_2O$ | 181.5 |
| 184 | $(4\text{-}F\text{-}C_6H_4)_2\text{-cyclohexyl-H}$ | $CH_3$ | H | $2\text{-}OCH_3,4\text{-}NH_2,5\text{-}Cl\text{-}C_6H_2$ | cis | base | 214.1 |
| 185 | cyclopropyl-$CH_2$ | $CH_3$ | H | $2\text{-}OCH_3,4\text{-}NH_2,5\text{-}Cl\text{-}C_6H_2$ | cis | base | 177.3 |
| 186 | $(CH_3)_2CH$ | $CH_3$ | H | $2\text{-}OCH_3,4\text{-}NH_2,5\text{-}Cl\text{-}C_6H_2$ | cis | base | 151.1 |
| 187 | $C_6H_5CH_2$ | H | H | $2\text{-}OCH_3,5\text{-}NH_2SO_2\text{-}C_6H_3$ | cis | base | 198.2 |
| 188 | $C_6H_5CH_2$ | H | H | $4\text{-}CN\text{-}C_6H_4$ | cis | base | 154.8 |
| 189 | $C_6H_5CH_2$ | H | H | $4\text{-}Br\text{-}C_6H_4$ | cis | base | 171.7 |
| 190 | $C_6H_5CH_2$ | H | H | $2\text{-}OC_2H_5,4\text{-}NH_2,5\text{-}NO_2\text{-}C_6H_2$ | cis | base | 225.4 |
| 191 | $C_6H_5CH_2$ | $CH_3$ | H | $2\text{-}OCH_3,4\text{-}NH_2,5\text{-}Cl\text{-}C_6H_2$ | trans | $(COOH)_2H_2O$ | 232.1 |
| 192 | $C_6H_5CH_2$ | H | H | $2\text{-}CH_3COO\text{-}C_6H_4$ | cis | base | residue |
| 193 | $C_6H_5CH_2$ | H | H | $2\text{-}CH_3O,4\text{-}NH_2,5\text{-}Cl\text{-}C_6H_2$ | trans | base | 188.3 |
| 194 | $C_6H_5CH_2$ | H | H | $2\text{-}CH_3O,4\text{-}NH_2,5\text{-}Cl\text{-}C_6H_2$ | cis | base | 210.1 |
| 195 | $C_2H_5\text{-}OOC$ | H | H | $2\text{-}CH_3O,4\text{-}NH_2,5\text{-}Cl\text{-}C_6H_2$ | cis | base | 190.1 |
| 196 | $C_6H_5CH_2$ | $CH_3$ | H | $2\text{-}CH_3O,4\text{-}NH_2,5\text{-}Cl\text{-}C_6H_2$ | cis | base | 184.2 |
| 197 | $C_2H_5\text{-}OC(O)$ | $C_2H_5$ | H | $2\text{-}CH_3O,4\text{-}NH_2,5\text{-}Cl\text{-}C_6H_2$ | cis | base | — |
| 198 | $C_2H_5\text{-}OC(O)$ | $CH_3$ | $CH_3$ | $2\text{-}CH_3O,4\text{-}NH_2,5\text{-}Cl\text{-}C_6H_2$ | cis | base | — |
| 199 | $4\text{-}F\text{-}C_6H_4\text{-}O\text{-}(CH_2)_3$ | $CH_3$ | H | $2\text{-}CH_3O,4\text{-}NH_2,5\text{-}CN\text{-}C_6H_2$ | cis | $H_2O$ | 137.7 |
| 200 | (4,5,6,7-tetrahydro-1H-benzimidazol-2-yl)$CH_2$ | $CH_3$ | H | $2\text{-}CH_3O,4\text{-}NH_2,5\text{-}Cl\text{-}C_6H_2$ | cis | base | 221.1 |
| 201 | $4\text{-}F\text{-}C_6H_4\text{-}O\text{-}(CH_2)_3$ | $CH_3$ | H | $2\text{-}CH_3O,4\text{-}NH_2,5\text{-}Br\text{-}C_6H_2$ | cis | $H_2O$ | 105.12 |
| 202 | $C_6H_5\text{-}CH_2$ | $CH_3$ | H | $2\text{-}CH_3O,4\text{-}NH_2,5\text{-}CN\text{-}C_6H_2$ | cis | base | 208.3 |
| 203 | $4\text{-}F\text{-}C_6H_4\text{-}O\text{-}(CH_2)_3$ | $CH_3$ | H | $2\text{-}CH_3O,4\text{-}OH,5\text{-}Cl\text{-}C_6H_2$ | cis | $H_2O$ | 123.2 |
| 204 | $4\text{-}F\text{-}C_6H_4\text{-}O\text{-}(CH_2)_3$ | $CH_3$ | H | $2\text{-}CH_3O,4\text{-}NH_2,5\text{-}Cl\text{-}C_6H_2$ | cis(+) | base | 129.6 |
| 205 | $4\text{-}F\text{-}C_6H_4\text{-}O\text{-}(CH_2)_3$ | $CH_3$ | H | $2\text{-}CH_3O,4\text{-}NH,5\text{-}Cl\text{-}C_6H_2$ | cis(−) | base | 125.0 |
| 206 | $4\text{-}F\text{-}C_6H_4\text{-}O\text{-}(CH_2)_3$ | $CH_3$ | H | $2\text{-}CH_3O,5\text{-}C_3H_7CO\text{-}C_6H_2$ | cis | base | 91.4 |
| 207 | $4\text{-}F\text{-}C_6H_4\text{-}O\text{-}(CH_2)_3$ | $CH_3$ | H | $2\text{-}CH_3O,4\text{-}NH_2,5\text{-}Cl\text{-}C_6H_2$ | trans | $H_2O$ | 108.2 |
| 208 | $4\text{-}F\text{-}C_6H_4\text{-}O\text{-}(CH_2)_3$ | $(C_2H_5)_2N\text{-}(CH_2)_2$ | H | $2\text{-}CH_3O,4\text{-}NH_2,5\text{-}Cl\text{-}C_6H_2$ | cis | $2HCl.H_2O$ | 228.6 |
| 209 | $C_2H_5\text{-}O\text{-}CO$ | $CH_3$ | H | $2\text{-}CH_3O,4\text{-}CH_3CO,5\text{-}CH_3SO\text{-}C_6H_2$ | cis | base | 171.4–179.3 |

-continued

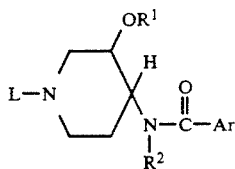

| No. | L | $R^1$ | $R^2$ | Ar | cis/trans isomerism | base/salt form | mp. °C. |
|---|---|---|---|---|---|---|---|
| 210 | $C_2H_5$—O—CO | $CH_3$ | H | 2-$CH_3$O,4-$CH_3$CONH, 5-$CH_3$S—$C_6H_2$ | cis | base | 128.7–137.9 |

EXAMPLE LXIX

A mixture of 16.6 parts of cis-ethyl 4-(4-amino-5-chloro-2-methoxybenzoylamino)-3-methoxy-1-piperidinecarboxylate, 26.36 parts of potassium hydroxide and 160 parts of 2-propanol was stirred and refluxed for 3 hours. The reaction mixture was evaporated in vacuo on a boiling water-bath. Water was added to the residue and the whole was evaporated again. The residue was boiled in water on a warm water-bath. The precipitated product was filtered off and taken up in trichloromethane. The organic phase was separated, dried, filtered and evaporated. The residue was taken up in methylbenzene. The solid residue was filtered off and dried, yielding 6.7 parts (46%) of cis-4-amino-5-chloro-2-methoxy-N-(3-methoxy-4-piperidinyl)-benzamide; mp. 184.3° C. (compound 211).

In a similar manner there were also prepared:

cis-N-(3-hydroxy-4-piperidinyl)benzamide; mp. 169.7° C. (compound 212);

cis-N-(3-methoxy-4-piperidinyl)benzamide ethanedioate (1:1); mp. 219° C. (compound 213);

cis-4-amino-5-chloro-N-(3-hydroxy-4-piperidinyl)-2-methoxybenzamide; mp. 197.4° C. (compound 214);

cis-4-amino-5-chloro-N-(3-ethoxy-4-piperidinyl)-2-methoxybenzamide monohydrate; mp. 114.5° C. (compound 215);

cis-4-amino-5-chloro-2-methoxy-N-(3-methoxy-4-piperidinyl)-N-methylbenzamide; mp. 167.4° C. (compound 216); and cis-4-amino-2-methoxy-5-(methylsulfinyl)-N-(3-methoxy-4-piperidinyl)benzamide as a residue (compound 217).

Example LXX

A solution of 22.9 parts of trans-N-[3-(phenylmethoxy)-1-(phenylmethyl)-4-piperidinyl]benzamide in 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated. The residue was suspended in 2,2'-oxybispropane. The product was filtered off and suspended in trichloromethane. The whole was shaken with a dilute ammonium hydroxide solution and the layers were separated. The aqueous phase was evaporated and the solid residue was suspended in 5 parts of water. The product was filtered off and dried, yielding 6 parts of trans-N-(3-hydroxy-4-piperidinyl)benzamide; mp. 210° C. (compound 218).

In a similar manner there were also prepared:

trans-N-(3-methoxy-4-piperidinyl)benzamide (compound 219); and cis-4-amino-6-methoxy-$N^1$-(3-methoxy-4-piperidinyl)-1,3-benzenedicarboxamide hemihydrate; mp. 194.5° C. (compound 220).

Example LXXI

A mixture of 150 parts of cis-N-[3-(phenylmethoxy)-1-(phenylmethyl)-4-piperidinyl]benzamide and 400 parts of methanol was hydrogenated at normal pressure and at room temperature with 9 parts of palladium-on-charcoal catalyst 10%. After the calculated amount of hydrogen was taken up, the catalyst was filtered off and the filtrate was evaporated. The residue was crystallized from acetonitrile. The product was filtered off and dried, yielding a first fraction of 42 parts of cis-N-[3-(phenylmethoxy)-4-piperidinyl]-benzamide.

The mother-liquor was evaporated, yielding 70 parts of cis-N-[3-(phenylmethoxy)-4-piperidinyl]benzamide as an oily residue (compound 221).

Example LXXII

A mixture of 4.14 parts of trans-N-[1-[4,4-bis(4-fluorophenyl)butyl]-3-hydroxy-4-piperidinyl]-4-nitrobenzamide and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was converted into the hydrochloride salt in 2-propanol and methylbenzene. The salt was filtered off and crystallized from a mixture of acetonitrile and a small amount of N,N-dimethylformamide, yielding 2.59 parts (57.8%) of trans-4-amino-N-[1-[4,4-bis(4-fluorophenyl)butyl]-3-hydroxy-4-piperidinyl]benzamide dihydrochloride; mp. 240.4° C. (compound 222).

In a similar manner there were also prepared:

cis-4-amino-N-[1-[4,4-bis(4-fluorophenyl)butyl]-3-methoxy-4-piperidinyl]benzamide; mp. 114.3° C. (compound 223);

trans-4-amino-N-[1-[4,4-bis(4-fluorophenyl)butyl]-3-hydroxy-4-piperidinyl]-2-chlorobenzamide; mp. 72.4° C. (compound 224);

cis-4-amino-N-[1-[4,4-bis(4-fluorophenyl)butyl]-3-methoxy-4-piperidinyl]-2-chlorobenzamide ethanedioate (1:2) monohydrate; mp. 100.9° C. (compound 225);

cis-4-amino-5-chloro-N-[1-[3-(2-amino-4-fluorophenoxy)propyl]-3-methoxy-4-piperidinyl]-2-methoxybenzamide; mp. 183.5° C. (compound 226);

cis-4-amino-N-[1-[3-(4-aminophenoxy)propyl]-3-methoxy-4-piperidinyl]-5-chloro-2-methoxybenzamide; mp. 170.7° C. (compound 227); and cis-4-amino-N-[1-[4-(2-amino-4-fluorophenoxy)cyclohexyl]-3-methoxy-4-piperidinyl]-5-chloro-2-methoxybenzamide; mp. 229.7° C. (compound 228).

Example LXXIII

To a stirred and cooled (ice-bath) solution of 6.64 parts of cis-4-amino-5-chloro-N-[3-hydroxy-1-(2-pyridinylmethyl)-4-piperidinyl]-2-methoxybenzamide in 68 parts of tetrahydrofuran were added 1.95 parts of N,N-diethylethanamine. Then there was added dropwise a solution of 1.41 parts of acetyl chloride in 27 parts of tetrahydrofuran at about 0° C. Upon completion, the mixture was allowed to reach slowly room temperature and stirring was continued for 18 hours at this temperature. Sodium carbonate was added and the whole was evaporated. The residue was taken up in water and the product was extracted with dichloromethane. The extract was washed with water, dried, filtered and evaporated. The residue was purified by column-chromatography over silica gel using a mixture of trichloromethane and methanol (95:5 by volume) as eluent. The pure fractions were collected and the eluent was evaporated. The residue was further purified by HPLC using a mixture of trichloromethane and methanol (97:3 by volume) as eluent. The first fraction was collected and the eluent was evaporated. The residue was suspended in petroleumether. The product was filtered off and dried, yielding 2.03 parts of cis-4-[[4-(acetylamino)-5-chloro-2-methoxybenzoyl]amino]-1-(2-pyridinylmethyl)-3-piperidinol acetate (ester); mp. 179.4° C. (compound 229).

The second fraction was collected and the eluent was evaporated. The residue was suspended in petroleumether. The product was filtered off and dried, yielding 2.44 parts of cis-4-[(4-amino-5-chloro-2-methoxybenzoyl)amino]-1-(2-pyridinylmethyl)-3-piperidinol acetate (ester); mp. 181.7° C. (compound 230).

Example LXXIV

To a stirred solution of 7.5 parts of cis-4-amino-5-chloro-N-[1-[3-(4-fluorophenoxy)propyl]-3-hydroxy-4-piperidinyl]-2-methoxybenzamide in 68 parts of tetrahydrofuran were added dropwise 1.94 parts of N,N-diethylethanamine. After cooling to 0° C., 1.4 parts of acetyl chloride dissolved in 9 parts of tetrahydrofuran were added dropwise at a temperature below 0° C. Upon completion, stirring was continued for a while in an ice-bath. The mixture was allowed to reach slowly room temperature and stirring was continued overnight at room temperature. The solvent was evaporated and the residue was taken up in a saturate sodium carbonate solution. The product was extracted with methylbenzene. The extract was washed with water, dried, filtered and evaporated. The residue was purified twice by column-chromatography over silica gel using first a mixture of trichloromethane and methanol (95:5 by volume) and then a mixture of trichloromethane, hexane and methanol (48:48:4 by volume) as eluent. The first fraction was collected and the eluent was evaporated. The residue was suspended in petroleumether. The product was filtered off and dried, yielding 0.59 parts of cis-4-[[4-(acetylamino)-5-chloro-2-methoxybenzoyl]amino]-1-[3-(4-fluorophenoxy)-propyl]-3-piperidinol acetate (ester); mp. 172.2° C. (compound 231).

Example LXXV

To a stirred solution of 7.5 parts of cis-4-amino-5-chloro-N-[1-[3-(4-fluorophenoxy)propyl]-3-hydroxy-4-piperidinyl]-2-methoxybenzamide in 68 parts of tetrahydrofuran were added dropwise 2.02 parts of N,N-diethylethanamine. After cooling to 0° C., there was added dropwise a solution of 1.4 parts of acetyl chloride in 9 parts of tetrahydrofuran at a temperature below 0° C.

Upon completion, stirring was continued for a while while cooling in an ice-bath. The reaction mixture was allowed to reach slowly room temperature and stirring was continued overnight at room temperature. The reaction mixture was evaporated and the residue was taken up in a sodium carbonate solution in water. The product was extracted with methylbenzene. The extract was washed with water, dried, filtered and evaporated. The residue was purified by column-chromatography over silica gel using a mixture of trichloromethane and methanol (95:5 by volume) as eluent. The pure fractions were collected and the eluent was evaporated. The residue was further separated by HPLC using a mixture of trichloromethane, hexane and methanol (48:48:4 by volume) as eluent. The second fraction (B-isomer) was collected and the eluent was evaporated. The residue was suspended in petroleumether. The product was filtered off and dried, yielding 1.7 parts of cis-4-[(4-amino-5-chloro-2-methoxybenzoyl)amino]-1-[3-(4-fluorophenoxy)propyl]-3-piperidinol acetate (ester); mp. 58.8° C. (compound 232).

Example LXXVI 10 parts of cis-4-amino-5-chloro-N-[1-[3-(4-fluorophenoxy)propyl]-3-methoxy-4-piperidinyl]-2-methoxybenzamide were dissolved in 225 parts of hot trichloromethane. After cooling to room temperature, 3.6 parts of N,N-diethylethanamine were added. Then there was added dropwise a solution of 1.7 parts of acetyl chloride in 30 parts of trichloromethane:exothermic reaction. The whole was stirred and refluxed for 22 hours. After cooling to room temperature, 0.6 parts of acetyl chloride were added and stirring was continued overnight at reflux. Another 0.6 parts of acetyl chloride were added and stirring was continued overnight at reflux. After cooling again to room temperature, there were added successively 0.6 parts of acetyl chloride and a small amount of N,N-dimethyl-4-pyridinamine. Stirring was continued for 22 hours at reflux. The reaction mixture was cooled to room temperature and washed with water. The organic phase was dried, filtered and evaporated. The residue was crystallized twice from acetonitrile, yielding 2.78 parts (25.5%) of cis-4-(acetylamino)-5-chloro-N-[1-[3-(4-fluorophenoxy)propyl]-3-methoxy-4-piperidinyl]-2-methoxybenzamide; mp. 175.6° C. (compound 233).

Example LXXVII

To 65 parts of a sulfuric acid solution 96% were added portionwise (slowly) 3.6 parts of cis-4-amino-5-cyano-N-[1-[(4-fluorophenyl)methyl]-3-methoxy-4-piperidinyl]-2-methoxybenzamide while cooling in an ice-bath. The reaction mixture was allowed to reach room temperature and stirring was continued for 7 hours at room temperature. The reaction mixture was poured onto crushed ice and the whole was alkalized with ammonium hydroxide. The product was extracted with trichloromethane. The extract was washed with water, dried, filtered and evaporated. The residue was purified by column-chromatography over silica gel using a mixture of trichloromethane and methanol (90:10 by volume) as eluent. The most pure fractions were collected and the eluent was evaporated. The residue was further purified by HPLC using a mixture of methylbenzene and ethanol (90:10 by volume) as eluent. The pure fraction was collected and the eluent was evaporated. The residue was boiled in acetonitrile. The product was filtered off and dried, yielding 2.67 parts of cis-4-amino-$N^1$-[1-[(4-fluorophenyl)methyl]-3-methoxy-4-piperidinyl]-6-methoxy-1,3-benzenedicarboxamide; mp. 243.7° C. (compound 234).

Example LXXVIII

A mixture of 5 parts of cis-2-[3-hydroxy-1-(phenylmethyl)-4-piperidinylaminocarbonyl]phenol acetate (ester) and 30 parts of sodium hydroxide solution 1N was stirred and heated for four hours at 60° C. The reaction mixture was cooled to room temperature and neutralized with a hydrochloric acid solution 1N. The product was extracted with 1,1'-oxybisethane. The extract was dried, filtered and evaporated. The residue was purified by column-chromatography over silica gel using a mixture of trichloromethane and methanol (85:15 by volume) as eluent. The pure fractions were collected and the eluent was evaporated. The residue solidified on triturating in 2,2'-oxybispropane. The product was filtered off and dried, yielding 1.21 parts (27%) of cis-2-hydroxy-N-[3-hydroxy-1-(phenylmethyl)-4-piperidinyl]benzamide; mp. 127.1° C. (compound 235).

Example LXXIX

285 Parts of sulfuric acid were cooled in an ice-bath and 15.5 parts of cis-4-amino-5-cyano-2-methoxy-N-[3-methoxy-1-(phenylmethyl)-4-4-piperidinyl]benzamide were added portionwise while cooling. Upon completion, stirring was continued overnight at room temperature. The reaction mixture was poured onto ice-water and the whole was alkalized with ammonium hydroxide. The product was filtered off and stirred in a mixture of trichloromethane and water. The product was filtered off again and dried, yielding 15.0 parts of cis-4-amino-6-methoxy-$N^1$-[3-methoxy-1-(phenylmethyl)-4piperidinyl]-1,3-benzenedicarboxamide (compound 236).

Example LXXX

A mixture of 3.12 parts of cis-4-amino-5-chloro-N-[1-[4-(4-fluorophenyl)-3-butenyl]-3-methoxy-4-piperidinyl]-2-methoxybenzamide 120 parts of methanol was hydrogenated at normal pressure and at room temperature with 2 parts of platinum-on-charcoal catalyst 5%. After the calculated amount of hydrogen was taken up, the catalyst was filtered off and the filtrate was evaporated. The residue was stirred in 1,1'-oxybisethane. The product was filtered off and dried, yielding 2.54 parts (81%) of cis-4-amino-5-chloro-N-[1-[4-(4-fluorophenyl)butyl]-3-methoxy-4-piperidinyl]-2-methoxybenzamide monohydrate; mp. 132.7° C. (compound 237).

Example LXXXI

A mixture of 2.88 parts of cis-4-amino-5-chloro-N-[1-[4-(4-fluorophenyl)-3-hydroxy-4,4-dimethoxybutyl]-3-methoxy-4-piperidinyl]-2-methoxybenzamide, 30 parts of concentrate hydrochloric acid and 25 parts of water was stirred for 18 hours at room temperature. 100 Parts of water were added and the whole was alkalized with ammonia. The precipitated product was filtered off and taken up in trichloromethane. The organic phase was separated, dried, filtered and evaporated. The residue was purified by column-chromatography over silica gel using a mixture of trichloromethane and methanol (95:5 by volume) saturated with ammonia, as eluent. The pure fractions were collected and the eluent was evaporated. The residue was taken up in benzene. Upon the addition of petroleumether, the product was precipitated. It was filtered off and dried, yielding 0.47 parts (16%) of cis-4-amino-5-chloro-N-[1-[4-(4-fluorophenyl)-3-hydroxy-4-oxobutyl]-3-methoxy-4-piperidinyl]-2-methoxybenzamide; mp. 146.4° C. (compound 238).

Example LXXXII

40 Parts of cis-4-amino-5-chloro-N-[1-[3-(4-fluorophenoxy)propyl]-3-methoxy-4-piperidinyl]-2-methoxybenzamide monohydrate were boiled in 160 parts of methanol. The product was filtered off while hot and crystallized twice from a mixture of 600 parts of tetrachloromethane and 400 parts of trichloromethane. The product was filtered off, dried and recrystallized from 4-methyl-2-pentanone. The product was filtered off and dried (water-separator) yielding 18.5 parts of cis-4-amino-5-chloro-N-[2-chloro-4-[[1-[3-(4-fluorophenoxy)propyl]-3-methoxy-4-piperidinyl]-aminocarbonyl]-5-methoxyphenyl]-2-methoxybenzamide; mp. 181.5° C. (compound 239).

Example LXXXIII

To a stirred solution of 4 parts of cis-4-amino-5-chloro-N-[1-[3-(4-fluorophenoxy)propyl]-3-methoxy-4-piperidinyl]-2-methoxybenzamide in 64 parts of ethanol was added a solution of 1 part of (Z)-2-butenedioic acid in 16 parts of ethanol and the product was allowed to crystallize. It is filtered off and dried, yielding 4.8 parts (92%) of cis-4-amino-5-chloro-N-[1-[3-(4-fluorophenoxy)propyl]-3-methoxy-4-piperidinyl]-2-methoxybenzamide (Z)-2-butenedioate (1:1); mp. 200.3° C. (compound 240).

Following the same procedure there were also prepared:

cis-(+)-4-amino-5-chloro-N-[1-[3-(4-fluorophenoxy)propyl]-3-methoxy-4-piperidinyl]-2-methoxybenzamide [R-(R*,R*)]-2,3-dihydroxybutanedioate (1:1); mp. 197.1° C. $[\alpha] = +6.7327°$ (c=1% methanol) (compound 241);

cis-4-amino-5-chloro-N-[1-[3-(4-fluorophenoxy)-propyl]-3-methoxy-4-piperidinyl]-2-methoxybenzamide sulfate (1:1); mp. 238.6° C. (compound 242);

cis-4-amino-5-chloro-N-[1-[3-(4-fluorophenoxy)-propyl]-3-methoxy-4-piperidinyl]-2-methoxybenzamide 2-hydroxy-1,2,3-propanetricarboxylate (1:1); mp. 168.1° C. (compound 243); and cis-4-amino-5-chloro-N-[1-[3-(4-fluorophenoxy)-propyl]-3-methoxy-4-piperidinyl]-2-methoxybenzamide monohydrochloride; mp. 249.7° C. (compound 244).

Example LXXXIV

30 Parts of cis-4-amino-5-chloro-N-[1-[3-(4-fluorophenoxy)propyl]-3-methoxy-4-piperidinyl]-2-methoxybenzamide monohydrate were dissolved in 280 parts of methylbenzene at reflux temperature and the solution was stirred and refluxed for 2 hours using a water-separator. 180 Parts of methylbenzene were distilled off. The residue was allowed to cool overnight while stirring. The solid product was filtered off and boiled for 1.50 hours in heptane. The product was filtered off and dried, yielding 23.1 parts of cis-4-amino-5-chloro-N-[1-[3-(4-fluorophenoxy)propyl]-3-methoxy-4-piperidinyl]-2-methoxybenzamide; mp. 131.7°–133° C. (compound 245).

Example LXXXV

A mixture of 11.6 parts of cis-4-amino-5-chloro-N-[1-[3-(4-fluorophenoxy)propyl]-3-methoxy-4-piperidinyl]-2-methoxybenzamide, 3.4 parts of hydrogen peroxide 30%, 270 parts of benzene and 160 parts of methanol was stirred for 5 hours at 60° C. Another 3.4 parts of hydrogen peroxide 30% were added and the whole was stirred overnight at 60° C. The reaction mixture was evaporated to dry. Water was added to the residue and the whole was stirred. The precipitated product was filtered off and crystallized from 2-propanol. The product was filtered off and dried, yielding 5.6 parts of cis-4-amino-5-chloro-N-[1-[3-(4-fluorophenoxy)propyl]-3-methoxy-4-piperidinyl]-2-methoxybenzamide, N-oxide; mp. 129.7° C. (compound 246).

Example LXXXVI 3.8 Parts of cis-4-amino-5-chloro-N-[1-[3-(4-fluorophenoxy)propyl]-3-methoxy-4-piperidinyl]-2-methoxybenzamide were taken up in 60 parts of acetonitrile. The whole was evaporated and the residue was taken up in methylbenzene. The latter was evaporated again. The residue was dissolved in 60 parts of acetonitrile and 1.16 parts of iodomethane were added. Stirring was continued for 5 hours at room temperature (CaCl$_2$-tube). The precipitated product was filtered off and boiled in acetonitrile. The product was filtered off while hot, dried and crystallized from methanol. The product was filtered off and recrystallized from water, yielding 0.84 parts of cis-4-[(4-amino-5-chloro-2-methoxybenzoyl)amino]-1-[3-(4-fluorophenoxy)propyl]-3-methoxy-1-methylpiperidinium iodide hemihydrate; mp. 221.5° C. (compound 247).

What is claimed is:

1. A compound of the formula:

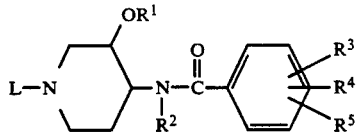

the pharmaceutically acceptable acid addition salts thereof, the stereochemically isomeric forms, and the pharmaceutically acceptable quaternary ammonium salts thereof, wherein:
the substituents in the 3 and 4 positions in the piperidine ring have the cis configuration;
$R^1$ represents a member selected from the group consisting of hydrogen, lower alkyl, (Ar$^1$) lower alkyl, and lower alkylcarbonyl;
$R^2$ represents hydrogen;
$R^3$, $R^4$, and $R^5$ each independently represent hydrogen, lower alkyl, lower alkyloxy, halo, hydroxy, amino, nitro, mono- or di(lower alkyl)amino, lower alkylcarbonylamino, lower alkylcarbonyl, lower alkylcarbonyloxy, aminosulfonyl, and lower alkylsulfonyl; and
L represents hydrogen or lower alkyloxycarbonyl,
wherein in the foregoing Ar$^1$ represents a member selected from the group consisting of phenyl being optionally substituted with up to 3 substituents each independently selected from the group consisting of halo, hydroxy, lower alkyl, lower alkyloxy, aminosulfonyl, lower alkylcarbonyl, nitro, trifluoromethyl, amino, aminocarbonyl, phenylcarbonyl wherein said phenyl may be optionally substituted with up to 3 halo atoms, and thienyl substituted with halo or lower alkyl.

2. A compound according to claim 1 wherein $R^3$, $R^4$, and $R^5$ are, each independently, selected from the group consisting of halo, amino, mono- and di(lower alkyl)amino, and lower alkyloxy.

3. A compound according to claim 2 wherein $R^3$ represents methoxy, $R^4$ represents amino or methylamino, and $R^5$ represents chloro, wherein said $R^3$, $R^4$, and $R^5$ are attached to the phenyl ring in the 2-, 4-, and 5-positions, respectively.

4. A compound according to claim 3 wherein L represents hydrogen or ethoxycarbonyl.

5. A compound according to claim 1 wherein the compound is a member selected from the group consisting of:
cis-4-amino-5-chloro-2-methoxy-N-(3-methoxy-4-piperidinyl)-benzamide; and
cis-ethyl(4-amino-5-chloro-2-methoxybenzoylamino)-3-methoxy-1-piperidinecarboxylate.

6. A pharmaceutical composition in unit dosage form comprising per dosage unit an effective gastro-intestinal motility stimulating amount of a compound as described in claim 1, the pharmaceutically acceptable acid addition salts thereof, the stereochemically isomeric forms, and the pharmaceutically acceptable quaternary ammonium salts thereof.

7. The pharmaceutical composition of claim 6 wherein $R^3$, $R^4$, and $R^5$ are, each independently, selected from the group consisting of halo, amino, mono- and di(lower alkyl)amino, and lower alkyloxy.

8. The pharmaceutical composition of claim 7 wherein $R^3$ represents methoxy, $R^4$ represents amino or methylamino, and $R^5$ represents chloro, wherein said $R^3$, $R^4$, and $R^5$ are attached to the phenyl ring in the 2-, 4-, and 5-positions, respectively.

9. The pharmaceutical composition of claim 8 wherein L represents hydrogen or ethoxycarbonyl.

10. The pharmaceutical composition of claim 6 wherein the compound is a member selected from the group consisting of:
cis-4-amino-5-chloro-2-methoxy-N-(3-methoxy-4-piperidinyl)-benzamide; and
cis-ethyl(4-amino-5-chloro-2-methoxybenzoylamino)-3-methoxy-1-piperidinecarboxylate.

11. A method of stimulating the motility of the gastro-intestinal system which comprises the systemic administration to vertebrates of an effective gastro-intestinal motility stimulating amount of a compound as described in claim 1, the pharmaceutically acceptable acid addition salts thereof, the stereochemically isomeric forms, and the pharmaceutically acceptable quaternary ammonium salts thereof.

12. A method according to claim 11 wherein $R^3$, $R^4$, and $R^5$ are, each independently, selected from the group consisting of halo, amino, mono- and di(lower alkyl)amino, and lower alkyloxy.

13. A method according to claim 12 wherein $R^3$ represents methoxy, $R^4$ represents amino or methylamino, and $R^5$ represents chloro, wherein said $R^3$, $R^4$, and $R^5$ are attached to the phenyl ring in the 2-, 4-, and 5-positions, respectively.

14. A method according to claim 13 wherein L represents hydrogen or ethoxycarbonyl.

15. A method according to claim 11 wherein the compound is a member selected from the group consisting of:

cis-4-amino-5-chloro-2-methoxy-N-(3-methoxy-4-piperidinyl)-benzamide; and cis-ethyl(4-amino-5-chloro-2-methoxybenzoylamino)-3-methoxy-1-piperidinecarboxylate.

* * * * *